US008065240B2

(12) United States Patent
Jung et al.

(10) Patent No.: US 8,065,240 B2
(45) Date of Patent: Nov. 22, 2011

(54) COMPUTATIONAL USER-HEALTH TESTING RESPONSIVE TO A USER INTERACTION WITH ADVERTISER-CONFIGURED CONTENT

(75) Inventors: Edward K. Y. Jung, Bellevue, WA (US); Eric C. Leuthardt, St. Louis, MO (US); Royce A. Levien, Lexington, MA (US); Robert W. Lord, Seattle, WA (US); Mark A. Malamud, Seattle, WA (US)

(73) Assignee: The Invention Science Fund I, Bellevue, WA (US)

( * ) Notice: Subject to any disclaimer, the term of this patent is extended or adjusted under 35 U.S.C. 154(b) by 1043 days.

(21) Appl. No.: 11/982,333

(22) Filed: Oct. 31, 2007

(65) Prior Publication Data
US 2009/0112617 A1 Apr. 30, 2009

(51) Int. Cl.
G06F 15/18 (2006.01)
(52) U.S. Cl. .......................................... 706/2
(58) Field of Classification Search .................. 706/2
See application file for complete search history.

(56) References Cited

U.S. PATENT DOCUMENTS

| | | |
|---|---|---|
| 3,925,763 A | 12/1975 | Wadhwani et al. |
| 3,940,863 A | 3/1976 | Kritzberg |
| 4,191,962 A | 3/1980 | Sramek |
| 5,176,145 A | 1/1993 | Ryback et al. |
| 5,233,520 A | 8/1993 | Kretsch et al. |
| 5,235,319 A | 8/1993 | Hill et al. |
| 5,867,821 A | 2/1999 | Ballantyne et al. |
| 5,910,107 A | 6/1999 | Iliff |
| 5,913,310 A | 6/1999 | Brown |
| 5,961,448 A | 10/1999 | Swenson et al. |
| 5,963,137 A | 10/1999 | Waters, Sr. |
| 6,000,828 A | 12/1999 | Leet |
| 6,024,699 A | 2/2000 | Surwit et al. |
| 6,067,466 A | 5/2000 | Selker et al. |
| 6,081,660 A | 6/2000 | Macleod et al. |
| 6,084,661 A | 7/2000 | Mendelson et al. |
| 6,085,752 A | 7/2000 | Kehr et al. |
| 6,087,090 A | 7/2000 | Mascarenhas |

(Continued)

FOREIGN PATENT DOCUMENTS

JP 2005/253609 A 9/2005
(Continued)

OTHER PUBLICATIONS

Training neural networks to count white blood cells via a minimum counting error objective function, Theera-Umpon, N.; Gader, P.D.; Pattern Recognition, 2000. Proceedings. 15th International Conference on vol. 2 Digital Object Identifier: 10.1109/ICPR.2000.906072 Publication Year: 2000 , pp. 299-302 vol. 2.*

(Continued)

Primary Examiner — Michael B Holmes
(74) Attorney, Agent, or Firm — Keller LaPuma Woodard PC; Gerald M. Keller

(57) ABSTRACT

Methods, apparatuses, computer program products, devices and systems are described that carry out specifying at least one of a plurality of user-health test functions responsive to an interaction between a user and at least one advertiser-specified attribute; and transmitting at least one output of the at least one user-health test function related to the at least one advertiser-specified attribute.

50 Claims, 13 Drawing Sheets

U.S. PATENT DOCUMENTS

| | | | |
|---|---|---|---|
| 6,099,319 A | 8/2000 | Zaltman et al. | |
| 6,167,333 A | 12/2000 | Gehlot | |
| 6,186,145 B1 | 2/2001 | Brown | |
| 6,270,456 B1 | 8/2001 | Iliff | |
| 6,292,687 B1 | 9/2001 | Lowell et al. | |
| 6,334,778 B1 | 1/2002 | Brown | |
| 6,475,161 B2 | 11/2002 | Teicher et al. | |
| 6,524,239 B1 | 2/2003 | Reed et al. | |
| 6,561,811 B2 | 5/2003 | Rapoza et al. | |
| 6,574,599 B1 | 6/2003 | Lim et al. | |
| 6,579,231 B1 | 6/2003 | Phipps | |
| 6,625,578 B2 | 9/2003 | Spaur et al. | |
| 6,653,930 B1 | 11/2003 | Bonomo et al. | |
| 6,684,276 B2 | 1/2004 | Walker et al. | |
| 6,692,436 B1 | 2/2004 | Bluth et al. | |
| 6,699,188 B2 | 3/2004 | Wessel | |
| 6,702,757 B2 | 3/2004 | Fukushima et al. | |
| 6,757,898 B1 | 6/2004 | Ilsen et al. | |
| 6,790,178 B1 | 9/2004 | Mault et al. | |
| 6,804,656 B1 | 10/2004 | Rosenfeld et al. | |
| 6,820,037 B2 | 11/2004 | Simon | |
| 6,852,069 B2 | 2/2005 | Park | |
| 6,865,421 B2 | 3/2005 | Bradley | |
| 6,940,422 B1 | 9/2005 | Bachelder et al. | |
| 6,999,931 B2 | 2/2006 | Zhou | |
| 7,001,334 B2 * | 2/2006 | Reed et al. | 600/300 |
| 7,010,497 B1 | 3/2006 | Nyhan et al. | |
| 7,038,588 B2 | 5/2006 | Boone et al. | |
| 7,125,382 B2 | 10/2006 | Zhou et al. | |
| 7,154,398 B2 | 12/2006 | Chen et al. | |
| 7,156,808 B2 | 1/2007 | Quy | |
| 7,223,234 B2 | 5/2007 | Stupp et al. | |
| 7,227,893 B1 | 6/2007 | Srinivasa et al. | |
| 7,229,288 B2 | 6/2007 | Stuart et al. | |
| 7,311,666 B2 | 12/2007 | Stupp et al. | |
| 7,334,892 B2 | 2/2008 | Goodall et al. | |
| 7,383,282 B2 | 6/2008 | Whitehead et al. | |
| 7,383,283 B2 | 6/2008 | Carrabis | |
| 7,460,903 B2 | 12/2008 | Pineda et al. | |
| 7,509,263 B1 | 3/2009 | Fiedotin et al. | |
| 7,536,171 B2 | 5/2009 | Frank et al. | |
| 7,571,308 B1 | 8/2009 | Bahl et al. | |
| 7,729,755 B2 | 6/2010 | Laken | |
| 7,801,686 B2 * | 9/2010 | Hyde et al. | 702/19 |
| 7,942,816 B2 | 5/2011 | Satoh et al. | |
| 7,953,613 B2 | 5/2011 | Gizewski | |
| 7,974,787 B2 * | 7/2011 | Hyde et al. | 702/19 |
| 2002/0004742 A1 | 1/2002 | Willcocks et al. | |
| 2002/0022973 A1 | 2/2002 | Sun et al. | |
| 2002/0042725 A1 | 4/2002 | Mayaud | |
| 2002/0058867 A1 | 5/2002 | Breiter et al. | |
| 2002/0111741 A1 | 8/2002 | Abraham-Fuchs et al. | |
| 2002/0116224 A1 | 8/2002 | Hengerer et al. | |
| 2002/0123673 A1 | 9/2002 | Webb et al. | |
| 2002/0128960 A1 | 9/2002 | Lambiotte et al. | |
| 2002/0193707 A1 | 12/2002 | Atlas et al. | |
| 2003/0067542 A1 | 4/2003 | Monroe | |
| 2003/0110498 A1 | 6/2003 | Stone | |
| 2003/0130873 A1 | 7/2003 | Nevin et al. | |
| 2003/0153023 A1 | 8/2003 | Starzl et al. | |
| 2003/0167149 A1 | 9/2003 | Simon | |
| 2003/0214630 A1 | 11/2003 | Winterbotham | |
| 2003/0222096 A1 | 12/2003 | Kennedy et al. | |
| 2003/0233034 A1 | 12/2003 | Varri et al. | |
| 2004/0092809 A1 | 5/2004 | DeCharms | |
| 2004/0158297 A1 | 8/2004 | Gonzalez | |
| 2004/0171460 A1 | 9/2004 | Park | |
| 2004/0176076 A1 | 9/2004 | Uppuluri | |
| 2004/0197750 A1 | 10/2004 | Donaher et al. | |
| 2004/0236601 A1 | 11/2004 | Summers et al. | |
| 2004/0267570 A1 | 12/2004 | Becker | |
| 2005/0021372 A1 | 1/2005 | Mikkelsen et al. | |
| 2005/0038311 A1 | 2/2005 | Kuth | |
| 2005/0065814 A1 | 3/2005 | Schmidt et al. | |
| 2005/0071679 A1 | 3/2005 | Kiss et al. | |
| 2005/0119547 A1 | 6/2005 | Shastri et al. | |
| 2005/0130295 A1 | 6/2005 | Li | |
| 2005/0187436 A1 | 8/2005 | Doniger et al. | |
| 2005/0250995 A1 | 11/2005 | Quy | |
| 2005/0273017 A1 | 12/2005 | Gordon | |
| 2005/0278196 A1 | 12/2005 | Potarazu et al. | |
| 2005/0283055 A1 | 12/2005 | Shirai et al. | |
| 2006/0036152 A1 | 2/2006 | Kozel | |
| 2006/0077958 A1 | 4/2006 | Mallya et al. | |
| 2006/0100910 A1 | 5/2006 | Brown | |
| 2006/0161553 A1 | 7/2006 | Woo | |
| 2006/0173246 A1 | 8/2006 | Zaleski | |
| 2006/0183980 A1 | 8/2006 | Yang | |
| 2006/0198533 A1 | 9/2006 | Wang et al. | |
| 2006/0241718 A1 | 10/2006 | Tyler et al. | |
| 2006/0252014 A1 | 11/2006 | Simon et al. | |
| 2006/0264730 A1 | 11/2006 | Stivoric et al. | |
| 2006/0294084 A1 | 12/2006 | Patel et al. | |
| 2007/0016265 A1 | 1/2007 | Davoodi et al. | |
| 2007/0027482 A1 | 2/2007 | Parnis et al. | |
| 2007/0043616 A1 | 2/2007 | Kutaragi et al. | |
| 2007/0079331 A1 | 4/2007 | Datta et al. | |
| 2007/0136093 A1 | 6/2007 | Rankin et al. | |
| 2007/0166675 A1 | 7/2007 | Atkins et al. | |
| 2007/0197882 A1 | 8/2007 | Smith et al. | |
| 2007/0208233 A1 | 9/2007 | Kovacs | |
| 2007/0282177 A1 | 12/2007 | Pilz | |
| 2007/0293732 A1 | 12/2007 | Delahunt et al. | |
| 2008/0039737 A1 | 2/2008 | Breiter et al. | |
| 2008/0133273 A1 | 6/2008 | Marshall | |
| 2008/0162352 A1 | 7/2008 | Gizewski | |
| 2008/0172781 A1 | 7/2008 | Popowich et al. | |
| 2008/0242951 A1 | 10/2008 | Jung et al. | |
| 2008/0298603 A1 | 12/2008 | Smith | |
| 2010/0068684 A1 | 3/2010 | Sabel | |

FOREIGN PATENT DOCUMENTS

| | | |
|---|---|---|
| KR | 10-2004-0017924 A | 3/2004 |
| WO | WO 2007/016241 A2 | 2/2007 |

OTHER PUBLICATIONS

Syntactic Decision Rules for Recognition of Spoken Words and Phrases Using a Stochastic Automaton, Kashyap, R. L.; Pattern Analysis and Machine Intelligence, IEEE Transactions on vol. PAMI-1, Issue: 2 Digital Object Identifier: 10.1109/TPAMI.1979. 4766901 Publication Year: 1979, pp. 154-163.*

Inference of a probabilistic finite state machine from its output, Rouvellou, I.; Hart, G.W.; Systems, Man and Cybernetics, IEEE Transactions on vol. 25, Issue: 3 Digital Object Identifier: 10.1109/21.364856 Publication Year: 1995, pp. 424-437.*

An adaptive function neural network (ADFUNN) for phrase recognition, Miao Kang; Palmer-Brown, D.; Neural Networks, 2005. IJCNN '05. Proceedings. 2005 IEEE International Joint Conference on vol. 1 Digital Object Identifier: 10.1109/IJCNN.2005.1555898 Publication Year: 2005, pp. 593-597 vol. 1.*

Childre, Doc; "A Change of Heart Changes Everything, Freeze-Framer 2.0, Interactive Learning System with Patented Heart Rhythm Monitor"; bearing a date of 2004; 13 pages; Quantum Intech, Inc.; Boulder Creek, CA.

"Draft Device Bulletin: In Vitro Diagnostic Medical Devices Used in Combination—Advice to Users"; Medicines and Healthcare products Regulatory Agency; bearing a date of May 2006; pp. 1-13.

Federhofer, Judith; "Medical Expert Systems: Doctor's Silent Partners"; pp. 1-2; located at http://www.computer.privateweb.at/judith/special_field3.htm.

"Management and Use of IVD Point of Care Test Devices"; Medical Devices Agency; bearing a date of Mar. 2002; pp. 1-31 (including cover page, table of contents, etc.); Crown Copyright.

Mann, Jeff; "EM guidemap—Tremor"; pp. 1-10; located at http://www.jeffmann.net/NeuroGuidemaps/tremor.html; printed on May 9, 2007.

Miller, Greg; "Society for Neuroscience Meeting: Computer Game Sharpens Aging Minds"; Science; bearing a date of Nov. 25, 2005; vol. 310, No. 5752; pp. 1261 (pp. 1-2 attached); American Association for the Advancement of Science; located at: http://www.sciencemag.org/cgi/content/full/310/5752/1261a; printed on Nov. 27, 2006.

"Near-Infrared Chewing Measurement"; Hamamatsu; p. 1; located at http://jp.hamamatsu.com/en/rd/publication/scientific_american/common/pdf/scientific_0509.pdf; printed on Oct. 26, 2007.

"Odd Bedfellows, Striking Results"; Economist.com: Print Edition Technology Quarterly; bearing a date of Dec. 8, 2005; pp. 1-3; The Economist Newspaper and The Economist Group.

"Oxygen Level Monitor"; Hamamatsu; p. 1; located at http://jp.hamamatsu.com/en/rd/publication/scientific_american/common/pdf/scientific_0508.pdf; printed on Oct. 26, 2007.

"Pupil Response Tracker"; Hamamatsu; p. 1; located at http://jp.hamamatsu.com/en/rd/publication/scientific_american/common/pdf/scientific_0608.pdf; printed on Oct. 26, 2007.

"Physical Examination: Diagnosis of Brain, Spinal Cord, and Nerve Disorders"; Merck Manual; bearing a date of Feb. 2003; pp. 1-4; located at http://www.merck.com/mmhe/sec06/ch007/ch007c.html#tb077_1; printed on May 9, 2007.

Rowland, Christopher; "Life Sciences: Robotic Bears Can Monitor Sick Kids: MIT's Device Packed With Sensors"; The Boston Globe; bearing a date of Jul. 31, 2006; pp. 1-3; located at: http://www.boston.com/yourlife/health/diseases/articles/2006/07/31/robotic_bears_can_monitor_sick_kids/; printed on Nov. 22, 2006.

"Spatial Light Modulator Technology"; Hamamatsu; p. 1; located at http://jp.hamamatsu.com/en/rd/publication/scientific_american/common/pdf/scientific_0709.pdf; printed on Oct. 26, 2007.

Stiehl, W. Dan; "Projects: The Huggable: A Robotic Companion for Therapeudic Applications"; Robotic Life—sociable robots; pp. 1-2 located at http://robotic.media.mit.edu/projects/theHuggable.html; printed on Nov. 22, 2006.

Stiehl, Walter Dan; Breazeal, Cynthia; "Affective Touch for Robotic Companions"; Proceedings of Affective Computing and Intelligent Interation; Bejing, bearing a date of 2005; Bejing, China; pp. 1-8; located at http://icampus.mit.edu/projects/Huggable.shtml.

Stiehl, Walter Dan; Lieberman, Jeff; Breazeal, Cynthia; Basel, Louis; Lalla, Levi; Wolf, Michael; "Design of a Therapeutic Robotic Companion for Relational, Affective Touch"; IEEE International Workshop on Robots and Human Interactive Communication, Nashville, TN; bearing a date of 2005; pp. 408-415; IEEE; located at http://icampus.mit.edu/projects/Huggable.shtml.

Stiehl, Walter Dan; Lieberman, Jeff; Breazeal, Cynthia; Basel, Louis; Lalla, Levi; Wolf, Michael; "The Design of the Huggable: A Therapeutic Robotic Companion for Relational, Affective Touch"; Proceedings of AAAI Fall Symposium on Caring Machines, Washington D.C.; bearing a date of 2005; pp. 1-8; American Association for Artificial Intelligence; located at http://icampus.mit.edu/projects/Huggable.shtml.

"Ultra-Fast Camera"; Hamamatsu; p. 1; located at http://jp.hamamatsu.com/en/rd/publication/scientific_american/common/pdf/scientific_0710.pdf; printed on Oct. 26, 2007.

Van Noorden, Richard; "Computer Games Could Save Your Brain: Researchers to Check Whether FreeCell Can Detect Early Signs of Alzheimer's"; News@nature.com; bearing a date of Jul. 24, 2006; pp. 1-3; Nature Publishing Group; located at: http://news.nature.com/news/2006/060724/060724-2.html.

Zhong, Sheng, et al.; "Privacy-Enhancing k-Anonymization of Customer Data"; *PODS* 2005; bearing a date of Jun. 13-15, 2005; Baltimore, MD. pp. 1-9.

Gorini, Alessandra et al.; "Virtual Worlds, Real Healing"; Science; bearing a date of Dec. 7, 2007; p. 1549; vol. 318; No. 5856; AAAS.

"Virtual Reality Pain Reduction"; Human Interface Technology Lab: VR Pain Control; pp. 1-3; located at http://www.hitl.washington.edu/projects/vrpain/ ; printed on Apr. 18, 2008.

Kurtz, Matthew M. et al.; "A Virtual Reality Apartment as a Measure of Medication Management Skills in Patients with Schizophrenia: A Pilot Study"; Schizophrenia Bulletin; bearing a date of 2007; pp. 1162-1170; vol. 33; No. 5; Oxford University Press.

"Using Hypnosis for Spinal Cord Injury Pain Management"; Northwest Regional Spinal Cord Injury System: SCI Forum Report; pp. 1-5; located at http://sci.washington.edu/info/forums/reports/hypnosis_for_sci_pain.asp; printed on Jun. 20, 2008.

Paul-Labrador, Maura et al.; "Effects of Randomized Controlled Trial of Transcendental Meditation on Components of the Metabolic Syndrome With Coronary Heart Disease"; Arch Intern Med; bearing a date of Jun. 12, 2006; pp. 1218-1224; vol. 166; located at: www.archinternmed.com; American Medical Association.

"Fear of Flying and Other Phobias"; Virtual Reality Medical Center; p. 1; located at http://www.vrphobia.com/; printed on Apr. 23, 2008.

Cohen, M.X.; Heller, A.S.; Ranganath, C.; "Functional connectivity with anterior cingulate and orbitofrontal cortices during decision-making"; Cognitive Brain Research; bearing a date of Feb. 19, 2005; pp. 61-70; vol. 23; 2005 Elsevier B.V.; doi:10.1016/j.cogbrainres.2005.01.010; located at http://www.elsevier.com/locate/cogbrainres.

Kurlowicz, Lenore, PhD, RN, CS; Wallace, Meredith, PhD, RN, MSN; The Mini Mental State Examination (MMSE); *try this: Best Practices in Nursing Care to Older Adults*; from The Hartford Institute for Geriatric Nursing; Issue No. 3, Jan. 1999; pp. 1-2.

PCT International Search Report; International App. No. PCT/US08/004142; Sep. 25, 2008; pp. 1-4.

PCT International Search Report; International App. No. PCT/US08/004185; Sep. 25, 2008; pp. 1-4.

PCT International Search Report; International App. No. PCT/US08/004187; Sep. 29, 2008; pp. 1-3.

PCT International Search Report; International App. No. PCT/US08/06197; Oct. 20, 2008; pp. 1-3.

PCT International Search Report; International App. No. PCT/US08/006245; Oct. 29, 2008; pp. 1-3.

PCT International Search Report; International App. No. PCT/US2008/006243; Dec. 10, 2008; pp. 1-3.

Quirk, Gregory J.; Russo, Gregory K.; Barron, Jill L.; Lebron, Kelimer; "The Role of Ventromedial Prefrontal Cortex in the Recovery of Extinguished Fear"; The Journal of Neuroscience, bearing a date of Aug. 15, 2000; 20(16):6225-6231; pp. 1-7.

UK Intellectual Property Office Examination Report under Section 18(3); App. No. GB0918582.8; Mar. 16, 2010 ; pp. 1-3.

UK Intellectual Property Office Examination Report under Section 18(3); Application No. GB0918569.5; dated May 10, 2011; pp. 1-4.

Van Der Hiele, K. et al.; "EEG and MRI correlates of mild cognitive impairment and Alzheimer's disease"; Neurobiol Aging; bearing a date of 2006; pp. 41-58; vol. 28, Issue 9.

* cited by examiner

FIG. 13

1300 Computing System Environment

1304 Device (e.g., a workstation or other desktop computing device)

1302 Computing device

1308 Storage medium

1310 Computer-executable instructions operable to:

(a)   specify at least one of a plurality of user-health test functions responsive to an interaction between a user and at least one advertiser-specified attribute; and (b)   transmit at least one output of the at least one user-health test function related to the at least one advertiser-specified attribute

1306

1304 Device

106 User

COMPUTATIONAL USER-HEALTH TESTING RESPONSIVE TO A USER INTERACTION WITH ADVERTISER-CONFIGURED CONTENT

RELATED APPLICATIONS

The present application is related to the following Related Applications. All subject matter of the Related Applications and of any and all parent, grandparent, great-grandparent, etc. applications of the Related Applications is incorporated herein by reference to the extent such subject matter is not inconsistent herewith.

RELATED APPLICATIONS

U.S. patent application Ser. No. 11/981,650, entitled POLLING FOR INTEREST IN COMPUTATIONAL USER-HEALTH TEST OUTPUT, naming Edward K. Y. Jung; Eric C. Leuthardt; Royce A. Levien; Robert W. Lord; and Mark A. Malamud as inventors, filed 30 Oct. 2007.

U.S. patent application Ser. No. 11/811,865, entitled COMPUTATIONAL USER-HEALTH TESTING, naming Edward K. Y. Jung; Eric C. Leuthardt; Royce A. Levien; Robert W. Lord; and Mark A. Malamud as inventors, filed 11 Jun. 2007.

U.S. patent application Ser. No. 11/807,220, entitled COMPUTATIONAL USER-HEALTH TESTING, naming Edward K. Y. Jung; Eric C. Leuthardt; Royce A. Levien; Robert W. Lord; and Mark A. Malamud as inventors, filed 24 May 2007.

U.S. patent application Ser. No. 11/804,304, entitled COMPUTATIONAL USER-HEALTH TESTING, naming Edward K. Y. Jung; Eric C. Leuthardt; Royce A. Levien; Robert W. Lord; and Mark A. Malamud as inventors, filed 15 May 2007.

U.S. patent application Ser. No. 11/731,745, entitled EFFECTIVE RESPONSE PROTOCOLS FOR HEALTH MONITORING OR THE LIKE, naming Edward K. Y. Jung; Eric C. Leuthardt; Royce A. Levien; Robert W. Lord; and Mark A. Malamud as inventors, filed 30 Mar. 2007.

U.S. patent application Ser. No. 11/731,778, entitled CONFIGURING SOFTWARE FOR EFFECTIVE HEALTH MONITORING OR THE LIKE, naming Edward K. Y. Jung; Eric C. Leuthardt; Royce A. Levien; Robert W. Lord; and Mark A. Malamud as inventors, filed 30 Mar. 2007.

U.S. patent application Ser. No. 11/731,801, entitled EFFECTIVE LOW PROFILE HEALTH MONITORING OR THE LIKE, naming Edward K. Y. Jung; Eric C. Leuthardt; Royce A. Levien; Robert W. Lord; and Mark A. Malamud as inventors, filed 30 Mar. 2007.

TECHNICAL FIELD

This description relates to data capture and data handling techniques.

SUMMARY

An embodiment provides a method. In one implementation, the method includes but is not limited to specifying at least one of a plurality of user-health test functions responsive to an interaction between a user and at least one advertiser-specified attribute; and transmitting at least one output of the at least one user-health test function related to the at least one advertiser-specified attribute. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

An embodiment provides a system. In one implementation, the system includes but is not limited to circuitry for specifying at least one of a plurality of user-health test functions responsive to an interaction between a user and at least one advertiser-specified attribute; and circuitry for transmitting at least one output of the at least one user-health test function related to the at least one advertiser-specified attribute. In addition to the foregoing, other system aspects are described in the claims, drawings, and text forming a part of the present disclosure.

An embodiment provides a computer program product. In one implementation, the computer program product includes but is not limited to a signal-bearing medium bearing (a) one or more instructions for specifying at least one of a plurality of user-health test functions responsive to an interaction between a user and at least one advertiser-specified attribute; and (b) one or more instructions for transmitting at least one output of the at least one user-health test function related to the at least one advertiser-specified attribute. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device cause the computing device to (a) specify at least one of a plurality of user-health test functions responsive to at least one advertiser-specified attribute; and (b) transmit at least one output of the at least one user-health test function related to the at least one advertiser-specified attribute. In addition to the foregoing, other system aspects are described in the claims, drawings, and text forming a part of the present disclosure.

In one or more various aspects, related systems include but are not limited to computing means and/or programming for effecting the herein-referenced method aspects; the computing means and/or programming may be virtually any combination of hardware, software, and/or firmware configured to effect the herein-referenced method aspects depending upon the design choices of the system designer.

In addition to the foregoing, various other method and/or system and/or program product aspects are set forth and described in the teachings such as text (e.g., claims and/or detailed description) and/or drawings of the present disclosure.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE DRAWINGS

With reference now to FIG. 1, shown is an example of a user interaction and data processing system in which embodiments may be implemented, perhaps in a device and/or through a network, which may serve as a context for introducing one or more processes and/or devices described herein.

Figure 3:
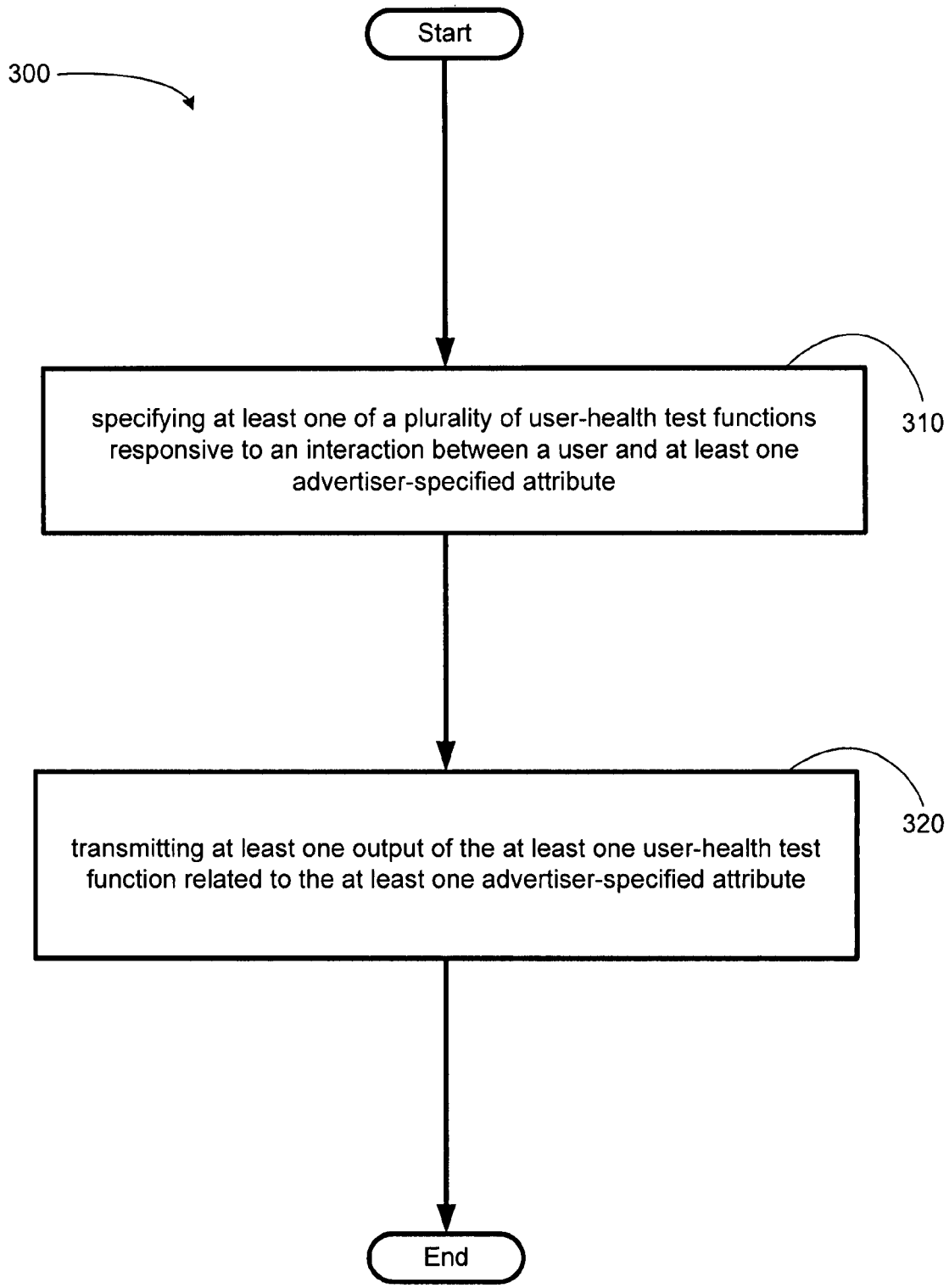

With reference now to FIG. 3, shown is an example of an operational flow representing example operations related to computational user-health testing responsive to advertiser-configured content, which may serve as a context for introducing one or more processes and/or devices described herein.

Figure 4:
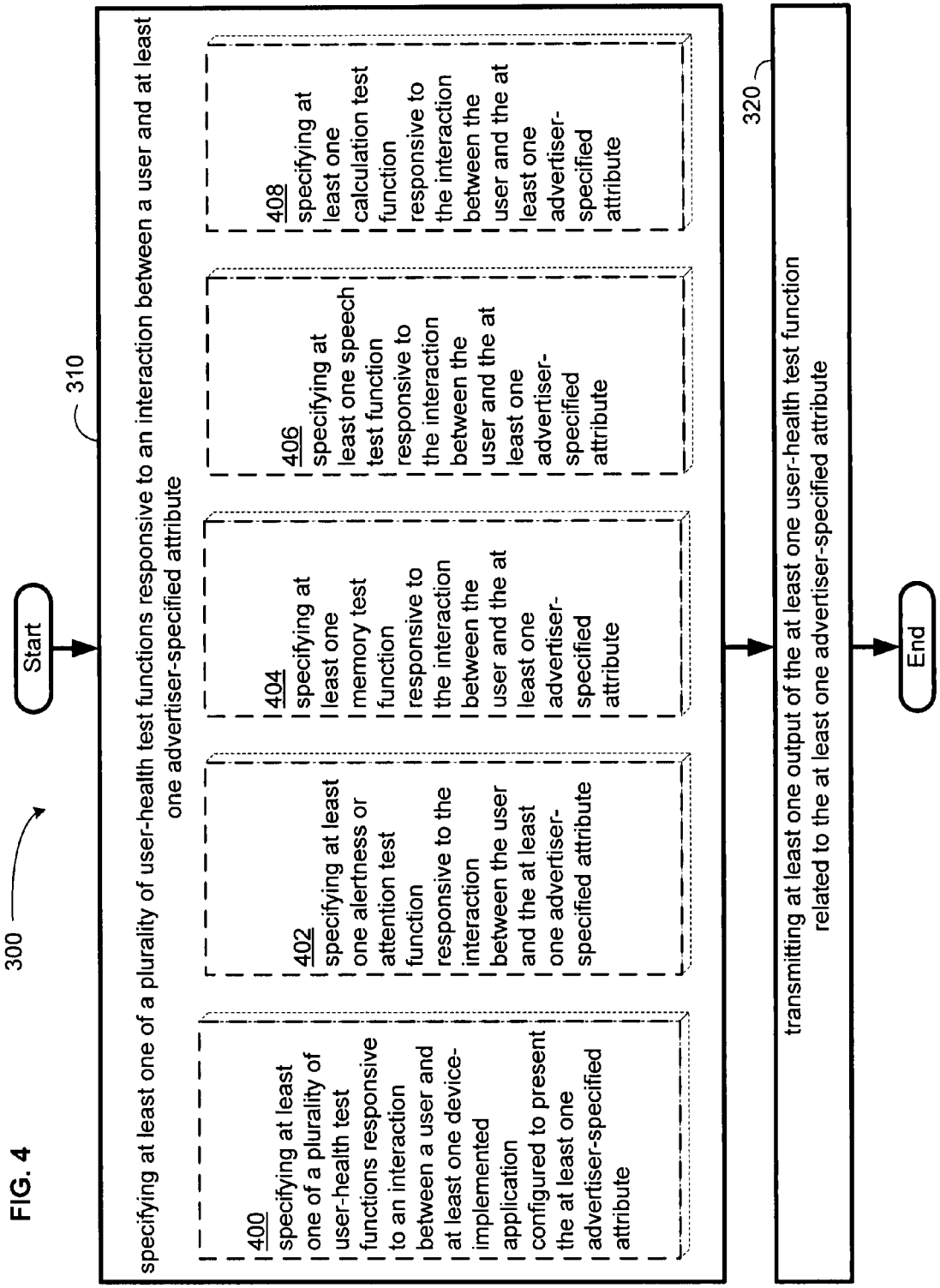

FIG. 4 illustrates an alternative embodiment of the example operational flow of FIG. 3.

Figure 5:
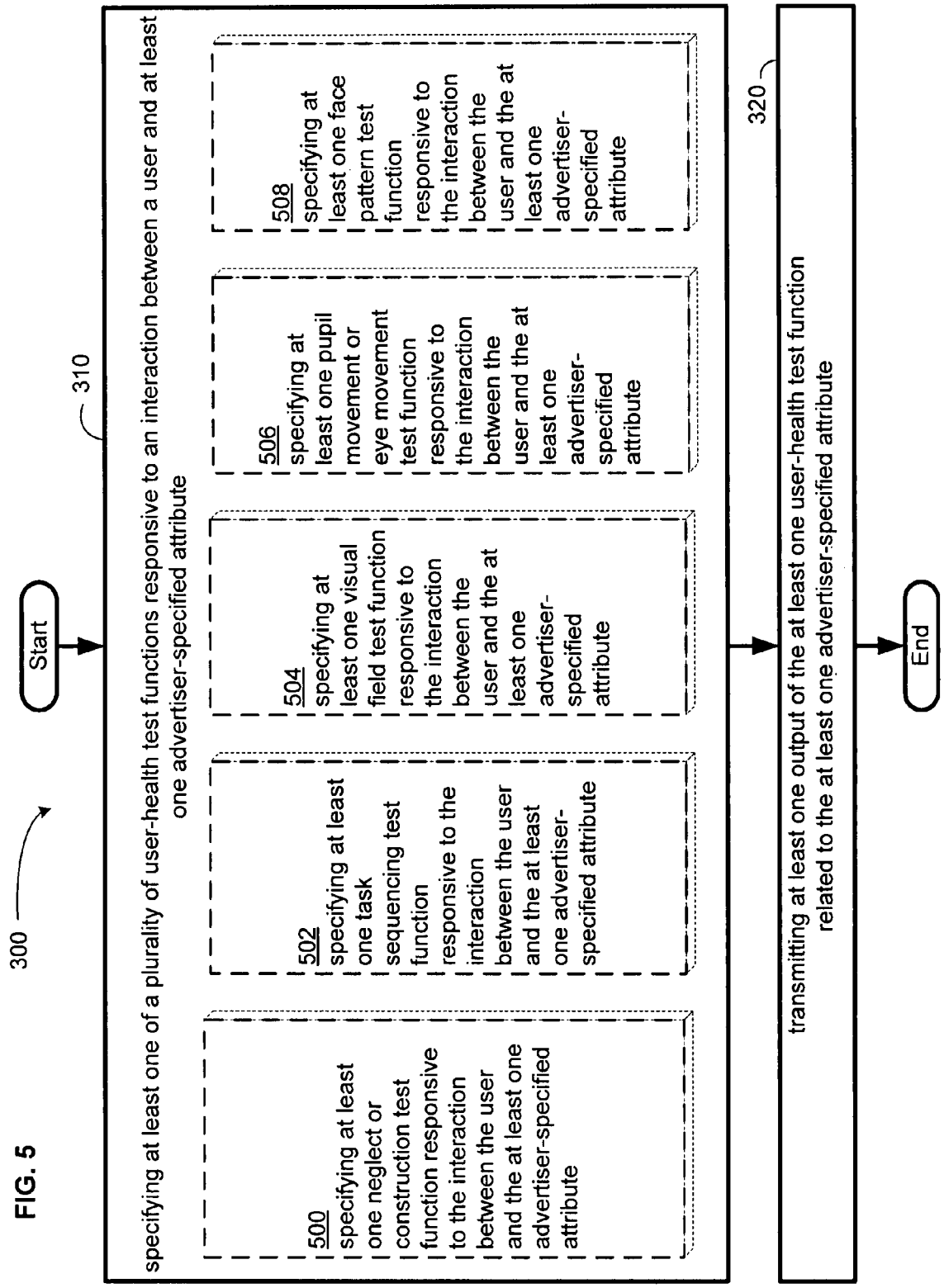

FIG. 5 illustrates an alternative embodiment of the example operational flow of FIG. 3.

Figure 6:
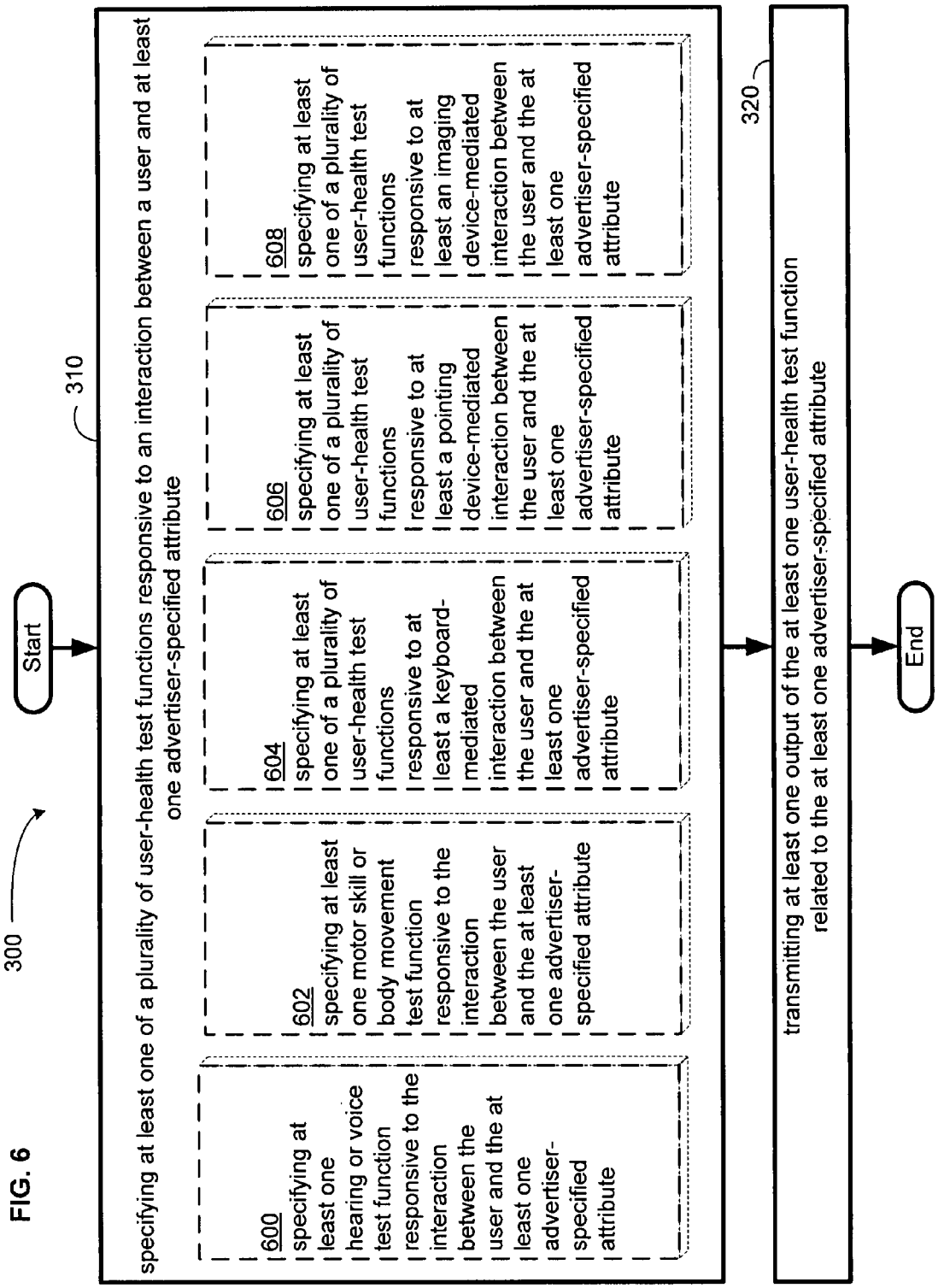

FIG. 6 illustrates an alternative embodiment of the example operational flow of FIG. 3.

Figure 7:
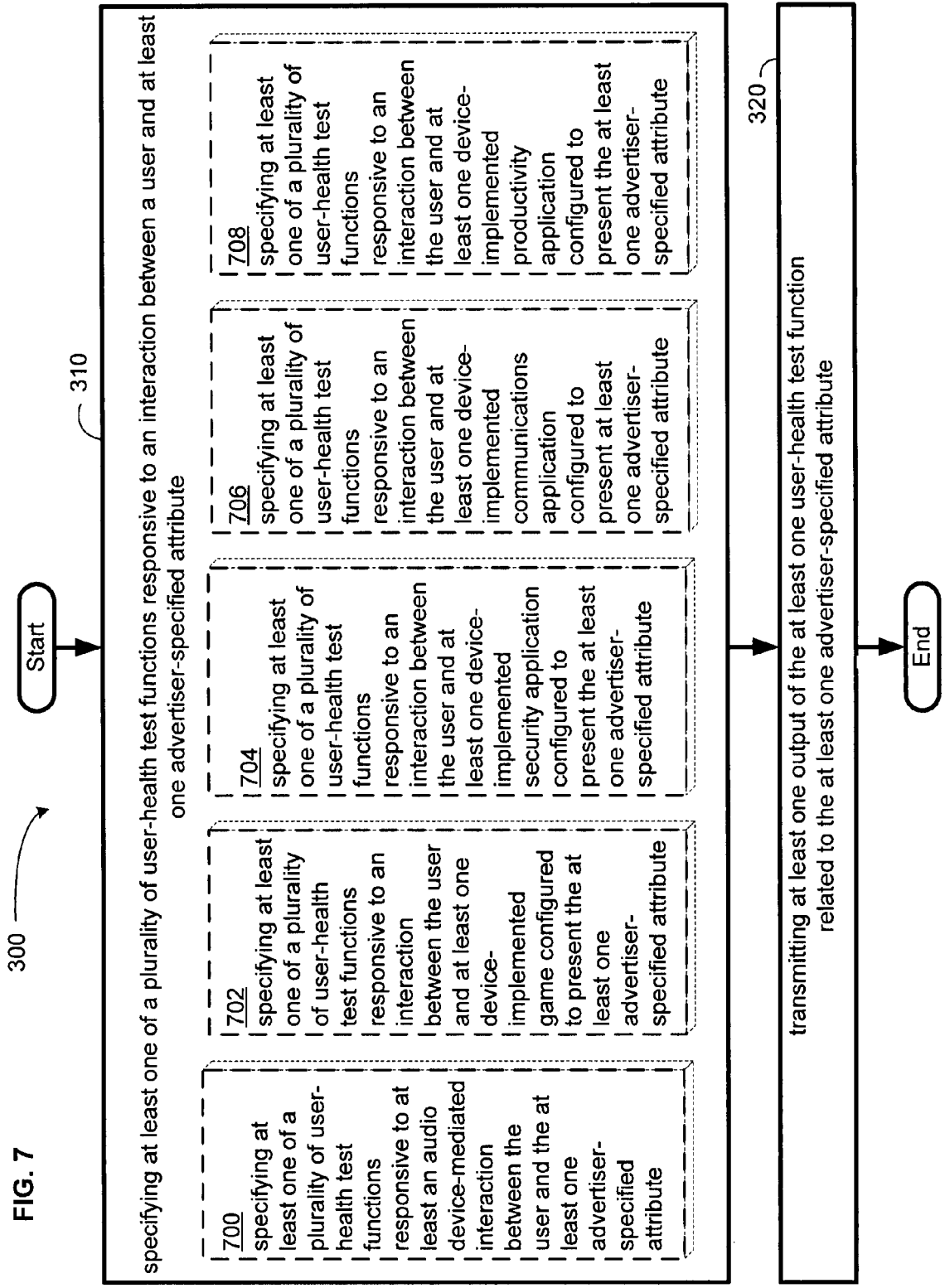

FIG. 7 illustrates an alternative embodiment of the example operational flow of FIG. 3.

Figure 8:
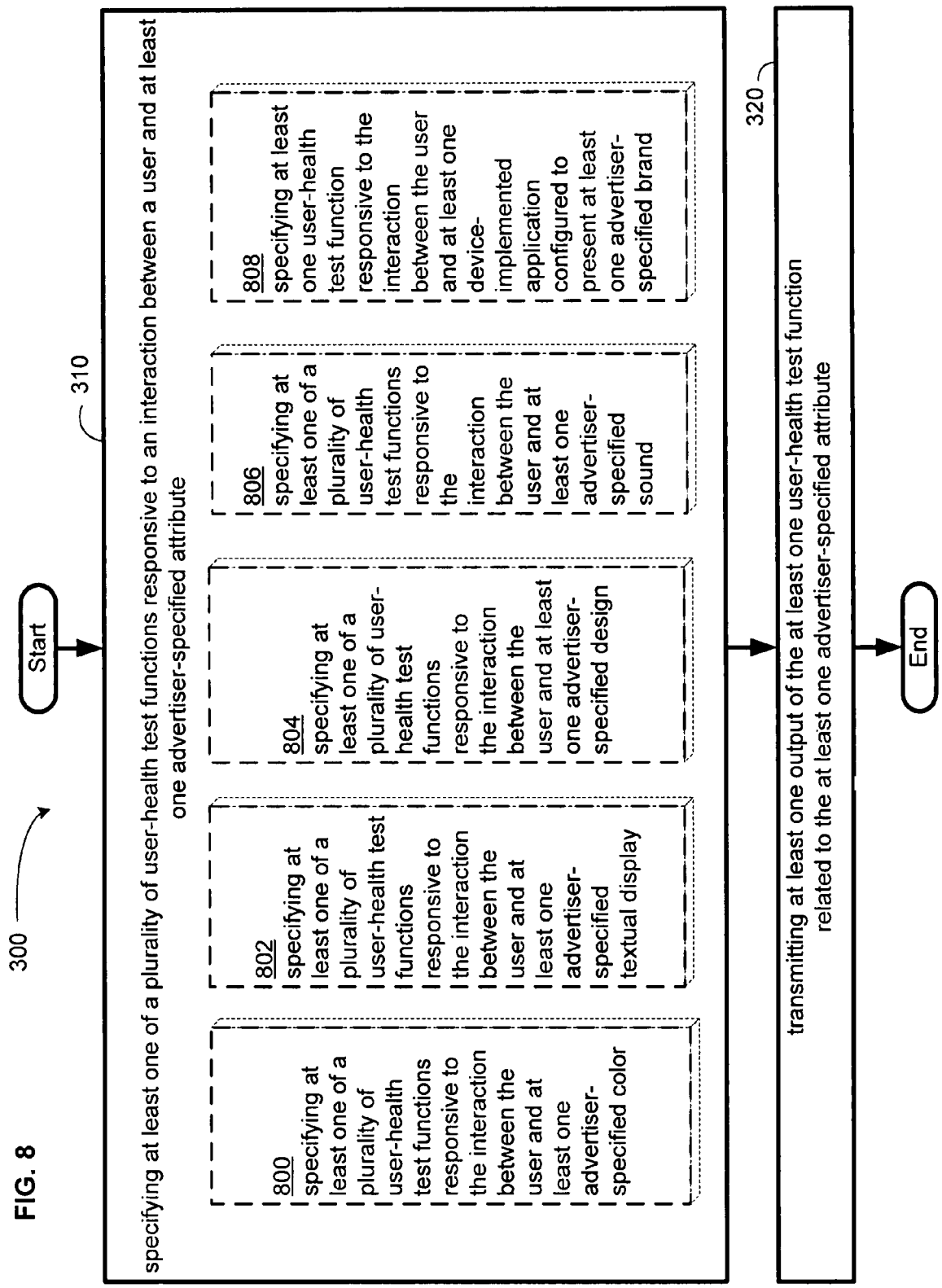

FIG. 8 illustrates an alternative embodiment of the example operational flow of FIG. 3.

Figure 9:
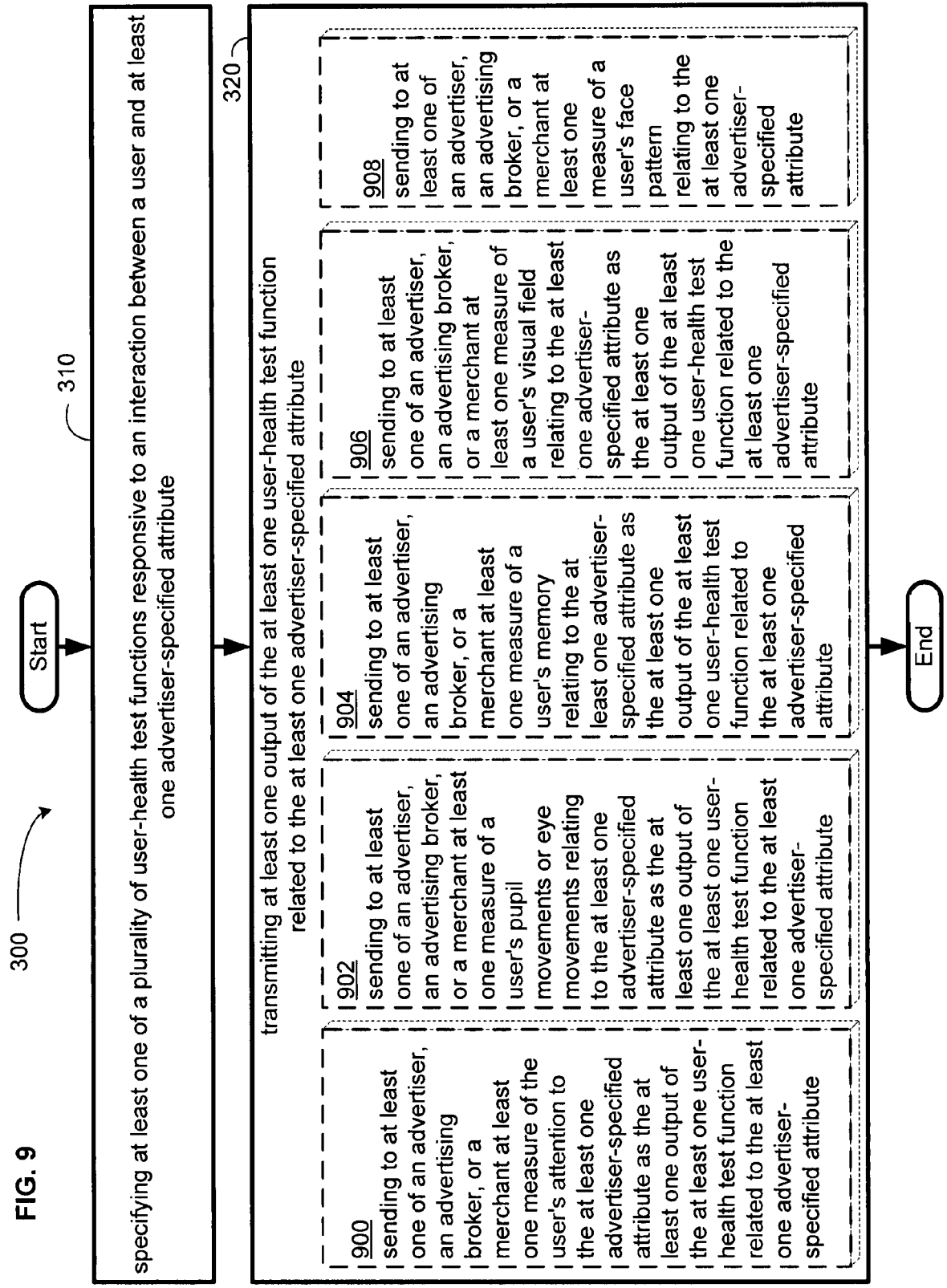

FIG. 9 illustrates an alternative embodiment of the example operational flow of FIG. 3.

Figure 10:
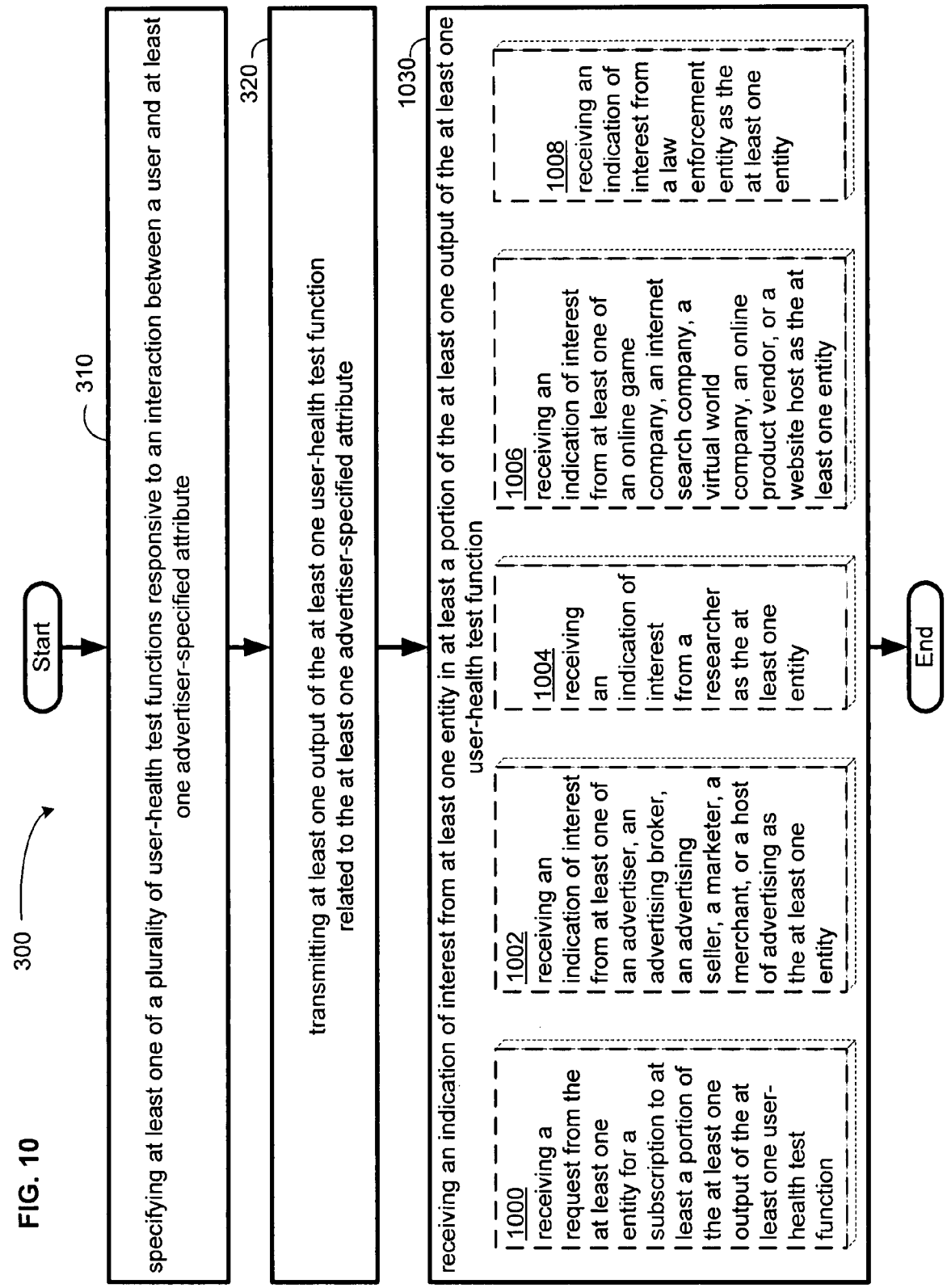

FIG. 10 illustrates an alternative embodiment of the example operational flow of FIG. 3.

Figure 11:
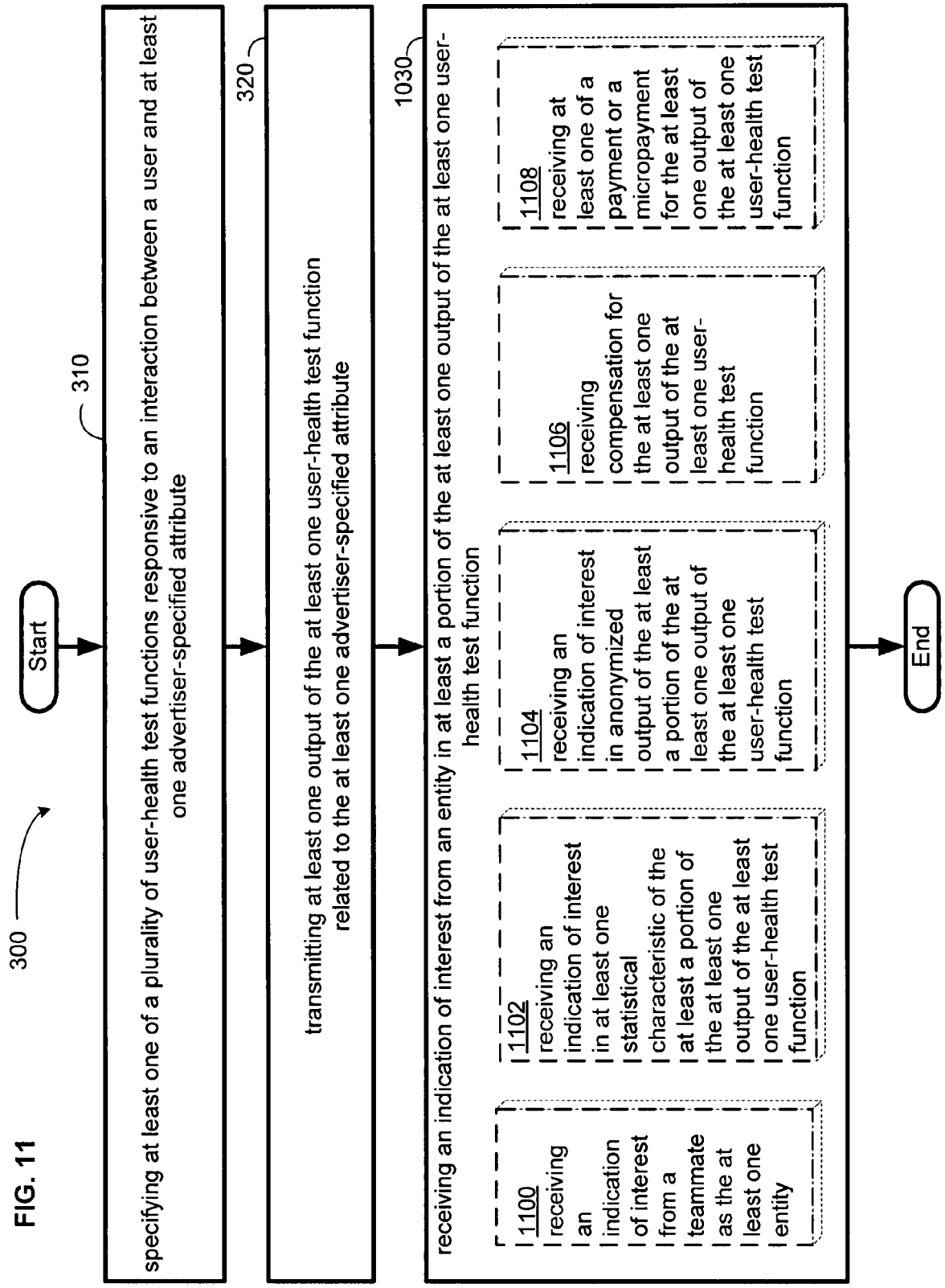

FIG. 11 illustrates an alternative embodiment of the example operational flow of FIG. 3.

Figure 12:
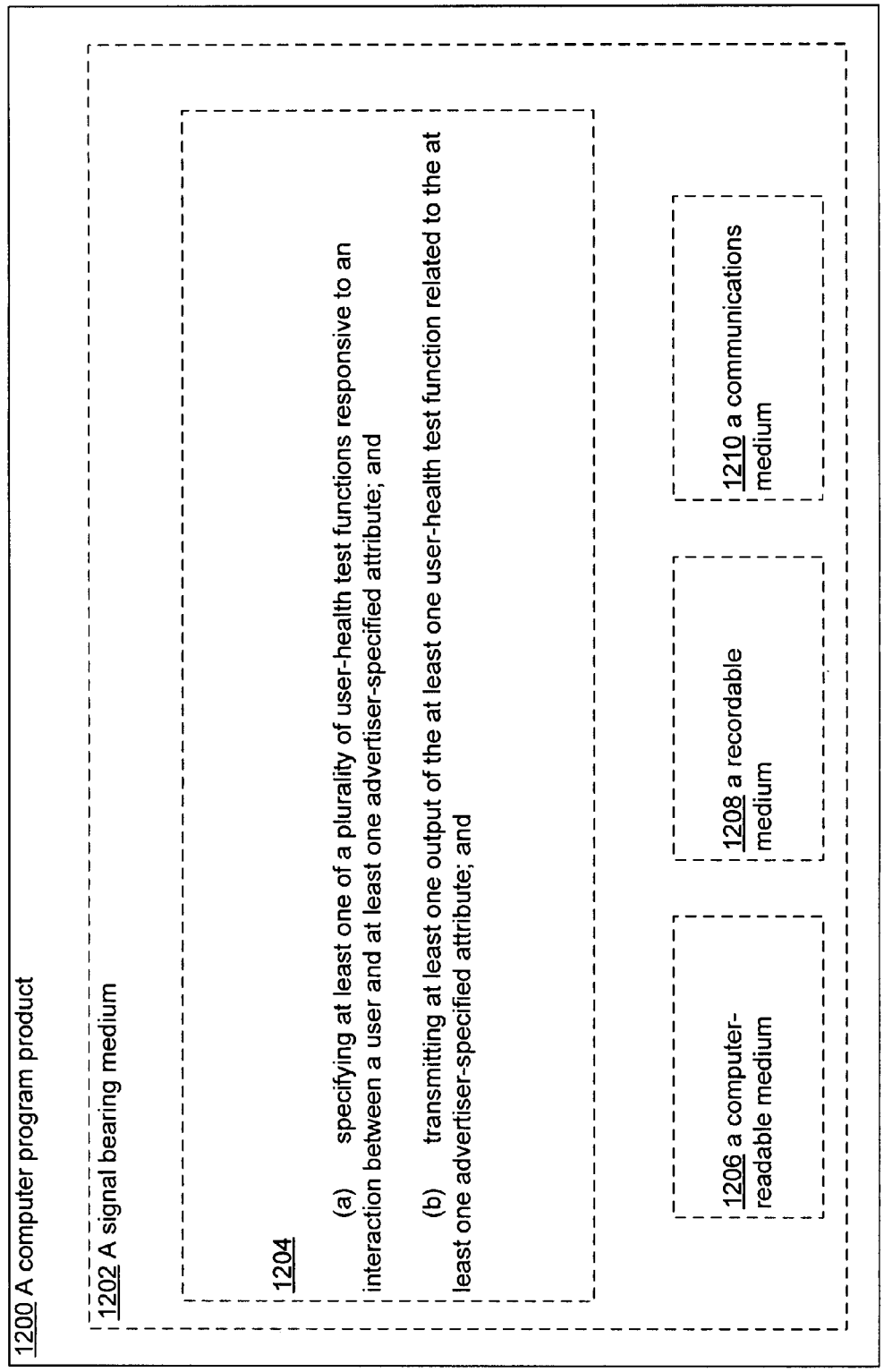

With reference now to FIG. 12, shown is a partial view of an example computer program product that includes a computer program for executing a computer process on a computing device related to computational user-health testing responsive to advertiser-configured content, which may serve as a context for introducing one or more processes and/or devices described herein.

With reference now to FIG. 13, shown is an example device in which embodiments may be implemented related to computational user-health testing responsive to advertiser-configured content, which may serve as a context for introducing one or more processes and/or devices described herein.

The use of the same symbols in different drawings typically indicates similar or identical items.

DETAILED DESCRIPTION

Figure 1:
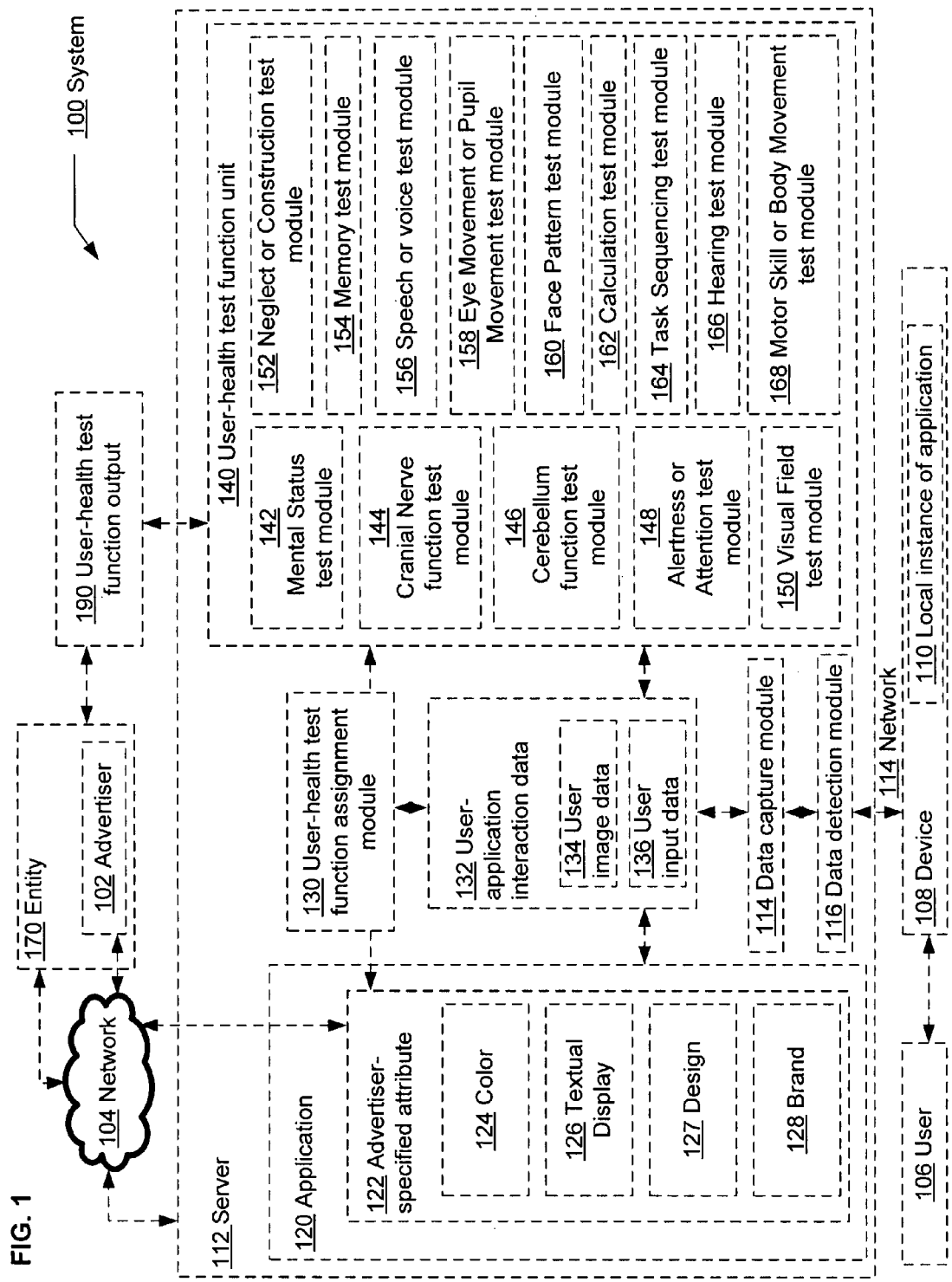

FIG. 1 illustrates an example system 100 in which embodiments may be implemented. The system 100 includes a device 108. The device 108 may contain, for example, a local instance of application 110. The device 108 may communicate over a network 1 14 with a server 112 having a user-health test function unit 140. User 106 may interact directly or through a user interface with local instance of application 110 or with application 120 directly. User interface 280, data detection module 116, and/or data capture module 114 may detect and/or capture user-application interaction data 132 based on an interaction between the user 106 and the local instance of application 110 and/or application 120. User-health test function unit 140 may detect actions and/or status of user 106 to generate user-health test function output 190. Device 108 and/or user-health test function unit 140 may send user-health test function output 190 to entity 170 and/or advertiser 102. Entity 170 may include, for example, an advertising broker, an advertiser, and/or a merchant.

In FIG. 1, an advertiser 102 may configure an application 120 to include an advertiser-specified attribute 122 such as a color 124, a textual display 126, a design 127, and/or a brand 128. A user-health test function assignment module 130 may detect user-application interaction data 132, and assign a user-health test function such as a memory test function carried out by memory analysis module 154. Such a memory test function may be triggered by the interaction of user 106 with advertiser-specified attribute 122.

In FIG. 1, the device 108 is illustrated as possibly being included within a system 100. Of course, virtually any kind of computing device may be used to implement the user-health test function unit 140, such as, for example, a workstation, a desktop computer, a networked computer, a server, a collection of servers and/or databases, a virtual machine running inside a computing device, a mobile computing device, or a tablet PC.

Additionally, not all of the user-health test function unit 140 need be implemented on a single computing device. For example, the user-health test function unit 140 and/or application 120 may be implemented and/or operable on a remote computer, while a user interface and/or local instance of application 110 are implemented and/or occur on a local computer. Further, aspects of the user-health test function unit 140 may be implemented in different combinations and implementations than that shown in FIG. 1. For example, functionality of a user interface may be incorporated into the user-health test function unit 140. The user-health test function unit 140 may perform simple data relay functions and/or complex data analysis, including, for example, fuzzy logic and/or traditional logic steps. Further, many methods of searching databases known in the art may be used, including, for example, unsupervised pattern discovery methods, coincidence detection methods, and/or entity relationship modeling. In some embodiments, the user-health test function unit 140 may process user-application interaction data 132 acquired according to health profiles available as updates through a network.

In FIG. 1, the user-health test function unit 140 is illustrated as including a user-health test function set including various user-health test function modules including, for example, a mental status test module 142, a cranial nerve function test module 144, a cerebellum function test module 146, an alertness or attention test module 148, a visual field test module 150, a neglect or construction test module 152, a memory test module 154, a speech or voice test module 156, an eye movement or pupil movement test module 158, a face pattern test module 160, a calculation test module 162, a task sequencing test module 164, a hearing test module 166, and/or a motor skill or body movement test module 168. Various user-application interaction data 132 may provide inputs for these user-health test functions, including user input data 136 such as personal information and/or other text data, passive user data such as user image data 134, user reaction time data, user speech or voice data, user hearing data, user body movement, eye movement, and/or pupil movement data, user face pattern data, user keystroke data, and/or user pointing device manipulation data.

The user-health function output 190 may be stored in virtually any type of memory that is able to store and/or provide access to information in, for example, a one-to-many, many-to-one, and/or many-to-many relationship. Such a memory may include, for example, a relational database and/or an object-oriented database, examples of which are provided in more detail herein.

Figure 2:
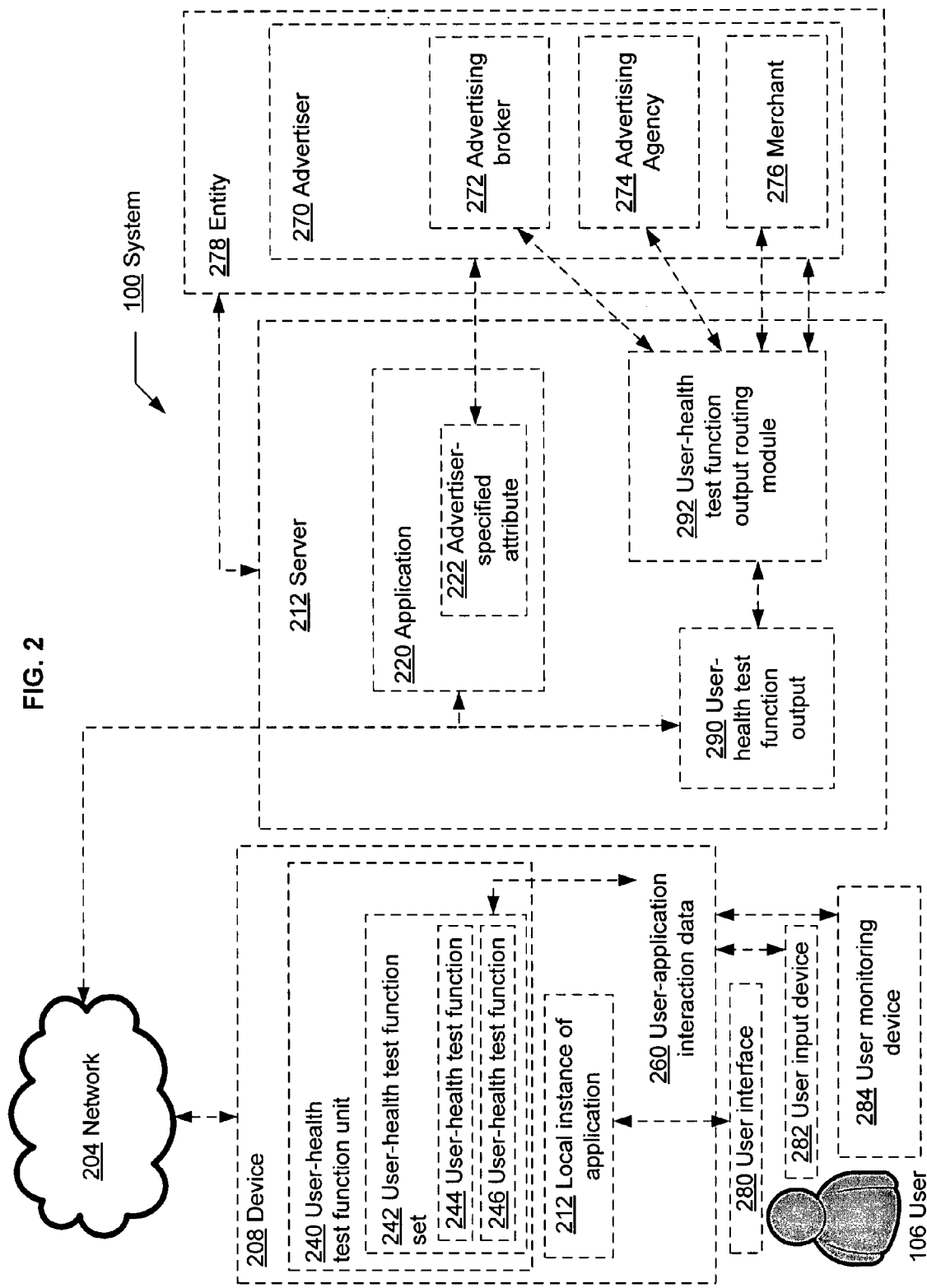
FIG. 2 illustrates certain alternative embodiments of the data capture and processing system of FIG. 1.

FIG. 2 illustrates certain alternative embodiments of the system 100 of FIG. 1. In FIG. 2, the user 106 may access the user interface 280 to interact with application 220 and/or a local instance of application 212 operable on the device 208. User-application interaction data 260 may be conveyed by user input device 282 and/or user monitoring device 284 to user-health test function unit 240 implemented on the device 208. The device 208 can communicate over a network 204 with application 220 including an advertiser-specified attribute 222. Advertiser 270 can configure the application 220 with the advertiser-specified attribute 222. The user-health test function unit 240 may send user-health test function output 290 from user-health test function 242 to server 212. User-health test function output routing module 292 can transmit user-health test function output 290 to advertiser 270, advertising broker 272, advertising agency 274, and/or merchant 276. Of course, it should be understood that there may be many users other than the specifically-illustrated user 106, for example, each with access to a local instance of application 212 including an advertiser specified attribute 222.

In this way, the user 106, who may be using a device that is connected through a network 204 with the system 100 (e.g., in an office, outdoors and/or in a public environment), may generate user-application interaction data 260 as if the user 106 were interacting locally with the server 212 on which the application 220 is locally operable.

As referenced herein, the user-health test function unit 140 and/or user-health test function output routing module 292 may be used to perform various data querying and/or recall techniques with respect to the user-application interaction data 132 and/or user-health test function output 190, in order to obtain and/or transmit user-health test function output 190. For example, where the user-application interaction data 132 is organized, keyed to, and/or otherwise accessible using one or more reference user-health test functions or profiles, user-health test function assignment module 130 may employ various Boolean, statistical, and/or semi-boolean searching techniques to match user-application interaction data 132 with one or more appropriate user-health test functions. Similarly, for example, where user-health test function output 190 is organized, keyed to, and/or otherwise accessible using one or more reference entity interest profiles, various Boolean, statistical, and/or semi-boolean searching techniques may be performed to match user-health test function output 190 with one or more appropriate entity 170.

Many examples of databases and database structures may be used in connection with the user-health test function unit 140 and/or user-health test function assignment module 130. Such examples include hierarchical models (in which data is organized in a tree and/or parent-child node structure), network models (based on set theory, and in which multi-parent structures per child node are supported), or object/relational models (combining the relational model with the object-oriented model).

Still other examples include various types of eXtensible Mark-up Language (XML) databases. For example, a database may be included that holds data in some format other than XML, but that is associated with an XML interface for accessing the database using XML. As another example, a database may store XML data directly. Additionally, or alternatively, virtually any semi-structured database may be used, so that context may be provided to/associated with stored data elements (either encoded with the data elements, or encoded externally to the data elements), so that data storage and/or access may be facilitated.

Such databases, and/or other memory storage techniques, may be written and/or implemented using various programming or coding languages. For example, object-oriented database management systems may be written in programming languages such as, for example, C++ or Java. Relational and/or object/relational models may make use of database languages, such as, for example, the structured query language (SQL), which may be used, for example, for interactive queries for information and/or for gathering and/or compiling data from the relational database(s).

For example, SQL or SQL-like operations over one or more reference health attribute may be performed, or Boolean operations using a reference health attribute may be performed. For example, weighted Boolean operations may be performed in which different weights or priorities are assigned to one or more of the reference health attributes, including reference health conditions, perhaps relative to one another. For example, a number-weighted, exclusive-OR operation may be performed to request specific weightings of desired (or undesired) health reference data to be included or excluded. Reference health attributes may include normal physiological values for such health-related things as reaction time, body or eye movement, memory, alertness, blood pressure, or the like. Such normal physiological values may be "normal" relative to the user 106, to a subpopulation to which the user 106 belongs, or to a general population.

FIG. 3 illustrates an operational flow 300 representing example operations related to computational user-health testing responsive to advertiser-configured content. In FIG. 3 and in following figures that include various examples of operational flows, discussion and explanation may be provided with respect to the above-described system environments of FIGS. 1-2, and/or with respect to other examples and contexts. However, it should be understood that the operational flows may be executed in a number of other environment and contexts, and/or in modified versions of FIGS. 1-2. Also, although the various operational flows are presented in the sequence(s) illustrated, it should be understood that the various operations may be performed in other orders than those which are illustrated, or may be performed concurrently.

After a start operation, operation 310 depicts specifying at least one of a plurality of user-health test functions responsive to an interaction between a user and at least one advertiser-specified attribute. For example, a user 106 can interact with an advertiser-specified attribute 122 within application 120 running on a device 108 or server 112. The advertiser-specified attribute 122 may be encountered during an interaction of the user 106 with local instance of application 110, to generate user-application interaction data 132. A user-health test function assignment module 130 can specify a user-health test function from within a user-health test function set 242 implemented on a server 112 or on a device 208 within a system 100. A user-health test function from within the user-health test function set 242 may be initiated by a user-health test function unit 240 resident on server 112 or on device 208. System 100 may also include application 120 operable on device 108 through network 114 as a local instance of application 110, including an advertiser-specified attribute 122. For example, a user-health test function such as a memory test function performed by memory test module 154 may be specified from within a user-health test function unit 140 residing on a personal computing device 108 or a remote server 112. A user-health test function unit 240 may communicates via a network 204, for example, with an application 220 or a local instance of application 212 including an advertiser-specified attribute 222. The at least one application 120 may reside on the at least one device 108, or the at least one application 120 may not reside on the at least one device 108 but instead it may be operable on the at least one device 108 from a server 112, for example, through a network 104 or other link. The user-health test assignment module 130 may detect user-application interaction data signifying an interaction between the user 106 and the advertiser-specified attribute 122. The user-health test assignment module 130 may then specify a user health test function operable to analyze the interaction of the user 106 with the advertiser-specified attribute. The advertiser-specified attribute may be, for example, an attribute of an object encountered by a user 106 during a gaming session, an emailing session, a word processing session, a code entry session, or the like.

For example, a data detection module 116 and/or data capture module 114 of the at least one device 108 or associated with the server 112 running application 120 may obtain user-application interaction data 132 in response to an interaction between the user 106 and the advertiser-specified attribute 122 associated with local instance of application 110 and/or application 120. User-health test function assignment module 130 and/or user-health test function unit 140 may then specify a user-health test function that is appropriate to analyze the user-application interaction data 132 for user-health measures or attributes, such as alertness, reaction time, memory, eye movement, clicking patterns, as discussed in more detail below. For example, the user-health test function unit 140 may specify an alertness or attention test function via alertness or attention test module 148 in response to user-application interaction data signaling proximity of a user's avatar to an in-game advertisement, for example. Such measurement of user-health data as described herein may be surreptitious, in which case user-awareness bias may be minimized.

It should be understood that user-health test functions may be profitably combined to provide particularly rich information in the form of user-health test function output. For example, user eye movement data may indicate a user interaction with an advertisement at a time when user heart rate data indicates an increase in alertness or excitedness. In another example, user pointing device data may indicate a user interaction with a particular segment of a virtual world that is coincident with a particular face pattern test function output and a particular speech or voice test function output. Together, these user-health test function outputs may provide a detailed portrait of a user's response to, for example, an advertisement.

Operation 320 depicts transmitting at least one output of the at least one user-health test function related to the at least one advertiser-specified attribute. A user-health test function output routing module 292 may be located either locally with respect to a device 208 or remotely, for example, associated with server 212. The user-health test function output routing module 292 may transmit user-health test function output 290 to an entity 170 or an advertiser 270. A user-health test function output routing module 292 may send a portion of user-health test function output 290 to advertiser 270, including, for example, advertising broker 272, advertising agency 274, and/or merchant 276 to obtain an indication of interest in the user-health test function output 316. For example, a user-health test function output routing module 292 may transmit to an entity 170 user-health test function output 290 in the form of user clicking frequency, user eye movement, and/or user memory with respect to an advertiser-specified attribute 222 encountered by the user 102 during a gaming session or internet searching session.

The subject matter disclosed herein may provide a number of useful services to interested entities. Firstly, user-health test function output may be a direct indicator of the effectiveness of an advertiser-specified attribute, for example, in terms of attracting a user's attention, persisting in a user's memory, and/or inducing purchases. Secondly, user-health test function output may aid an advertiser in discriminating between actual cognitive interest or disinterest in an advertiser-specified attribute and interest or disinterest in the advertiser-specified attribute that is a function of a user-health issue. For example, in a case where a user neglects an advertiser-specified attribute, user-health test function output may indicate a general deficiency in terms of a neglect or construction defect in the user, which may permit the advertiser to exclude that data point from a survey of the effectiveness of the advertiser-specified attribute in garnering attention from users. Thirdly, user-health test function output may provide entities with specific information about a user or users who are susceptible to, for example, a particular advertiser-specified attribute. Accordingly, it should be understood that a medical diagnosis is not required for user-health test function output to be of use or interest to an entity. In many cases, data that fall short of providing diagnostic clues may be transmitted to an entity, particularly where positive interaction data in the context of an advertiser-specified attribute are present.

For example, an alertness or attention test module 148 may send a summary or other analysis of user-application interaction data 132 relating to, for example, user eye movement during the interaction with the advertiser-specified attribute 122 as user-health test function output 190. Such user-health test function output 190 may be sent to an advertiser's computer connected by a network to server 112, device 108, or to at least one memory within server 112.

In this regard, it should be understood that a data signal may first be encoded and/or represented in digital form (i.e., as digital data), prior to the assignment to at least one memory. For example, a digitally-encoded representation of user eye movement data may be stored in a local memory, or may be transmitted for storage in a remote memory.

Thus, an operation may be performed relating either to a local or remote storage of the digital data, or to another type of transmission of the digital data. Of course, as discussed herein, operations also may be performed relating to accessing, querying, processing, recalling, or otherwise obtaining the digital data from a memory, including, for example, transmission of the digital data from a remote memory. Accordingly, such operation(s) may involve elements including at least an operator (e.g., either human or computer) directing the operation, a transmitting computer, and/or a receiving computer, and should be understood to occur within the United States as long as at least one of these elements resides in the United States.

FIG. 4 illustrates alternative embodiments of the example operational flow 300 of FIG. 3. FIG. 4 illustrates example embodiments where the specifying operation 310 may include at least one additional operation. Additional operations may include operation 400, 402, 404, 406, and/or operation 408.

Operation 400 depicts specifying at least one of a plurality of user-health test functions responsive to an interaction between a user and at least one device-implemented application configured to present the at least one advertiser-specified attribute. For example, a user-health test function assignment module 130 and/or user-health test function unit 140 may specify at least one of a plurality of user-health test functions responsive to an interaction between a user and at least one device-implemented application configured to present at least one advertiser-specified attribute. In one embodiment, a user-health test function assignment module 130 may activate an eye movement or pupil movement test module 158, initiating, for example, an eye movement test function to monitor user image data 134 during an interaction between a user 106 and a local instance of application 110 including an advertiser-specified attribute 122, the local instance of application 110 implemented on device 108. In another embodiment, user-health test function unit 240 can initiate, for example a mental status test module 142 within user-health test function set 242. A mental status test function thay then measure, for example, user alertness during an advertiser-specified video clip playing on web browser at user interface 280. A user-health test function 244 may be implemented in a personal computer of user 106; the user-health test function 244 may measure a physiological attribute during a user's interaction with a local instance of application 212 including an advertiser-specified attribute 222. For example, a physiological attribute such as heart rate, respiration, perspiration, temperature, skin coloring, pupil dilation, body or facial tic, or the like may be measured based on user-application interaction data 260 including user image data. Alternatively, a user-health test function 246 may be specified to measure a change in one or more physiological attributes of user 106, such as an increase in heart rate over a time interval as measured by a heart rate monitor, or a decreased ability of the user 106 to perform certain muscle movements as measured by an image capture device such as a video camera, or as measured by an electromyogram.

In another embodiment, a user-health test function assignment module 130 and/or user-health test function unit 140 may specify initiation of a visual field test module 150. The visual field test module 150 may include a visual field test function that can measure via user input data 136 the visual field of a user 106 during an interaction with an application 120 including an advertiser-specified attribute 122.

Operation 402 depicts specifying at least one alertness or attention test function responsive to the interaction between the user and the at least one advertiser-specified attribute. For example, a user-health test function assignment module 130 and/or user-health test function unit 140 may specify at least one alertness or attention test function responsive to the interaction between the user and the at least one advertiser-specified attribute. For example, a user-health test function assignment module 130 may activate an alertness or attention test module 148 within a mobile device 108 such as a videoconferencing device or cellular camera phone or videophone, the alertness or attention test function responsive to the interaction between a user 106 and an advertiser-specified attribute 122 encountered on the mobile device 108. Alternatively, a user-health test function unit 240 may specify user-health test function 246 such as a body movement test function from among user-health test function set 242. The user-health test function unit 240 may be programmed to activate the body movement test function during times of user interaction with, for example, an advertiser-specified attribute 222, such as a household item, such as a brand of food, musical work, or object on a website. Specification of user-health test function 246 may be based on user-application interaction data 260, which may be provided by user monitoring device 284 such as a security camera providing images of a user 106 interacting with a local environment during a programmed or random monitoring sweep. In an alternative embodiment, a user-health test function 244 operating in concert with a webcam may be specified by user-health test function unit 240 to capture one or more images of a user 106 at her personal computer while surfing the internet or gaming in the context of an advertiser-specified attribute 222.

Alertness or attention can be tested, for example, by measuring eye movements, body movements, pointing device manipulation, and/or task proficiency (e.g., are a user's eyelids drooping, is a user's head nodding, is a user failing or succeeding to activate on-screen items when prompted, does a user respond to a sound, or the like).

Alertness or attention to an advertisement may be gauged from a user's interaction with the advertisement. User-application interaction data 132 and/or user-health test function output 190 such as alertness or attention test module 148 output may demonstrate user interest in the advertisement in the form of face pattern data (e.g., a smile on an image of the user's face), pointing device manipulation data (e.g., a mouse click on an onscreen advertisement icon), and/or eye movements data (e.g., repeated eye movements toward the advertisement), or the like.

Alertness or attention user attributes are indicators of a user's mental status. An example of an alertness test function may be a measure of reaction time as one objective manifestation. Examples of attention test functions may include ability to focus on simple tasks, ability to spell the word "world" forward and backward, or reciting a numerical sequence forward and backward as objective manifestations of an alertness problem. An alertness or attention test module 418 and/or user-health test function unit 140 may require a user to enter a password backward as an alertness test function. Alternatively, a user may be prompted to perform an executive function as a predicate to launching an application such as a word processing program. For example, an alertness test function could be activated by a user command to open a word processing program, requiring performance of, for example, a spelling task as a preliminary step in launching the word processing program. Also, writing ability may be tested by requiring the user to write their name or write a sentence on a device, perhaps with a stylus on a touchscreen.

Reduced level of alertness or attention can indicate the following possible conditions where an acute reduction in alertness or attention is detected: stroke involving the reticular activating system, stroke involving the bilateral or unilateral thalamus, metabolic abnormalities such as hyper or hypoglycemia, toxic effects due to substance overdose (for example, benzodiazepines, or other toxins such as alcohol). Reduced level of alertness and attention can indicate the following possible conditions where a subacute or chronic reduction in alertness or attention is detected: dementia (caused by, for example, Alzheimer's disease, vascular dementia, Parkinson's disease, Huntingdon's disease, Creutzfeldt-Jakob disease, Pick disease, head injury, infection, normal pressure hydrocephalus, brain tumor, exposure to toxin (for example, lead or other heavy metals), metabolic disorders, hormone disorders, hypoxia, drug reactions, drug overuse, drug abuse, encephalitis (caused by, for example, enteroviruses, herpes viruses, or arboviruses), or mood disorders (for example, bipolar disorder, cyclothymic disorder, depression, depressive disorder NOS (not otherwise specified), dysthymic disorder, postpartum depression, or seasonal affective disorder)).

In the context of the above alertness or attention test function, as set forth herein available data arising from the user-health test function are one or more of various types of user-application interaction data 132 described herein. Altered alertness or attention function may indicate certain of the possible conditions discussed above. One skilled in the art can establish or determine parameters or values relating to the one or more types of user data indicative of altered alertness or attention function, or the one or more types of user data indicative of a likely condition associated with altered alertness or attention function. Parameters or values can be set by one skilled in the art based on knowledge, direct experience, or using available resources such as websites, textbooks, journal articles, or the like. An example of a relevant website can be found in the online Merck Manual at http://www.merck-.com/mmhe/sec06/ch077/ch077c.html#tb077_1. Examples of relevant textbooks include Patten, J. P., "Neurological Differential Diagnosis," Second Ed., Springer-Verlag, London, 2005; Kasper, Braunwald, Fauci, Hauser, Longo, and Jameson, "Harrison's Principles of Internal Medicine," 16th Ed., McGraw-Hill, New York, 2005; Greenberg, M. S., "Handbook of Neurosurgery," 6th Ed., Thieme, Lakeland, 2006; and Victor, M., and Ropper, A. H., "Adams and Victor's Principles of Neurology," 7th Ed., McGraw-Hill, New York, 2001.

Operation 404 depicts specifying at least one memory test function responsive to the interaction between the user and the at least one advertiser-specified attribute. For example, a user-health test function unit 140 and/or user-health test function assignment module 130 may specify at least one memory test function responsive to the interaction between the user and the at least one advertiser-specified attribute. A specified memory test module 154 may respond to user-application interaction data 132 via data detection module 116, data capture module 114, and/or user input data 136 indicating an interaction between the user and at least one advertiser-specified attribute 122.

Memory can be tested, for example, by measuring keyboard entry data, pointing device manipulation, and/or task proficiency (e.g., can a user type a word correctly after a time interval to indicate brand awareness, can a user match a sound to an item after a time interval, or the like).

Memory in the context of an advertisement may be gauged from a user's interaction with the advertisement. User-application interaction data 132 and/or output from memory test module 154 may demonstrate user interest in the advertisement in the form of repeated attention to an item over time (e.g., repeated eye movements toward the advertisement, repeated clicks on an advertisement over time, success at brand recognition challenges, or the like).

A user's memory attributes are indicators of a user's mental status. An example of a memory test function may be a measure of a user's short-term ability to recall items presented, for example, in a story, or after a short period of time. Another example of a memory test function may be a measure of a user's long-term memory, for example their ability to remember basic personal information such as birthdays, place of birth, or names of relatives. Another example of a memory test function may be a memory test module 154 and/or user-health test function unit 140 prompting a user to change and/or enter a password with a specified frequency during internet browser use. A memory test function involving changes to a password that is required to access an internet server can challenge a user's memory according to a fixed or variable schedule. A memory test function can test a user's ability to recall an advertiser-specified attribute 122 such as a phrase, jingle, product design, packaging, brand logo, or the like.

Difficulty with recall after about 1 to 5 minutes may indicate damage to the limbic memory structures located in the medial temporal lobes and medial diencephalon of the brain, or damage to the fornix. Dysfunction of these structures characteristically causes anterograde amnesia, meaning difficulty remembering new facts and events occurring after lesion onset. Reduced short-term memory function can also indicate the following conditions: head injury, Alzheimer's disease, Herpes virus infection, seizure, emotional shock or hysteria, alcohol-related brain damage, barbiturate or heroin use, general anaesthetic effects, electroconvulsive therapy effects, stroke, transient ischemic attack (i.e., a "mini-stroke"), complication of brain surgery. Reduced long-term memory function can indicate the following conditions: Alzheimer's disease, alcohol-related brain damage, complication of brain surgery, depressive pseudodementia, adverse drug reactions (e.g., to benzodiazepines, anti-ulcer drugs, analgesics, anti-hypertensives, diabetes drugs, beta-blockers, anti-Parkinson's disease drugs, anti-emetics, anti-psychotics, or certain drug combinations, such as haloperidol and methyldopa combination therapy), multi-infarct dementia, or head injury.

In the context of the above memory test function, as set forth herein available data arising from the user-health test function are one or more of various types of user-application interaction data 132 described herein. Altered memory function may indicate certain of the possible conditions discussed above. One skilled in the art can establish or determine parameters or values relating to the one or more types of user data indicative of altered memory function, or the one or more types of user data indicative of a likely condition associated with altered memory function. Parameters or values can be set by one skilled in the art based on knowledge, direct experience, or using available resources such as websites, textbooks, journal articles, or the like. An example of a relevant website can be found in the online Merck Manual at http://www.merck.com/mmhe/sec06/ch077/ch077c.html#tb077_1. Examples of relevant textbooks include Patten, J. P., "Neurological Differential Diagnosis," Second Ed., Springer-Verlag, London, 2005; Kasper, Braunwald, Fauci, Hauser, Longo, and Jameson, "Harrison's Principles of Internal Medicine," 16th Ed., McGraw-Hill, New York, 2005; Greenberg, M. S., "Handbook of Neurosurgery," 6th Ed., Thieme, Lakeland, 2006; and Victor, M., and Ropper, A. H., "Adams and Victor's Principles of Neurology," 7th Ed., McGraw-Hill, New York, 2001.

Operation 406 depicts specifying at least one speech or voice test function responsive to the interaction between the user and the at least one advertiser-specified attribute. For example, a user-health test function unit 140 and/or user-health test function assignment module 130 may specify at least one speech or voice test function responsive to the interaction between the user and the at least one advertiser-specified attribute. A specified speech or voice test module 156 may respond to user-application interaction data 132 via data detection module 116, data capture module 114, and/or user input data 136 indicating an interaction between the user and at least one advertiser-specified attribute 122.

Speech can be tested, for example, by measuring voice, song, and/or other vocal utterances of a user (e.g., can a user say the words on a screen, does an advertising slogan come easily to a user's lips, is a jingle catchy such that a user sings it after hearing it, does a user respond out loud to an advertisement, or the like).

Speech responses to an advertiser-specified attribute 122 such as a jingle, slogan, or design may be gauged from a user's interaction with the advertiser-specified attribute 122. User-application interaction data 132 may demonstrate user interest in the advertiser-specified attribute 122 in the form of speech data (e.g., sounds including words uttered relating to the advertisement), or the like.

User speech attributes are indicators of a user's mental status. An example of a speech test function may be a measure of a user's fluency or ability to produce spontaneous speech, including phrase length, rate of speech, abundance of spontaneous speech, tonal modulation, or whether paraphasic errors (e.g., inappropriately substituted words or syllables), neologisms (e.g., nonexistent words), or errors in grammar are present. Another example of a speech test function is a program that can measure the number of words spoken by a user during a video conference. The number of words per interaction or per unit time could be measured. A marked decrease in the number of words spoken could indicate a speech problem.

Another example of a speech test function may be a measure of a user's comprehension of spoken language, including whether a user 106 can understand simple questions and commands, or grammatical structure. For example, a user 106 could be tested by a speech or voice test module 156 and/or user-health test function unit 140 asking the question "Mike was shot by John. Is John dead?" An inappropriate response may indicate a speech center defect. Alternatively a user-health test function unit 140 and/or speech or voice test module 156 may require a user to say a slogan, jingle, code, or phrase and repeat it several times. Speech defects may become apparent if the user has difficulty repeating the slogan, jingle, code, or phrase during, for example, a videoconference session, or while using speech recognition software.

Another example of a speech test function may be a measure of a user's ability to name simple everyday objects, perhaps with advertiser-specified attributes (e.g., a Bic® pen, a Rolex® watch, or a McDonald's® restaurant) and also more difficult objects (e.g., Hermes® scarf, Louis Vuitton® bag, or Les Paul® guitar). A speech test function may, for example, require the naming of an object prior to or during the interaction of a user 106 with an application 120, as a time-based or event-based checkpoint. For example, a user 106 may be prompted by the user-health test function unit 140 and/or the speech or voice test module 156 to say "Crest" after being shown a picture of a tube of Crest® toothpaste, prior to or during the user's interaction with, for example, a word processing or email program. A test requiring the naming of parts of objects is often more difficult for users with speech comprehension impairment. Another speech test gauges a user's ability to repeat single words and sentences (e.g., "no if's and's or but's"). A further example of a speech test measures a user's ability to read single words, a brief written passage, or the front page of the newspaper aloud followed by a test for comprehension.

Difficulty with speech or reading/writing ability may indicate, for example, lesions in the dominant (usually left) frontal lobe, including Broca's area (output area); the left temporal and parietal lobes, including Wernicke's area (input area); subcortical white matter and gray matter structures, including thalamus and caudate nucleus; as well as the non-dominant hemisphere. Typical diagnostic conditions may include, for example, stroke, head trauma, dementia, multiple sclerosis, Parkinson's disease, Landau-Kleffner syndrome (a rare syndrome of acquired epileptic aphasia).

A user's voice can be tested, for example, by measuring a user's reaction to audio or visual content, perhaps by way of an exclamation, speech, or other vocal utterance acknowledging that a sound was heard by the user or that a visual element was seen and recognized in some way. User voice information may be of interest to an advertising entity, for example, where a user 106 exhibits some reaction with respect to an advertisement, for example, in a computerized game world or in another virtual world. In one embodiment, a user's reaction to an advertisement may be an exclamation such as "Wow, that's nice!" that may be detectable by a microphone monitoring an interaction between the user and a merchant's product web page. Information from the user-application interaction data 132 may suggest that a user has certain likes and dislikes among listed products on a webpage, or among various advertisements; this information may be of interest to a merchant and/or advertiser. Accordingly, user vocal reaction data may comprise the user-health test function output 190.

Voice may be measured relative to a user's interaction with an application 220. User-application interaction data 260 may demonstrate user interest in an advertisement displayed in the context of application 220 in the form of vocalizations uttered in the context of viewing or otherwise interacting with the advertisement (e.g., rotating an image on a webpage to examine different views of the object, playing a game within an advertisement, or the like). A speech recognition function such as a software program or computational device may be able to identify and/or record an utterance of a user as speech or voice test module 156 output.

User voice data may or may not be distinguishable from user lack of interest, or such data may be unrelated to an application visual object or sound, or to a user-health test function object or sound. In any case, an entity 170 may be interested in the output of a voice test module 438. In cases where a neurological condition underlies a specific voice attribute or behavior such as an apparent voice deficit, an entity may be interested in this information. For example, data from an individual exhibiting failure to react vocally to a sound or visual cue in a virtual world due to a neurological condition may be excluded from a survey by the entity receiving the data. Alternatively, for example, data about the voice ability of a user including speaking habits relative to advertisements may be of interest to an entity in terms of identifying positive, negative or lack of responses to specific advertising.

An example of a voice test function may be a measure of symmetrical elevation of the palate when the user says "aah," or a test of the gag reflex. In an ipsilateral lesion of the vagus nerve, the uvula deviates towards the affected side. As a result of its innervation (through the recurrent laryngeal nerve) to the vocal cords, hoarseness may develop as a symptom of vagus nerve injury. A voice test module 138 and/or user-health test function unit 140 may monitor user voice frequency or volume data during, for example, gaming, videoconferencing, speech recognition software use, or mobile phone use. Injury to the recurrent laryngeal nerve can occur with lesions in the neck or apical chest. The most common lesions are tumors in the neck or apical chest. Cancers may include lung cancer, esophageal cancer, or squamous cell cancer.

Other voice test functions may involve first observing the tongue (while in floor of mouth) for fasciculations. If present, fasciculations may indicate peripheral hypoglossal nerve dysfunction. Next, the user may be prompted to protrude the tongue and move it in all directions. When protruded, the tongue will deviate toward the side of a lesion (as the unaffected muscles push the tongue more than the weaker side). Gross symptoms of pathology may result in garbled sound in speech (as if there were marbles in the user's mouth). Damage to the hypoglossal nerve affecting voice/speech may indicate neoplasm, aneurysm, or other external compression, and may result in protrusion of the tongue away from side of the lesion for an upper motor neuron process and toward the side of the lesion for a lower motor neuron process. Accordingly, a voice test module 438 and/or user-health test function unit 140 may assess a user's ability to make simple sounds or to say words, for example, consistently with an established voice pattern for the user.

In the context of the above speech or voice test function, as set forth herein available data arising from the user-health test function are one or more of various types of user-application interaction data 132 described herein. Altered speech or voice function may indicate certain of the possible conditions discussed above. One skilled in the art can establish or determine parameters or values relating to the one or more types of user data indicative of altered speech or voice function, or the one or more types of user data indicative of a likely condition associated with altered speech or voice function. Parameters or values can be set by one skilled in the art based on knowledge, direct experience, or using available resources such as websites, textbooks, journal articles, or the like. An example of a relevant website can be found in the online Merck Manual at http://www.merck.com/mmhe/sec06/ch077/ch077c.html#tb077_1. Examples of relevant textbooks include Patten, J. P., "Neurological Differential Diagnosis," Second Ed., Springer-Verlag, London, 2005; Kasper, Braunwald, Fauci, Hauser, Longo, and Jameson, "Harrison's Principles of Internal Medicine," 16th Ed., McGraw-Hill, New York, 2005; Greenberg, M. S., "Handbook of Neurosurgery," 6th Ed., Thieme, Lakeland, 2006; and Victor, M., and Ropper, A. H., "Adams and Victor's Principles of Neurology," 7th Ed., McGraw-Hill, New York, 2001.

Operation 408 depicts specifying at least one calculation test function responsive to the interaction between the user and the at least one advertiser-specified attribute. For example, a user-health test function unit 140 and/or user-health test function assignment module 130 may specify at least one calculation test function responsive to the interaction between the user and the at least one advertiser-specified attribute 122. A specified calculation test module 162 may respond to user-application interaction data 132 via data detection module 116, data capture module 114, and/or user input data 136 indicating an interaction between the user and at least one advertiser-specified attribute 122.

Calculation ability of a user may be tested by arithmetic challenges associated with an application 220. A calculation test module 162 may include logic puzzles such as sudoku. High-functioning users may voluntarily select a calculation test function associated with an advertiser-specified attribute such as an advertising puzzle widget on a webpage. For example, a user-health test function unit 140 and/or user-health test function assignment module 130 may specify a calculation test module 162 to guage a user's interest in an advertiser-sponsored sudoku widget on a website. User-health test function output 190 from such a user-health test function may be of interest, for example, to a website host hoping to attract users with interest in sudoku, logic puzzles, or the like.

A user's calculation attributes are indicators of a user's mental status. An example of a calculation test function may be a measure of a user's ability to do simple math such as addition or subtraction, for example. A calculation test module 162 and/or user-health test function unit 140 may prompt a user 106 to solve an arithmetic problem in the context of interacting with application 120, or alternatively, in the context of using the device in between periods of interacting with the application 120. For example, a user may be prompted to enter the number of items associated with an advertiser-specified attribute and/or gold pieces collected during a segment of gameplay in the context of playing a game.

In this and other contexts, user interaction with a device's operating system or other system function may also constitute user interaction with an application 120. Difficulty in completing calculation tests may be indicative of stroke (e.g., embolic, thrombotic, or due to vasculitis), dominant parietal lesion, or brain tumor (e.g., glioma or meningioma). When a calculation ability deficiency is found with defects in user ability to distinguish right and left body parts (right-left confusion), ability to name and identify each finger (finger agnosia), and ability to write their name and a sentence, Gerstman's syndrome, a lesion in the dominant parietal lobe of the brain, may be present.

In the context of the above calculation test function, as set forth herein available data arising from the user-health test function are one or more of various types of user-application interaction data 132 described herein. Altered calculation function may indicate certain of the possible conditions discussed above. One skilled in the art can establish or determine parameters or values relating to the one or more types of user data indicative of altered calculation function, or the one or more types of user data indicative of a likely condition associated with altered calculation function. Parameters or values can be set by one skilled in the art based on knowledge, direct experience, or using available resources such as websites, textbooks, journal articles, or the like. An example of a relevant website can be found in the online Merck Manual at http://www.merck.com/mmhe/sec06/ch077/ch077c.html#tb077_1. Examples of relevant textbooks include Patten, J. P., "Neurological Differential Diagnosis," Second Ed., Springer-Verlag, London, 2005; Kasper, Braunwald, Fauci, Hauser, Longo, and Jameson, "Harrison's Principles of Internal Medicine," 16th Ed., McGraw-Hill, New York, 2005; Greenberg, M. S., "Handbook of Neurosurgery," 6th Ed., Thieme, Lakeland, 2006; and Victor, M., and Ropper, A. H., "Adams and Victor's Principles of Neurology," 7th Ed., McGraw-Hill, New York, 2001.

FIG. 5 illustrates alternative embodiments of the example operational flow 300 of FIG. 3. FIG. 5 illustrates example embodiments where the specifying operation 310 may include at least one additional operation. Additional operations may include operation 500, 502, 504, 506, and/or operation 508.

Operation 500 depicts specifying at least one neglect or construction test function responsive to the interaction between the user and the at least one advertiser-specified attribute. For example, a user-health test function unit 140 and/or user-health test function assignment module 130 may specify at least one neglect or construction test function responsive to the interaction between the user and the at least one advertiser-specified attribute 122. A specified neglect or construction test module 152 may respond to user-application interaction data 132 via data detection module 116, data capture module 114, user image data 134, and/or user input data 136 indicating an interaction between the user and at least one advertiser-specified attribute 122.

Neglect or construction can be tested, for example, by measuring user actions with respect to items on a display including the ability of the user to acknowledge items by cursor movement, clicking, voice, eye movement, or other ways of focusing on an item, including an item with an advertiser-specified attribute.

Neglectful responses to an advertiser-specified attribute 122, for example, may be gauged from a user's interaction with the advertiser-specified attribute 122. User-application interaction data 132 may demonstrate user interest in the advertiser-specified attribute 122 in the form of direct attention to the advertiser-specified attribute 122 in terms of pointing device manipulation (e.g., pointing and/or clicking), sounds (e.g., words uttered relating to the advertisement), eye movement, or the like. User neglect or construction deficits may or may not be distinguishable from user lack of interest. In either case, an advertiser or other entity may be interested in the output of a neglect or construction test function. In cases where a neurological condition underlies a neglect or construction deficit behavior, an entity may be particularly interested in this information. For example, data from an individual exhibiting neglect due to a neurological condition may be excluded from a survey by an entity. Alternatively, for example, data about the behavior of a user 106 with a construction deficit relative to an advertiser-specified attribute 122 may be of interest to an entity in terms of identifying characteristics of users with positive or negative responses to a specific advertiser-specified attribute 122.

Neglect or construction user attributes are indicators of a user's mental status. Neglect may include a neurological condition involving a deficit in attention to an area of space, often one side of the body or the other. A construction defect may include a deficit in a user's ability to draw complex figures or manipulate blocks or other objects in space as a result of neglect or other visuospatial impairment.

Hemineglect may include an abnormality in attention to one side of the universe that is not due to a primary sensory or motor disturbance. In sensory neglect, users ignore visual, somatosensory, or auditory stimuli on the affected side, despite intact primary sensation. This can often be demonstrated by testing for extinction on double simultaneous stimulation. Thus, a neglect or construction test module 152 and/or user-health test function unit 140 may present a stimulus on one or both sides of a display for a user 106 to click on. A user 106 with hemineglect may detect the stimulus on the affected side when presented alone, but when stimuli are presented simultaneously on both sides, only the stimulus on the unaffected side may be detected. In motor neglect, normal strength may be present, however, the user 106 often does not move the affected limb unless attention is strongly directed toward it.

An example of a neglect test function may be a measure of a user's awareness of events occurring on one side of the user or the other. A user 106 could be asked, "Do you see anything on the left side of the screen?" Users with anosognosia (i.e., unawareness of a disability) may be strikingly unaware of severe deficits on the affected side. For example, some people with acute stroke who are completely paralyzed on the left side believe there is nothing wrong and may even be perplexed about why they are in the hospital. Alternatively, a neglect or construction test module 152 and/or user-health test function unit 140 may present a drawing task to a user in the context of an application 120 that involves similar activities. A construction test involves prompting a user to draw complex figures or to manipulate objects in space. Difficulty in completing such a test may be a result of neglect or other visuospatial impairment.

Another neglect test function is a test of a user's ability to acknowledge a series of objects on a display that span a center point on the display. For example, a user may be prompted to click on each of 5 advertiser-specified attributes 122 present in a horizontal line across the midline of a display. If the user has a neglect problem, she may only detect and accordingly click on the advertiser-specified attributes 122 on one side of the display, neglecting the others.

Hemineglect is most common in lesions of the right (non-dominant) parietal lobe, causing users to neglect the left side. Left-sided neglect can also occasionally be seen in right frontal lesions, right thalamic or basal ganglia lesions, and, rarely, in lesions of the right midbrain. Hemineglect or difficulty with construction tasks may be indicative of stroke (e.g., embolic, thrombotic, or due to vasculitis), or brain tumor (e.g., glioma or meningioma).

In the context of the above neglect or construction test function, as set forth herein available data arising from the user-health test function are one or more of various types of user-application interaction data 132 described herein. Altered neglect or construction function may indicate certain of the possible conditions discussed above. One skilled in the art can establish or determine parameters or values relating to the one or more types of user data indicative of altered neglect or construction function, or the one or more types of user data indicative of a likely condition associated with altered neglect or construction function. Parameters or values can be set by one skilled in the art based on knowledge, direct experience, or using available resources such as websites, textbooks, journal articles, or the like. An example of a relevant website can be found in the online Merck Manual at http://www.merck-.com/mmhe/sec06/ch077/ch077c.html#tb077_1. Examples of relevant textbooks include Patten, J. P., "Neurological Differential Diagnosis," Second Ed., Springer-Verlag, London, 2005; Kasper, Braunwald, Fauci, Hauser, Longo, and Jameson, "Harrison's Principles of Internal Medicine," 16$^{th}$ Ed., McGraw-Hill, New York, 2005; Greenberg, M. S., "Handbook of Neurosurgery," 6$^{th}$ Ed., Thieme, Lakeland, 2006; and Victor, M., and Ropper, A. H., "Adams and Victor's Principles of Neurology," 7$^{th}$ Ed., McGraw-Hill, New York, 2001.

Operation 502 depicts specifying at least one task sequencing test function responsive to the interaction between the user and the at least one advertiser-specified attribute. For example, a user-health test function unit 140 and/or user-health test function assignment module 130 may specify at least one task sequencing test function responsive to the interaction between the user and the at least one advertiser-specified attribute 122. A specified task sequencing test module 164 may respond to user-application interaction data 132 via data detection module 116, data capture module 114, user image data 134, and/or user input data 136 indicating an interaction between the user and at least one advertiser-specified attribute 122.

Task sequencing can be tested, for example, by measuring user actions with respect to items on a display including the ability of the user to acknowledge items in sequence via cursor movement, clicking, voice, eye movement, or other ways of, for example, selecting or otherwise manipulating items or performing tasks over time.

Task sequencing information may be of interest to an advertising entity, for example, where a sequence of user actions on a web page comprise user-health test function output 190, e.g., output of task sequencing test module 164. For example, an entity such as an advertiser may be interested in eye movements as a function of time. For example, how much time passes before a user's eyes contact an advertiser-specified attribute 122 on the web page and/or how long before the user's eyes move away from the advertiser-specified attribute 122? Does the user click on the advertiser-specified attribute? Does a user 106 close an advertisement window quickly, for example, or is there an indication that the user 106 reads the advertiser-specified attribute 122, e.g., the text in the advertisement window? Task sequencing function may be gauged from a user's interaction with the application 220. User-application interaction data 260 may demonstrate user interest in the advertiser-specified attribute 222 in the form of compound actions in response to the advertiser-specified attribute 222 in terms of multiple pointing device manipulations (e.g., pointing and/or clicking), following instructions present in an advertiser-specified attribute 222 such as an advertisement in a game, or the like.

User task sequencing deficits may or may not be distinguishable from user lack of interest. In either case, an entity may be interested in the output of a task sequencing test function. In cases where a neurological condition underlies a task sequencing deficit behavior, an entity may be interested in this information. For example, data from an individual exhibiting failure to complete a sequence of tasks due to a neurological condition may be excluded from a survey by an entity. Alternatively, for example, data about the behavior of a user 106 with a task sequencing deficit relative to an advertiser-specified attribute may be of interest to an entity in terms of identifying characteristics of users with positive or negative responses to a specific advertiser-specified attribute.

A user's task sequencing attributes are indicators of a user's mental status. An example of a task sequencing test function may be a measure of a user's perseveration. For example, a task sequencing test module 164 and/or user-health test function unit 140 may ask a user to continue drawing a silhouette pattern of alternating triangles and squares (i.e., a written alternating sequencing task) for a time period. In users with perseveration problems, the user may get stuck on one shape and keep drawing triangles. Another common finding is motor impersistence, a form of distractibility in which users only briefly sustain a motor action in response to a command such as "raise your arms" or "Look to the right." Ability to suppress inappropriate behaviors can be tested by the auditory "Go-No-Go" test, in which the user moves a finger in response to one sound, but must keep it still in response to two sounds. Alternatively, a task sequencing test module 164 and/or user-health test function unit 140 may prompt a user to perform a multi-step function in the context of an application 120 including an advertiser-specified attribute 122, for example. For example, an application 120 such as a game may prompt a user 106 to enter a character's name, equip an advertiser-specified attribute such as a marked item from an inventory, and click on a certain direction of travel, in that order. Difficulty completing this task may indicate, for example, a frontal lobe defect associated with dementia.

Decreased ability to perform sequencing tasks may be indicative of stroke (e.g., embolic, thrombotic, or due to vasculitis), brain tumor (e.g., glioma or meningioma), or dementia (caused by, for example, Alzheimer's disease, vascular dementia, Parkinson's disease, Huntingdon's disease, Creutzfeldt-Jakob disease, Pick disease, head injury, infection (e.g., meningitis, encephalitis, HIV, or syphilis), normal pressure hydrocephalus, brain tumor, exposure to toxin (for example, lead or other heavy metals), metabolic disorders, hormone disorders, hypoxia (caused by, e.g., emphysema, pneumonia, or congestive heart failure), drug reactions (e.g., anti-cholinergic side effects, drug overuse, drug abuse (e.g., cocaine or heroin).

In the context of the above task sequencing test function, as set forth herein available data arising from the user-health test function are one or more of various types of user-application interaction data 132 described herein. Altered task sequencing function may indicate certain of the possible conditions discussed above. One skilled in the art can establish or determine parameters or values relating to the one or more types of user data indicative of altered task sequencing function, or the one or more types of user data indicative of a likely condition associated with altered task sequencing function. Parameters or values can be set by one skilled in the art based on knowledge, direct experience, or using available resources such as websites, textbooks, journal articles, or the like. An example of a relevant website can be found in the online Merck Manual at http://www.merck.com/mmhe/sec06/ch077/ch077c.html#tb077_1. Examples of relevant textbooks include Patten, J. P., "Neurological Differential Diagnosis," Second Ed., Springer-Verlag, London, 2005; Kasper, Braunwald, Fauci, Hauser, Longo, and Jameson, "Harrison's Principles of Internal Medicine," $16^{th}$ Ed., McGraw-Hill, New York, 2005; Greenberg, M. S., "Handbook of Neurosurgery," $6^{th}$ Ed., Thieme, Lakeland, 2006; and Victor, M., and Ropper, A. H., "Adams and Victor's Principles of Neurology," $7^{th}$ Ed., McGraw-Hill, New York, 2001.

Operation 706 depicts specifying at least one visual field test function responsive to the interaction between the user and the at least one advertiser-specified attribute. For example, a user-health test function unit 140 and/or user-health test function assignment module 130 may specify at least one visual field test function responsive to the interaction between the user and the at least one advertiser-specified attribute 122. A specified visual field test module 150 may respond to user-application interaction data 132 via data detection module 116, data capture module 114, user image data 134, and/or user input data 136 indicating an interaction between the user and at least one advertiser-specified attribute 122.

Visual field can be tested, for example, by measuring user actions with respect to items on a display including the ability of the user to acknowledge items within a specified field of view via cursor movement, clicking, voice, eye movement, or other ways of, for example, selecting or otherwise manipulating items, including an advertiser-specified attribute.

Visual field information may be of interest to an advertising entity, for example, where a user 106 performs actions within a computerized game world with respect to an advertiser-specified attribute such as an advertisement in the computerized game world. For example, a user's ability to click on a limited portion of a screen due to a visual field defect may be of interest to an advertiser for purposes of advertisement placement within the computerized game world. For example, knowing that a user 106 has a limited field of vision may prompt an advertiser to reposition an advertisement closer to the center of the screen relative to highly-traveled routes and/or to avoid placing the advertisement in the periphery of the screen for affected users. Clicking a target on a display and/or vocally acknowledging a visual signal on a display may comprise the user-health test function output 190 (e.g., output of visual field test module 150).

For example, an entity 170 such as a merchant may be interested in determining whether a user 106 notices an advertiser-specified attribute 122 such as a virtual world avatar wearing the merchant's brand of clothing, for example, bearing the merchant's logo. If the user 106 exhibits a limited field of vision in normal clicking function within the virtual world, the merchant may request prominent placement of an avatar bearing an advertiser-specified attribute near the center of the screen and/or more frequent movement of the avatar in the area of the center of the user's field of vision.

In another embodiment, an advertiser may want to know if a low-priced advertisement placed in a peripheral screen location is noticed by an acceptable percentage of users of a virtual world, game, web site, or the like. Visual field function may be gauged from a user's interaction with the application 220. User-application interaction data 260 may demonstrate user interest in the advertisement in the form of direct user-initiated acknowledgement of an advertisement in terms of pointing device manipulations (e.g., pointing and/or clicking), speaking, or the like.

User visual field deficits may or may not be distinguishable from user lack of interest. In either case, an entity such as an advertiser may be interested in the output of a visual field test function, such as the output of a visual field test module 150. In cases where a neurological condition underlies a visual field deficit behavior, an entity may be interested in this information. For example, data from the interaction of a user exhibiting failure to acknowledge an onscreen item due to a neurological condition may be excluded from a survey by an entity 170. Alternatively, for example, data about the behavior of a user 106 with a visual field deficit relative to an advertiser-specified attribute 122 may be of interest to an entity in terms of identifying characteristics of users with positive or negative responses to, for example, specific advertising.

An example of a visual field test function may be a measure of a user's gross visual acuity, for example using a Snellen eye chart or visual equivalent on a display. Alternatively, a campimeter may be used to conduct a visual field test. A visual field test module 130 and/or user-health test function unit 140 can prompt a user to activate a portion of a display when the user can detect an object entering their field of view from a peripheral location relative to a fixed point of focus, either with both eyes or with one eye covered at a time. Such testing could be done in the context of, for example, a new email alert including an advertiser-specified attribute 122 that requires clicking and that appears in various locations on a display. Based upon the location of decreased visual field, the defect can be localized, for example in a quadrant system.

Visual field defects may indicate optic nerve conditions such as pre-chiasmatic lesions, which include fractures of the sphenoid bone (e.g., transecting the optic nerve), retinal tumors, or masses compressing the optic nerve. Such conditions may result in unilateral blindness and unilaterally unreactive pupil (although the pupil may react to light applied to the contralateral eye). Bi-temporal hemianopsia can be caused by glaucoma, pituitary adenoma, craniopharyngioma or saccular Berry aneurysm at the optic chiasm. Post-chiasmatic lesions are associated with homonymous hemianopsia or quadrantanopsia depending on the location of the lesion. A pre-chiasmatic lesion results in ipsilateral eye blindness. A chiasmatic lesion can result in bi-temporal hemianopsia (i.e., tunnel vision). Post-chiasmatic lesions proximal to the geniculate ganglion can result in left or right homonymous hemianopsia. Lesions distal to the geniculate ganglion can result in upper or lower homonymous quadrantanopsia.

In the context of the above visual field test function, as set forth herein available data arising from the user-health test function are one or more of various types of user-application interaction data 132 described herein. Altered visual field may indicate certain of the possible conditions discussed above. One skilled in the art can establish or determine parameters or values relating to the one or more types of user data indicative of altered visual field, or the one or more types of user data indicative of a likely condition associated with altered visual field. Parameters or values can be set by one skilled in the art based on knowledge, direct experience, or using available resources such as websites, textbooks, journal articles, or the like. An example of a relevant website can be found in the online Merck Manual at http://www.merck.com/mmhe/sec06/ch077/ch077c.html#tb077_1. Examples of relevant textbooks include Patten, J. P., "Neurological Differential Diagnosis," Second Ed., Springer-Verlag, London, 2005; Kasper, Braunwald, Fauci, Hauser, Longo, and Jameson, "Harrison's Principles of Internal Medicine," 16$^{th}$ Ed., McGraw-Hill, New York, 2005; Greenberg, M. S., "Handbook of Neurosurgery," 6$^{th}$ Ed., Thieme, Lakeland, 2006; and Victor, M., and Ropper, A. H., "Adams and Victor's Principles of Neurology," 7$^{th}$ Ed., McGraw-Hill, New York, 2001.

Operation 506 depicts specifying at least one pupil movement or eye movement test function responsive to the interaction between the user and the at least one advertiser-specified attribute. For example, a user-health test function unit 140 and/or user-health test function assignment module 130 may specify at least one pupil movement or eye movement test function responsive to the interaction between the user and the at least one advertiser-specified attribute 122. A specified eye movement or pupil movement test module 158 may respond to user-application interaction data 132 via data detection module 116, data capture module 114, user image data 134, and/or user input data 136 indicating an interaction between the user and at least one advertiser-specified attribute 122.

Pupillary reflex or eye movement can be tested, for example, by measuring user pupil and/or eye movements, perhaps in relation to items on a display, including an advertiser-specified attribute 122. Pupillary reflex or eye movement information may be of interest to an advertising entity, for example, where a user 106 performs actions within a local instance of application 212 such as a computerized game world with respect to an advertisement in the computerized game world. For example, a user's eye movement to a part of the screen containing an advertisement may be of interest to an advertiser for purposes of advertisement placement or determining advertisement noticeability and/or effectiveness within the computerized game world. For example, knowing that a user's eyes have been attracted by an advertisement may be of interest to an advertiser. Accordingly, pupil dilation or contraction, and/or eye movements may comprise the user-health test function output 190, e.g., output of eye movement or pupil movement test module 158.

For example, a merchant may be interested in measuring whether a user notices a virtual world advertisement in a particular virtual world environment. If the user exhibits eye movements toward the advertisement on a display, then an advertiser may count this as user interest in the advertisement.

In another embodiment, an internet search engine may want to know if a user is looking at an advertisement placed at a specific location on a screen showing search results. A camera may monitor the user's eye movements in order to determine whether the user looks at the advertisement, for example, during a certain time period. Interest in an advertisement also may be ascertained by measuring pupil dilation during a user's interaction with an advertiser-specified attribute 222 such as an advertisement.

Data capture module 114 may include a smart camera that can capture images, process them and issue control commands within a millisecond time frame. Such smart cameras are commercially available (e.g., Hamamatsu's Intelligent Vision System; http://ip.hamamatsu.com/en/product_info/index.html). Such image capture systems may include dedicated processing elements for each pixel image sensor. Other camera systems may include, for example, a pair of infrared charge coupled device cameras to continuously monitor pupil size and position as a user watches a visual target moving forward and backward. This can provide real-time data relating to pupil accommodation relative to objects on a display, which information may be of interest to an entity 170 (e.g., http://ip.hamamatsu.com/en/rd/publication/scientific_american/common/pdf/scientific_0608.pdf).

Eye movement and/or pupil movement may be measured by video-based eye trackers. In these systems, a camera focuses on one or both eyes and records eye movement as the viewer looks at a stimulus. Contrast may be used to locate the center of the pupil, and infrared and near-infrared non-collumnated light may be used to create a corneal reflection. The vector between these two features can be used to compute gaze intersection with a surface after a calibration for an user 106.

Two types of eye tracking techniques include bright pupil eye tracking and dark pupil eye tracking. Their difference is based on the location of the illumination source with respect to the optics. If the illumination is coaxial with the optical path, then the eye acts as a retroreflector as the light reflects off the retina, creating a bright pupil effect similar to red eye. If the illumination source is offset from the optical path, then the pupil appears dark.

Bright Pupil tracking creates greater iris/pupil contrast allowing for more robust eye tracking with all iris pigmentation and greatly reduces interference caused by eyelashes and other obscuring features. It also allows for tracking in lighting conditions ranging from total darkness to very bright light.

However, bright pupil techniques are not recommended for tracking outdoors as extraneous IR sources may interfere with monitoring.

Eye tracking configurations can vary; in some cases the measurement apparatus may be head-mounted, in some cases the head should be stable (e.g., stabilized with a chin rest), and in some cases the eye tracking may be done remotely to automatically track the head during motion. Most eye tracking systems use a sampling rate of at least 30 Hz. Although 50/60 Hz is most common, many video-based eye trackers run at 240, 350 or even 1000/1250 Hz, which is recommended in order to capture the detail of the very rapid eye movements during reading, or during studies of neurology.

Eye movements are typically divided into fixations, when the eye gaze pauses in a certain position, and saccades, when the eye gaze moves to another position. A series of fixations and saccades is called a scanpath. Most information from the eye is made available during a fixation, not during a saccade. The central one or two degrees of the visual angle (the fovea) provide the bulk of visual information; input from larger eccentricities (the periphery) generally is less informative. Therefore the locations of fixations along a scanpath indicate what information loci on the stimulus were processed during an eye tracking session. On average, fixations last for around 200 milliseconds during the reading of linguistic text, and 350 milliseconds during the viewing of a scene. Preparing a saccade towards a new goal takes around 200 milliseconds.

Scanpaths are useful for analyzing cognitive intent, interest, and salience. Other biological factors (some as simple as gender) may affect the scanpath as well. Eye tracking in human-computer interaction typically investigates the scanpath for usability purposes, or as a method of input in gaze-contingent displays, also known as gaze-based interfaces.

There are two primary components to most eye tracking studies: statistical analysis and graphic rendering. These are both based mainly on eye fixations on specific elements. Statistical analyses generally sum the number of eye data observations that fall in a particular region. Commercial software packages may analyze eye tracking and show the relative probability of eye fixation on each feature in a website. This allows for a broad analysis of which site elements received attention and which ones were ignored. Other behaviors such as blinks, saccades, and cognitive engagement can be reported by commercial software packages. Statistical comparisons can be made to test, for example, competitors, prototypes or subtle changes to a web design. They can also be used to compare participants in different demographic groups. Statistical analyses may quantify where users look, sometimes directly, and sometimes based on models of higher-order phenomena (e.g., cognitive engagement).

In addition to statistical analysis, it is often useful to provide visual depictions of eye tracking results. One method is to create a video of an eye tracking testing session with the gaze of a participant superimposed upon it. This allows one to effectively see through the eyes of the consumer during interaction with a target medium. Another method graphically depicts the scanpath of a single participant during a given time interval. Analysis may show each fixation and eye movement of a participant during a search on a virtual shelf display of breakfast cereals, analyzed and rendered with a commercial software package. For example, a different color may represent one second of viewing time, allowing for a determination of the order in which products are seen. Analyses such as these may be used as evidence of specific trends in visual behavior.

A similar method sums the eye data of multiple participants during a given time interval as a heat map. A heat map may be produced by a commercial software package, and shows the density of eye fixations for several participants superimposed on the original stimulus, for example, a magazine cover. Red and orange spots represent areas with high densities of eye fixations. This allows one to examine which regions attract the focus of the viewer.

Commercial eye tracking applications include web usability, advertising, sponsorship, package design and automotive engineering. Eye tracking studies may presenting a target stimulus to a sample of consumers while an eye tracker is used to record the activity of the eye. Examples of target stimuli may include websites, television programs, sporting events, films, commercials, magazines, newspapers, packages, shelf displays, consumer systems (ATMs, checkout systems, kiosks), and software. The resulting data can be statistically analyzed and graphically rendered to provide evidence of specific visual patterns. By examining fixations, saccades, pupil dilation, blinks, and a variety of other behaviors, researchers can determine a great deal about the effectiveness of a given medium or product.

A prominent field of eye tracking research is web usability. While traditional usability techniques are often quite powerful in providing information on clicking and scrolling patterns, eye tracking offers the ability to analyze user interaction between the clicks. This provides insight into which features are the most eye-catching, which features cause confusion, and which ones are ignored altogether. Specifically, eye tracking can be used to assess search efficiency, branding, online advertisement, navigation usability, overall design, and many other site components. Analyses may target a prototype or competitor site in addition to the main client site.

Eye tracking is commonly used in a variety of different advertising media. Commercials, print ads, online ads, and sponsored programs are all conducive to analysis with eye tracking technology. Analyses may focus on visibility of a target product or logo in the context of a magazine, newspaper, website, virtual world, or televised event. This allows researchers to assess in great detail how often a sample of consumers fixates on the target logo, product, or advertisement. In this way, an advertiser can quantify the success of a given campaign in terms of actual visual attention.

Eye tracking also provides package designers with the opportunity to examine the visual behavior of a consumer while interacting with a target package. This may be used to analyze distinctiveness, attractiveness and the tendency of the package to be chosen for purchase. Eye tracking is often used while the target product is in the prototype stage. Prototypes are tested against each other and against competitors to examine which specific elements are associated with high visibility and/or appeal.

Another application of eye tracking research is in the field of automotive design. Eye tracking cameras may be integrated into automobiles to provide the vehicle with the capacity to assess in real-time the visual behavior of the driver. The National Highway Traffic Safety Administration (NHTSA) estimates that drowsiness is the primary causal factor in 100,000 police-reported accidents per year. Another NHTSA study suggests that 80% of collisions occur within three seconds of a distraction. By equipping automobiles with the ability to monitor drowsiness, inattention, and cognitive engagement driving safety could be dramatically enhanced. Lexus® claims to have equipped its LS 460 automobile with the first driver monitor system in 2006, providing a warning if the driver takes his or her eye off the road.

Eye tracking is also used in communication systems for disabled persons, allowing the user to speak, mail, surf the web and so with only the eyes as tool. Eye control works even when the user has involuntary body movement as a result of cerebral palsy or other disability, and/or when the user wears glasses.

Eye movement or pupil movement may be gauged from a user's interaction with an application 220. User-application interaction data 260 may demonstrate user interest in an advertiser-specified attribute 222 such as an advertisement displayed in the context of application 220 in the form of eye or pupil movement in response to the advertisement in terms of repeated or sustained eye or pupil movements in relation to the advertisement (e.g., camera measurements of eye movement tracking an advertisement, and/or pupil dilation in response to seeing an advertisement), or the like.

User eye movement or pupil movement deficits may or may not be distinguishable from user lack of interest. In either case, an entity 170 may be interested in the output of a pupillary reflex or eye movement test module 158. In cases where a neurological condition underlies a specific pupillary reflex or eye movement behavior, an entity may be interested in this information. For example, data from a user exhibiting failure to look at an item in a virtual world due to a neurological condition may be excluded from a survey by an entity. Alternatively, for example, data about the behavior of a user with a certain pupillary reflex or eye movement behavior relative to an advertisement may be of interest to an entity in terms of identifying characteristics of users with positive or negative responses to specific advertising.

An example of a pupillary reflex test function may be a measure of a user's pupils when exposed to light or objects at various distances. An eye movement or pupil movement test module 158 and/or user-health test function unit 140 may assess the size and symmetry of a user's pupils before and after a stimulus, such as light or focal point. Anisocoria (i.e., unequal pupils) of up to 0.5 mm is fairly common, and is benign provided pupillary reaction to light is normal. Pupillary reflex can be tested in a darkened room by shining light in one pupil and observing any constriction of the ipsilateral pupil (direct reflex) or the contralateral pupil (contralateral reflex). If abnormality is found with light reaction, pupillary accommodation can be tested by having the user focus on an object at a distance, then focus on the object at about 10 cm from the nose. Pupils should converge and constrict at close focus.

Pupillary abnormalities may be a result of either optic nerve or oculomotor nerve lesions. An optic nerve lesion (e.g., blind eye) will not react to direct light and will not elicit a consensual pupillary constriction, but will constrict if light is shown in the opposite eye. A Horner's syndrome lesion (sympathetic chain lesion) can also present as a pupillary abnormality. In Horner's syndrome, the affected pupil is smaller but constricts to both light and near vision and may be associated with ptosis and anhydrosis. In an oculomotor nerve lesion, the affected pupil is fixed and dilated and may be associated with ptosis and lateral deviation (due to unopposed action of the abducens nerve). Small pupils that do not react to light but do constrict with near vision (i.e., accommodate but do not react to light) can be seen in central nervous system syphilis ("Argyll Robertson pupil").

Pupillary reflex deficiencies may indicate damage to the oculomotor nerve in basilar skull fracture or uncal herniation as a result of increased intracranial pressure. Masses or tumors in the cavernous sinus, syphilis, or aneurysm may also lead to compression of the oculomotor nerve. Injury to the oculomotor nerve may result in ptosis, inferolateral displacement of the ipsilateral eye (which can present as diplopia or strabismus), or mydriasis.

An example of an eye movement test function may be an eye movement or pupil movement test module 158 and/or user-health test function unit 140 measurement of a user's ability to follow a target on a display with her eyes throughout a 360° range. Such testing may be done in the context of a user playing a game or participating in a videoconference, including an advertiser-specified attribute 222. In such examples, user-application interaction data 260 may be obtained through a camera in place as a user monitoring device 284 that can monitor the eye movements of the user during interaction with the local instance of application 212.

Testing of the trochlear nerve or the abducens nerve for damage may involve measurement of extraocular movements. The trochlear nerve performs intorsion, depression, and abduction of the eye. A trochlear nerve lesion may present as extorsion of the ipsilateral eye and worsened diplopia when looking down. Damage to the abducens nerve may result in a decreased ability to abduct the eye.

Abnormalities in eye movement may indicate fracture of the sphenoid wing, intracranial hemorrhage, neoplasm, or aneurysm. Such insults may present as extorsion of the ipsilateral eye. Individuals with this condition complain of worsened diplopia with attempted downgaze, but improved diplopia with head tilted to the contralateral side. Injury to the abducens nerve may be caused by aneurysm, a mass in the cavernous sinus, or a fracture of the skull base. Such insults may result in extraocular palsy defined by medial deviation of the ipsilateral eye. Users with this condition may present with diplopia that improves when the contralateral eye is abducted.

Nystagmus is a rapid involuntary rhythmic eye movement, with the eyes moving quickly in one direction (quick phase), and then slowly in the other direction (slow phase). The direction of nystagmus is defined by the direction of its quick phase (e.g., right nystagmus is due to a right-moving quick phase). Nystagmus may occur in the vertical or horizontal directions, or in a semicircular movement. Terminology includes downbeat nystagmus, upbeat nystagmus, seesaw nystagmus, periodic alternating nystagmus, and pendular nystagmus. There are other similar alterations in periodic eye movements (saccadic oscillations) such as opsoclonus or ocular flutter. One can think of nystagmus as the combination of a slow adjusting eye movement (slow phase) as would be seen with the vestibulo-ocular reflex, followed by a quick saccade (quick phase) when the eye has reached the limit of its rotation.

In medicine, the clinical importance of nystagmus is that it indicates that the user's spatial sensory system perceives rotation and is rotating the eyes to adjust. Thus it depends on the coordination of activities between two major physiological systems: the vision and the vestibular apparatus (which controls posture and balance). This may be physiological (i.e., normal) or pathological.

Vestibular nystagmus may be central or peripheral. Important differentiating features between central and peripheral nystagmus include the following: peripheral nystagmus is unidirectional with the fast phase opposite the lesion; central nystagmus may be unidirectional or bidirectional; purely vertical or torsional nystagmus suggests a central location; central vestibular nystagmus is not dampened or inhibited by visual fixation; tinnitus or deafness often is present in peripheral vestibular nystagmus, but it usually is absent in central vestibular nystagmus. According to Alexander's law, the nystagmus associated with peripheral lesions becomes more pronounced with gaze toward the side of the fast-beating component; with central nystagmus, the direction of the fast component is directed toward the side of gaze (e.g., left-beating in left gaze, right-beating in right gaze, and up-beating in upgaze).

Downbeat nystagmus is defined as nystagmus with the fast phase beating in a downward direction. The nystagmus usually is of maximal intensity when the eyes are deviated temporally and slightly inferiorly. With the eyes in this position, the nystagmus is directed obliquely downward. In most users, removal of fixation (e.g., by Frenzel goggles) does not influence slow phase velocity to a considerable extent, however, the frequency of saccades may diminish.

The presence of downbeat nystagmus is highly suggestive of disorders of the cranio-cervical junction (e.g., Arnold-Chiari malformation). This condition also may occur with bilateral lesions of the cerebellar flocculus and bilateral lesions of the medial longitudinal fasciculus, which carries optokinetic input from the posterior semicircular canals to the third nerve nuclei. It may also occur when the tone within pathways from the anterior semicircular canals is relatively higher than the tone within the posterior semicircular canals. Under such circumstances, the relatively unopposed neural activity from the anterior semicircular canals causes a slow upward pursuit movement of the eyes with a fast, corrective downward saccade. Additional causes include demyelination (e.g., as a result of multiple sclerosis), microvascular disease with vertebrobasilar insufficiency, brain stem encephalitis, tumors at the foramen magnum (e.g., meningioma, or cerebellar hemangioma), trauma, drugs (e.g., alcohol, lithium, or anti-seizure medications), nutritional imbalances (e.g., Wernicke encephalopathy, parenteral feeding, magnesium deficiency), or heat stroke.

Upbeat nystagmus is defined as nystagmus with the fast phase beating in an upward direction. Daroff and Troost described two distinct types. The first type consists of a large amplitude nystagmus that increases in intensity with upward gaze. This type is suggestive of a lesion of the anterior vermis of the cerebellum. The second type consists of a small amplitude nystagmus that decreases in intensity with upward gaze and increases in intensity with downward gaze. This type is suggestive of lesions of the medulla, including the perihypoglossal nuclei, the adjacent medial vestibular nucleus, and the nucleus intercalatus (structures important in gaze-holding). Upbeat nystagmus may also be an indication of benign paroxysmal positional vertigo.

Torsional (rotary) nystagmus refers to a rotary movement of the globe about its anteroposterior axis. Torsional nystagmus is accentuated on lateral gaze. Most nystagmus resulting from dysfunction of the vestibular system has a torsional component superimposed on a horizontal or vertical nystagmus. This condition occurs with lesions of the anterior and posterior semicircular canals on the same side (e.g., lateral medullary syndrome or Wallenberg syndrome). Lesions of the lateral medulla may produce a torsional nystagmus with the fast phase directed away from the side of the lesion. This type of nystagmus can be accentuated by otolithic stimulation by placing the user on their side with the intact side down (e.g., if the lesion is on the left, the nystagmus is accentuated when the user is placed on his right side).

This condition may occur when the tone within the pathways of the posterior semicircular canals is relatively higher than the tone within the anterior semicircular canals, and it can occur from lesions of the ventral tegmental tract or the brachium conjunctivum, which carry optokinetic input from the anterior semicircular canals to the third nerve nuclei.

Pendular nystagmus is a multivectorial nystagmus (i.e., horizontal, vertical, circular, and elliptical) with an equal velocity in each direction that may reflect brain stem or cerebellar dysfunction. Often, there is marked asymmetry and dissociation between the eyes. The amplitude of the nystagmus may vary in different positions of gaze. Causes of pendular nystagmus may include demyelinating disease, monocular or binocular visual deprivation, oculapalatal myoclonus, internuclear ophthalmoplegia, or brain stem or cerebellar dysfunction.

Horizontal nystagmus is a well-recognized finding in patients with a unilateral disease of the cerebral hemispheres, especially with large, posterior lesions. It often is of low amplitude. Such patients show a constant velocity drift of the eyes toward the intact hemisphere with fast saccade directed toward the side of the lesion.

Seesaw nystagmus is a pendular oscillation that consists of elevation and intorsion of one eye and depression and extorsion of the fellow eye that alternates every half cycle. This striking and unusual form of nystagmus may be seen in patients with chiasmal lesions, suggesting loss of the crossed visual inputs from the decussating fibers of the optic nerve at the level of the chiasm as the cause or lesions in the rostral midbrain. This type of nystagmus is not affected by otolithic stimulation. Seesaw nystagmus may also be caused by parasellar lesions or visual loss secondary to retinitis pigmentosa.

Gaze-evoked nystagmus is produced by the attempted maintenance of an extreme eye position. It is the most common form of nystagmus. Gaze-evoked nystagmus is due to a deficient eye position signal in the neural integrator network. Thus, the eyes cannot be maintained at an eccentric orbital position and are pulled back toward primary position by the elastic forces of the orbital fascia. Then, corrective saccade moves the eyes back toward the eccentric position in the orbit.

Gaze-evoked nystagmus may be caused by structural lesions that involve the neural integrator network, which is dispersed between the vestibulocerebellum, the medulla (e.g., the region of the nucleus prepositus hypoglossi and adjacent medial vestibular nucleus "NPH/MVN"), and the interstitial nucleus of Cajal ("INC"). Patients recovering from a gaze palsy go through a period where they are able to gaze in the direction of the previous palsy, but they are unable to sustain gaze in that direction; therefore, the eyes drift slowly back toward primary position followed by a corrective saccade. When this is repeated, a gaze-evoked or gaze-paretic nystagmus results.

Gaze-evoked nystagmus often is encountered in healthy users; in which case, it is called end-point nystagmus. End-point nystagmus usually can be differentiated from gaze-evoked nystagmus caused by disease, in that the former has lower intensity and, more importantly, is not associated with other ocular motor abnormalities. Gaze-evoked nystagmus also may be caused by alcohol or drugs including anti-convulsants (e.g., phenobarbital, phenytoin, or carbamazepine) at therapeutic dosages.

Spasmus nutans is a rare condition with the clinical triad of nystagmus, head nodding, and torticollis. Onset is from age 3-15 months with disappearance by 3 or 4 years. Rarely, it may be present to age 5-6 years. The nystagmus typically consists of small-amplitude, high frequency oscillations and usually is bilateral, but it can be monocular, asymmetric, and variable in different positions of gaze. Spasmus nutans occurs in otherwise healthy children. Chiasmal, suprachiasmal, or third ventricle gliomas may cause a condition that mimics spasmus nutans.

Periodic alternating nystagmus is a conjugate, horizontal jerk nystagmus with the fast phase beating in one direction for a period of approximately 1-2 minutes. The nystagmus has an intervening neutral phase lasting 10-20 seconds; the nystagmus begins to beat in the opposite direction for 1-2 minutes;

then the process repeats itself. The mechanism may be disruption of the vestibulo-ocular tracts at the pontomedullary junction. Causes of periodic alternating nystagmus may include Arnold-Chiari malformation, demyelinating disease, spinocerebellar degeneration, lesions of the vestibular nuclei, head trauma, encephalitis, syphilis, posterior fossa tumors, or binocular visual deprivation (e.g., ocular media opacities).

Abducting nystagmus of internuclear ophthalmoplegia ("INO") is nystagmus in the abducting eye contralateral to a medial longitudinal fasciculus ("MLF") lesion.

In the context of the above eye movement or pupil movement test function, as set forth herein available data arising from the user-health test function are one or more of various types of user-application interaction data 132 described herein. Altered eye movement or pupil movement function may indicate certain of the possible conditions discussed above. One skilled in the art can establish or determine parameters or values relating to the one or more types of user data indicative of altered eye movement or pupil movement function, or the one or more types of user data indicative of a likely condition associated with altered eye movement or pupil movement function. Parameters or values can be set by one skilled in the art based on knowledge, direct experience, or using available resources such as websites, textbooks, journal articles, or the like. An example of a relevant website can be found in the online Merck Manual at http://www.merck.com/mmhe/sec06/ch077/ch077c.html#tb077_1. Examples of relevant textbooks include Patten, J. P., "Neurological Differential Diagnosis," Second Ed., Springer-Verlag, London, 2005; Kasper, Braunwald, Fauci, Hauser, Longo, and Jameson, "Harrison's Principles of Internal Medicine," 16$^{th}$ Ed., McGraw-Hill, New York, 2005; Greenberg, M. S., "Handbook of Neurosurgery," 6$^{th}$ Ed., Thieme, Lakeland, 2006; and Victor, M., and Ropper, A. H., "Adams and Victor's Principles of Neurology," 7$^{th}$ Ed., McGraw-Hill, New York, 2001.

Operation 508 depicts specifying at least one face pattern test function responsive to the interaction between the user and the at least one advertiser-specified attribute. For example, a user-health test function unit 140 and/or user-health test function assignment module 130 may specify at least one face pattern test function responsive to the interaction between the user and the at least one advertiser-specified attribute 122. A specified face pattern test module 160 may respond to user-application interaction data 132 via data detection module 116, data capture module 114, user image data 134, and/or user input data 136 indicating an interaction between the user and at least one advertiser-specified attribute 122.

Face pattern can be tested, for example, by measuring user facial features, perhaps in relation to a control user face pattern image captured when the user was not interacting with application 120 and/or advertiser-specified attribute 122. Alternatively, user face pattern module output may be compared to an average face pattern compiled from a large number of faces. Face pattern information may be of interest to an advertising entity, for example, where a user 106 exhibits some emotion with respect to an advertiser-specified attribute 122 such as an advertisement in, for example an email or virtual world. In one embodiment, a user's reaction to an onscreen advertisement may be a smile or frown that may be detectable by a camera monitoring the interaction. Information suggesting that a user smiles in response to viewing an advertisement may be of interest to an advertiser. Accordingly, facial patterns may comprise the user-health test function output 190, e.g., output of face pattern test module 160.

For example, a merchant may be interested in determining whether a user reacts positively or negatively or not at all to a virtual world advertisement in a particular virtual world environment. If the user exhibits changes in facial features in response to viewing the advertisement on a display, then an advertiser may gauge user interest in the advertisement. The fact pattern test module 160 may match a user's face pattern with a one of a set of emotion-correlated face patterns. For example, the fact pattern test module 160 may match a user's smile with a consensus smile image to identify a positive reaction to an advertiser-specified attribute 122. Accordingly, user eye movement or other user health test function may be tracked together with face pattern data to provide information as to events that may trigger a given face pattern, such as viewing an advertisement, clicking on an advertisement, and/or hearing an advertisement.

In another embodiment, an internet search engine may want information about a user's reaction to an avatar bearing an advertisement in a virtual world. A camera may monitor the user's facial features at times before and/or during and/or after the user interacts with the avatar. Positive interest in the advertisement-bearing avatar may be ascertained by detecting a smile; negative interest in the advertisement-bearing avatar may be ascertained by detecting a frown, smirk, knitting of the brows or other known facial feature indicating displeasure.

Face pattern may be measured relative to a user's interaction with an application 220. User-application interaction data 260 may demonstrate user interest in an advertiser-specified attribute such as an advertisement displayed in the context of application 220 in the form of altered face pattern in response to the advertisement in such as a face movement associated with the advertisement (e.g., camera measurements of facial features in response to seeing an advertisement), or the like.

User face pattern changes may or may not be distinguishable from user lack of interest, or such changes may be unrelated to an onscreen item or sound. In any case, an entity 170 may be interested in the output of a face pattern test module 160. In cases where a neurological condition underlies a specific face pattern change, an entity 170 may be interested in this information. For example, data from an individual exhibiting failure to react to an item in a virtual world due to a neurological condition (perhaps due to Bell's palsy) may be excluded from a survey by the entity 170 receiving the data. Alternatively, for example, data about the face pattern changes of a user including smiling, laughing, grinning, frowning, or the like may be of interest to an entity 170 in terms of identifying a positive response, negative response, or lack of response of a user 106 to advertising.

An example of a face pattern test function may be a face pattern test module 160 and/or user-health test function unit 140 that can compare a user's face while at rest, specifically looking for nasolabial fold flattening or drooping of the corner of the mouth, with the user's face while moving certain facial features. The user may be asked to raise her eyebrows, wrinkle her forehead, show her teeth, puff out her cheeks, or close her eyes tight. Such testing may done via facial pattern recognition software used in conjunction with, for example, a videoconferencing application. Any weakness or asymmetry may indicate a lesion in the facial nerve. In general, a peripheral lesion of the facial nerve may affect the upper and lower face while a central lesion may only affect the lower face. Movement of facial features may be identifiable as an indicator of emotion, e.g., associating a smile with pleasure, laughing with pleasure, a frown with displeasure, pursing of the lips with displeasure, yawning with boredom.

Abnormalities in facial expression or pattern may indicate a petrous fracture. Peripheral facial nerve injury may also be due to compression, tumor, or aneurysm. Bell's Palsy is thought to be caused by idiopathic inflammation of the facial nerve within the facial canal. A peripheral facial nerve lesion involves muscles of both the upper and lower face and can involve loss of taste sensation from the anterior ⅔ of the tongue (via the chorda tympani). A central facial nerve palsy due to tumor or hemorrhage results in sparing of upper and frontal orbicularis occuli due to crossed innervation. Spared ability to raise eyebrows and wrinkle the forehead helps differentiate a peripheral palsy from a central process. This also may indicate stroke or multiple sclerosis.

In the context of the above face pattern test function, as set forth herein available data arising from the user-health test function are one or more of various types of user-application interaction data 132 described herein. Altered face pattern may indicate certain of the possible conditions discussed above. One skilled in the art can establish or determine parameters or values relating to the one or more types of user data indicative of altered face pattern, or the one or more types of user data indicative of a likely condition associated with altered face pattern. Parameters or values can be set by one skilled in the art based on knowledge, direct experience, or using available resources such as websites, textbooks, journal articles, or the like. An example of a relevant website can be found in the online Merck Manual at http://www.merck.com/mmhe/sec06/ch077/ch077c.html#tb077_1. Examples of relevant textbooks include Patten, J. P., "Neurological Differential Diagnosis," Second Ed., Springer-Verlag, London, 2005; Kasper, Braunwald, Fauci, Hauser, Longo, and Jameson, "Harrison's Principles of Internal Medicine," 16$^{th}$ Ed., McGraw-Hill, New York, 2005; Greenberg, M. S., "Handbook of Neurosurgery," 6$^{th}$ Ed., Thieme, Lakeland, 2006; and Victor, M., and Ropper, A. H., "Adams and Victor's Principles of Neurology," 7$^{th}$ Ed., McGraw-Hill, New York, 2001.

FIG. 6 illustrates alternative embodiments of the example operational flow 300 of FIG. 3. FIG. 6 illustrates example embodiments where the specifying operation 3 1 0 may include at least one additional operation. Additional operations may include operation 600, 602, 604, 606, and/or operation 608.

Operation 600 depicts specifying at least one hearing test function responsive to the interaction between the user and the at least one advertiser-specified attribute. For example, a user-health test function unit 140 and/or user-health test function assignment module 130 may specify at least one hearing test function responsive to the interaction between the user and the at least one advertiser-specified attribute 122. A specified hearing test module 166 may respond to user-application interaction data 132 via data detection module 116, data capture module 114, user image data 134, and/or user input data 136 indicating an interaction between the user and at least one advertiser-specified attribute 122.

Hearing can be tested, for example, by measuring user reaction to sound during an interaction between user 106 and application 120 and/or advertiser-specified attribute 122. Hearing can be tested, for example, by measuring a user's reaction to a sound, perhaps by way of a face pattern image change, and/or a device signal such as a keyboard or mouse input signal acknowledging that the sound was heard by the user 106. User hearing information may be of interest to an advertising entity, for example, where a user 106 exhibits some reaction with respect to an audio advertisement, for example, on a website or in a virtual world. In one embodiment, a user's reaction to an audio advertisement may be a smile or frown that may be detectable by a camera monitoring the interaction. Information from the user-application interaction data 132 may suggest that a user has activated the sound portion of the website or the virtual world and is paying attention to the sound advertisement; this information may be of interest to an advertiser. Accordingly, reaction to audio signals, or user hearing data, may comprise the user-health test function output 190.

Hearing may be measured relative to a user's interaction with an application 220. User-application interaction data 260 may demonstrate user interest in an advertisement displayed in the context of application 220 in the form of the user turning on or increasing the volume of the advertisement (e.g., increasing device volume or increasing software volume controls, or the like).

User hearing data may or may not be distinguishable from user lack of interest, or such data may be unrelated to an application sound. In any case, an entity 170 may be interested in the output of a hearing test module 166. In cases where a neurological condition underlies a specific hearing behavior such as an apparent hearing deficit, an entity may be interested in this information. For example, data from an individual exhibiting failure to react to a sound in a virtual world due to a neurological condition may be excluded from a survey by the entity receiving the data. Alternatively, for example, data about the hearing ability of a user including listening habits relative to advertisements may be of interest to an entity in terms of identifying positive, negative or lack of responses to specific advertising.

An example of a hearing test function may be a hearing test module 166 and/or user-health test function unit 140 conducting a gross hearing assessment of a user's ability to hear sounds. This can be done by simply presenting sounds to the user or determining if the user can hear sounds presented to each of the ears. For example, a hearing test module 166 and/or user-health test function unit 140 may vary volume settings or sound frequency on a user's device 108 or within an application 120 over time to test user hearing. Alternatively, a hearing test module 166 and/or user-health test function unit 140 in a mobile phone device may carry out various hearing test functions.

Petrous fractures that involve the vestibulocochlear nerve may result in hearing loss, vertigo, or nystagmus (frequently positional) immediately after the injury. Severe middle ear infection can cause similar symptoms but have a more gradual onset. Acoustic neuroma is associated with gradual ipsilateral hearing loss. Due to the close proximity of the vestibulocochlear nerve with the facial nerve, acoustic neuromas often present with involvement of the facial nerve. Neurofibromatosis type II is associated with bilateral acoustic neuromas. Vertigo may be associated with anything that compresses the vestibulocochlear nerve including vascular abnormalities, inflammation, or neoplasm.

In the context of the above hearing test function, as set forth herein available data arising from the user-health test function are one or more of various types of user-application interaction data 260 described herein. Reduced hearing function may indicate certain of the possible conditions discussed above. One skilled in the art can establish or determine parameters or values relating to the one or more types of user data indicative of reduced hearing function, or the one or more types of user data indicative of a likely condition associated with reduced hearing function. Parameters or values can be set by one skilled in the art based on knowledge, direct experience, or using available resources such as websites, textbooks, journal articles, or the like. An example of a relevant website can be found in the online Merck Manual at http://www.merck.com/mmhe/sec06/ch077/ch077c.html#tb077_1. Examples of relevant textbooks include Patten, J. P., "Neurological Differential Diagnosis,"

Second Ed., Springer-Verlag, London, 2005; Kasper, Braunwald, Fauci, Hauser, Longo, and Jameson, "Harrison's Principles of Internal Medicine," 16th Ed., McGraw-Hill, New York, 2005; Greenberg, M. S., "Handbook of Neurosurgery," 6th Ed., Thieme, Lakeland, 2006; and Victor, M., and Ropper, A. H., "Adams and Victor's Principles of Neurology," 7th Ed., McGraw-Hill, New York, 2001.

Operation 602 depicts specifying at least one motor skill or body movement test function responsive to the interaction between the user and the at least one advertiser-specified attribute. For example, a user-health test function unit 140 and/or user-health test function assignment module 130 may specify at least one motor skill or body movement test function responsive to the interaction between the user and the at least one advertiser-specified attribute 122. A specified motor skill or body movement test module 168 may respond to user-application interaction data 132 via data detection module 116, data capture module 114, user image data 134, and/or user input data 136 indicating an interaction between the user and at least one advertiser-specified attribute 122.

A user's motor skill or body movement can be tested, for example, by measuring a user's ability to effect an input into, for example, the device 108. User motor skill information may be of interest to an advertising entity, for example, where a user 106 exhibits some reaction with respect to an advertisement, for example, in a computerized game world or in another virtual world. In one embodiment, a user's reaction to an advertisement may include clicking on an icon representing a merchant's product as a prelude to a purchase. Information from the user-application interaction data 132 may suggest that a user has certain likes and dislikes among listed products on a webpage, or among various advertisements; this information may be of interest to a merchant and/or advertiser. Accordingly, user motor skill or body movement test module 168 output may comprise the user-health test function output 190.

Motor skill or body movement may be measured relative to a user's interaction with an application 220. User-application interaction data 260 may demonstrate user interest in an advertisement displayed in the context of application 220 in the form of typing, clicking, or otherwise acknowledging the advertisement (e.g., clicking an image on a webpage, responding to a prompt, or the like).

User motor skill data may or may not be distinguishable from user lack of interest, or such data may be unrelated to an application visual object or sound, or to a user-health test function object or sound. In any case, an entity 170 may be interested in the output of a motor skill or body movement test module 168. In cases where a neurological condition underlies a specific motor skill attribute or behavior such as an apparent motor skill deficit, an entity 170 may be interested in this information. For example, data from an individual exhibiting failure to manipulate a pointing device to effect a response due to a neurological condition may be excluded from a survey by the entity receiving the data; or alternatively, the entity may provide alternative means for the user to respond, such as by voice. Alternatively, for example, data about the motor skill ability of a user including typing and/or pointing device proficiency relative to an application, user-health test function, and/or advertisement may be of interest to an entity in terms of identifying positive, negative or lack of responses to specific advertising.

An example of a motor skill test function may be a measure of a user's ability to perform a physical task, or a measure of tremor in a body part (i.e., a rhythmic, involuntary, or oscillating movement of a body part occurring in isolation or as part of a clinical syndrome). A motor skill or body movement test module 168 and/or user-health test function unit 140 may measure, for example, a user's ability to traverse a path on a display in straight line with a pointing device, to type a certain sequence of characters without error, or to type a certain number of characters without repetition. For example, a wobbling cursor on a display may indicate ataxia in the user, or a wobbling cursor while the user is asked to maintain the cursor on a fixed point on a display may indicate early Parkinson's disease symptoms. Alternatively, a user may be prompted to switch tasks, for example, to alternately type some characters using a keyboard and click on some target with a mouse. If a user has a motor skill deficiency, she may have difficulty stopping one task and starting the other task.

In clinical practice, characterization of tremor is important for etiologic consideration and treatment. Common types of tremor include resting tremor, postural tremor, action or kinetic tremor, task-specific tremor, or intention or terminal tremor. Resting tremor occurs when a body part is at complete rest against gravity. Tremor amplitude tends to decrease with voluntary activity. Causes of resting tremor may include Parkinson's disease, Parkinson-plus syndromes (e.g., multiple system atrophy, progressive supranuclear palsy, or corticobasal degeneration), Wilson's disease, drug-induced Parkinsonism (e.g., neuroleptics, Reglan, or phenthiazines), or long-standing essential tremor.

Postural tremor occurs during maintenance of a position against gravity and increases with action. Action or kinetic tremor occurs during voluntary movement. Examples of postural and action tremors may include essential tremor (primarily postural), metabolic disorders (e.g., thyrotoxicosis, pheochromocytoma, or hypoglycemia), drug-induced parkinsonism (e.g., lithium, amiodarone, or beta-adrenergic agonists), toxins (e.g., alcohol withdrawal, heavy metals), neuropathic tremor (e.g., neuropathy).

Task-specific tremor emerges during specific activity. An example of this type is primary writing tremor. Intention or terminal tremor manifests as a marked increase in tremor amplitude during a terminal portion of targeted movement. Examples of intention tremor include cerebellar tremor and multiple sclerosis tremor.

A user's body movement ability can be tested, for example, by measuring a user's ability to move various body parts. User body movement information may be of interest to an advertising entity, for example, where a user 106 exhibits some reaction with respect to an advertisement, for example, on a website. In one embodiment, a user's reaction to an advertisement may include interacting with a touchpad to move and/or select an icon representing a merchant's product. Information from the user-application interaction data 132 may suggest that a user has certain likes and dislikes among listed products on a webpage, or among various advertisements; this information may be of interest to a merchant and/or advertiser. Accordingly, user body movement data may comprise the user-health test function output 190.

Body movement may be measured relative to a user's interaction with an application 220. User-application interaction data 260 may demonstrate user interest in an advertisement displayed in the context of application 220 in the form of typing, clicking, hand waving, gesturing, running, or otherwise acknowledging the advertisement (e.g., clicking an image on a webpage, waving a remote control device, responding to a prompt, jumping for joy, or the like).

User body movement data may or may not be distinguishable from user lack of interest, or such data may be unrelated to an application visual object or sound, or to a user-health test function object or sound. In any case, an entity 170 may be interested in the output of a motor skill or body movement test module 168. In cases where a neurological condition underlies a specific body movement attribute or behavior such as an apparent body movement deficit, an entity may be interested in this information. For example, data from an individual exhibiting erratic body movements due to a neurological condition may be excluded from a survey by the entity receiving the data; or alternatively, the entity may provide alternative means for the user to respond, such as by voice. Alternatively, for example, data about the body movement ability of a user including typing and/or pointing device proficiency relative to an application, user-health test function, and/or advertisement may be of interest to an entity in terms of identifying positive, negative or lack of responses to specific advertising.

An example of a body movement test function may be first observing the user for atrophy or fasciculation in the trapezius muscles, shoulder drooping, or displacement of the scapula. A motor skill or body movement test module 168 and/or user-health test function unit 140 may then instruct the user to turn the head and shrug shoulders against resistance. Weakness in turning the head in one direction may indicate a problem in the contralateral spinal accessory nerve, while weakness in shoulder shrug may indicate an ipsilateral spinal accessory nerve lesion. Ipsilateral paralysis of the sternocleidomastoid and trapezius muscles due to neoplasm, aneurysm, or radical neck surgery also may indicate damage to the spinal accessory nerve. A motor skill or body movement test module 168 and/or user-health test function unit 140 may perform gait analysis, for example, in the context of a security system surveillance application involving video monitoring of the user.

Cerebellar disorders can disrupt body coordination or gait while leaving other motor functions relatively intact. The term ataxia is often used to describe the abnormal movements seen in coordination disorders. In ataxia, there are medium-to large-amplitude involuntary movements with an irregular oscillatory quality superimposed on and interfering with the normal smooth trajectory of movement. Overshoot is also commonly seen as part of ataxic movements and is sometimes referred to as "past pointing" when target-oriented movements are being discussed. Another feature of coordination disorders is dysdiadochokinesia (i.e., abnormal alternating movements). Cerebellar lesions can cause different kinds of coordination problems depending on their location. One important distinction is between truncal ataxia and appendicular ataxia. Appendicular ataxia affects movements of the extremities and is usually caused by lesions of the cerebellar hemispheres and associated pathways. Truncal ataxia affects the proximal musculature, especially that involved in gait stability, and is caused by midline damage to the cerebellar vermis and associated pathways.

Fine movements of the hands and feet also may be tested by a motor skill or body movement test module 168 and/or user-health test function unit 140. Rapid alternating movements, such as wiping one palm alternately with the palm and dorsum of the other hand, may be tested as well. A common test of coordination is the finger—nose—finger test, in which the user is asked to alternately touch their nose and an examiner's finger as quickly as possible. Ataxia may be revealed if the examiner's finger is held at the extreme of the user's reach, and if the examiner's finger is occasionally moved suddenly to a different location. Overshoot may be measured by having the user raise both arms suddenly from their lap to a specified level in the air. In addition, pressure can be applied to the user's outstretched arms and then suddenly released. To test the accuracy of movements in a way that requires very little strength, a user can be prompted to repeatedly touch a line drawn on the crease of the user's thumb with the tip of their forefinger; alternatively, a motor skill or body movement test module 168 and/or user-health test function unit 140 may prompt a user to repeatedly touch an object on a touchscreen display.

Normal performance of motor tasks depends on the integrated functioning of multiple sensory and motor subsystems. These include position sense pathways, lower motor neurons, upper motor neurons, the basal ganglia, and the cerebellum. Thus, in order to convincingly demonstrate that abnormalities are due to a cerebellar lesion, one should first test for normal joint position sense, strength, and reflexes and confirm the absence of involuntary movements caused by basal ganglia lesions. As discussed above, appendicular ataxia is usually caused by lesions of the cerebellar hemispheres and associated pathways, while truncal ataxia is often caused by damage to the midline cerebellar vermis and associated pathways.

Another body movement test is the Romberg test, which may indicate a problem in the vestibular or proprioception system. A user is asked to stand with feet together (touching each other). Then the user is prompted to close their eyes. If a problem is present, the user may begin to sway or fall. With the eyes open, three sensory systems provide input to the cerebellum to maintain truncal stability. These are vision, proprioception, and vestibular sense. If there is a mild lesion in the vestibular or proprioception systems, the user is usually able to compensate with the eyes open. When the user closes their eyes, however, visual input is removed and instability can be brought out. If there is a more severe proprioceptive or vestibular lesion, or if there is a midline cerebellar lesion causing truncal instability, the user will be unable to maintain this position even with their eyes open.

In the context of the above motor skill or body movement test function, as set forth herein available data arising from the user-health test function are one or more of various types of user-application interaction data 260 described herein. Altered motor skill or body movement function may indicate certain of the possible conditions discussed above. One skilled in the art can establish or determine parameters or values relating to the one or more types of user data indicative of altered motor skill function, or the one or more types of user data indicative of a likely condition associated with altered motor skill function. Parameters or values can be set by one skilled in the art based on knowledge, direct experience, or using available resources such as websites, textbooks, journal articles, or the like. Examples of relevant websites can be found in the online Merck Manual at http://www.merck.com/mmhe/sec06/ch077/ch077c.html#tb077_1; and at http://www.jeffmann.net/NeuroGuidemaps/tremor.html. Examples of relevant textbooks include Patten, J. P., "Neurological Differential Diagnosis," Second Ed., Springer-Verlag, London, 2005; Kasper, Braunwald, Fauci, Hauser, Longo, and Jameson, "Harrison's Principles of Internal Medicine," 16$^{th}$ Ed., McGraw-Hill, New York, 2005; Greenberg, M. S., "Handbook of Neurosurgery," 6$^{th}$ Ed., Thieme, Lakeland, 2006; and Victor, M., and Ropper, A. H., "Adams and Victor's Principles of Neurology," 7$^{th}$ Ed., McGraw-Hill, New York, 2001.

Operation 604 depicts specifying at least one of a plurality of user-health test functions responsive to at least a keyboard-mediated interaction between the user and the at least one advertiser-specified attribute. For example, a user-health test function unit 140 and/or user-health test function assignment module 130 may specify at least one of a plurality of user-health test functions responsive to a keyboard-mediated interaction between the user and the at least one advertiser-specified attribute 122. A user input device 282 may generate and/or record user-application interaction data 260 indicating an interaction between the user and at least one advertiser-specified attribute 122.

User-application interaction data 132 may be from a keyboard-mediated interaction between a user 106 and at least one application 120. For example, a user 106 may use a keyboard at a personal computer, a keyboard on a mobile device such as a cell phone, a mobile email and/or internet device such as a blackberry®, or the like. Keyboard-generated data may be the basis for a number of user-health test functions. For example, a reaction time test function implemented by mental status test module 142 may be responsive to user typing data, in which case user typing speed may be indicative of user reaction time.

Operation 606 depicts specifying at least one of a plurality of user-health test functions responsive to at least a pointing device-mediated interaction between the user and the at least one advertiser-specified attribute. For example, a user-health test function unit 140 and/or user-health test function assignment module 130 may specify at least one of a plurality of user-health test functions responsive to at least a pointing device-mediated interaction between the user and the at least one advertiser-specified attribute 122. A user input device 282, user monitoring device 284, and/or user interface 280 may generate and/or record user-application interaction data 260 indicating an interaction between the user and at least one advertiser-specified attribute 122.

User-application interaction data 260 may be from a pointing device-mediated interaction between a user 106 and at least one application 120. For example, a user 106 may use a mouse, trackball, infrared signal, a stylus, a wired or wireless remote pointing device such as a Wii® remote, finger on a touchpad, or the like. Pointing device-generated data may be the basis for a number of user-health test functions. For example, a motor skill test function implemented by motor skill or body movement test module 168 may be responsive to a user's ability to manipulate a remote control device including an accelerometer in the context of a game, in which case user pointing proficiency may be indicative of the user's motor skill.

Operation 608 depicts specifying at least one of a plurality of user-health test functions responsive to at least an imaging device-mediated interaction between the user and the at least one advertiser-specified attribute. For example, a user-health test function unit 140 and/or user-health test function assignment module 130 may specify at least one of a plurality of user-health test functions responsive to at least an imaging device-mediated interaction between the user and the at least one advertiser-specified attribute 122. A user monitoring device 284 and/or user interface 280 may generate and/or record user-application interaction data 260 indicating an interaction between the user and at least one advertiser-specified attribute 122.

User-application interaction data 132 may be from an imaging device-mediated interaction between a user 106 and at least one application 120. For example, a user 106 and/or device 108 may capture user image data with a still camera, a video camera such as a webcam, an infrared camera, scanner, or the like.

An example of user image data may include data from a user monitoring device 284, such as a video capture device or a video communication device, for example, when a user's image is captured as a photograph or video when using an application, or when a user's image is captured when communicating via a photography or video-based application. Other examples of user image data may include biometric data such as facial pattern data, eye scanning data, or the like. Such user image data may indicate, for example, alertness, attention, motor skill function impairment, or the like, as discussed above.

User image data may include results of visual spectrum imaging that can image changes in facial expression, body movement, or the like that can be indicative of an interaction, indicative of a symptom, and/or indicative of a disease. User image data may also include other kinds of imaging such as infrared imaging that can read a heat signature, or near infrared imaging that can image blood flow changes in the brain and other parts of the body. Other kinds of imaging such as ultrasound imaging and/or x-ray imaging may also be used to produce image data. All of these imaging methods can used to give indications of user behavior and/or physiologic state. Further, reflected image or refracted image data may be used, including x-ray image data, ultrasound image data, and/or near infrared image data. Near infrared imaging may be used to test for baseline physiologic states and metabolism, as well as physiologic and metabolic changes. User image data may be of all or a portion of the user such as a head-to-toe image, a face image, an image of fingers, an image of an eye, or the like. Such images may be in the visual or non-visual wavelength range of the electromagnetic spectrum.

FIG. 7 illustrates alternative embodiments of the example operational flow 300 of FIG. 3. FIG. 7 illustrates example embodiments where the specifying operation 310 may include at least one additional operation. Additional operations may include operation 700, 702, 704, 706, and/or operation 708.

Operation 700 depicts specifying at least one of a plurality of user-health test functions responsive to at least an audio device-mediated interaction between the user and the at least one advertiser-specified attribute. For example, a user-health test function unit 140 and/or user-health test function assignment module 130 may specify at least one of a plurality of user-health test functions responsive to at least an audio device-mediated interaction between the user and the at least one advertiser-specified attribute 122. A user input device 282, user monitoring device 284, and/or user interface 280 may generate and/or record user-application interaction data 260 indicating an interaction between the user and at least one audio device-implemented advertiser-specified attribute 122, such as an audio commercial.

User-application interaction data 132 may be from an audio device-mediated interaction between a user 106 and at least one application 120. For example, a user 106 may listen to audio data including an advertiser-specified attribute 222 on a device 108, such as a computer, a personal entertainment device (e.g., a cell phone such as an iphone), a music player such as an ipod, or the like. As a further example, a user 106 and/or device 108 may capture user voice or speech data with a microphone, telephone, cell phone, or the like. Alternatively, user-application interaction data 132 may include an audio signal transmitted to the user 106 by, for example device 108 via a speaker, including headphones, earphones, earbuds, or the like.

An example of user voice or speech data may include data from a speech or voice input device, or user monitoring device 284, such as a telephonic device or a video communication device with sound receiving/transmission capability, for example when a user task requires, for example, speaking, singing, or other vocalization, as discussed above.

Various kinds of user data may be inputs for a user-health test function. A user-health test function unit 140 can receive user-application interaction data 132 from an interaction between user 106 and local instance of application 110. Such user-application interaction data 260 may be generated via a user interface 280, user input device 282, or a user monitoring device 284. User-health test function unit 240, either resident on device 208 or resident on an external device such as server 112 that communicates with device 108, can obtain, for example, user data such as user reaction time data, user speech or voice data, user hearing data, user body movement, eye movement, or pupil movement data, user face pattern data, user keystroke data, user pointing device manipulation data, user cognitive function data, user memory function data, user internet usage data, and/or user image data, for example, as user-application interaction data 132.

Examples of user-health test function output 190 may include baseline user attributes such as reaction time, motor skill function, visual field range, or the like. Further examples of user-health test function output 290 may include an aggregation or distillation of user data acquired over a period of time. Statistical filters may be applied to user data by the user-health test function 290, or profiles corresponding to various health-related problems may be matched with user data and/or a distillation of user data.

Examples of reaction time data may include speed of a user 106's response to an advertiser-specified attribute 222 such as a prompting icon on a display, for example by clicking with a mouse or other pointing device or by some other response mode. For example, within a game situation a user 106 may be prompted to click on an advertiser-specified target as a test of alertness or awareness. Data may be collected once or many times for this task. A multiplicity of data points indicating a change in reaction time may be indicative of a change in alertness, awareness, neglect, construction, memory, hearing, or other user-health attribute as discussed above.

An example of user movement data may include data from a pointing device when a user is prompted to activate or click an advertiser-specified area on a display to test, for example, visual field range or motor skill function. Another example is visual data of a user's body, for example during a videoconference, wherein changes in facial movement, limb movement, or other body movements are detectable, as discussed above, perhaps during an interaction between a user and an advertiser-specified attribute 222.

An example of user cognitive function data may include data from a text or number input device or user monitoring device when a user is prompted to, for example, spell, write, speak, or calculate in order to test, for example, alertness, ability to calculate, speech, motor skill function, or the like, as discussed above, perhaps during an interaction between a user and an advertiser-specified attribute 222.

An example of user memory function data may include data from a user input device 282 such as a text or number input device or a user monitoring device 284 when a user is prompted to, for example, spell, write, speak, or calculate in order to test, for example, short-term memory, long-term memory, or the like, as discussed above.

An example of user eye movement data may include data from a user monitoring device 284, such as a video communication device, for example, when a user task requires tracking advertiser-specified objects on a display, reading, or during resting states between activities in an application, as discussed above. A further example includes pupillary reflex data from the user at rest following an interaction between a user and an advertiser-specified attribute 222 or during an activity required by an application 220 or user-health test function 244.

An example of user internet usage data may include data from a user's pointing device (including ability to click on elements of a web page, for example), browser history/function (including sites visited, ability to navigate from one site to another, ability to go back to a previous website if prompted, or the like), monitoring device, such as a video communication device, for example, when an application task or user-health test function task requires interaction with a web browser. Such data may indicate cognitive, memory, or motor skill function impairment, or the like, as discussed above. Other examples of internet usage data may include data from a user's offline interaction with internet content obtained while online, including for example an interaction between a user 106 and an advertiser-specified attribute 222 on a web page.

Operation 702 depicts specifying at least one of a plurality of user-health test functions responsive to an interaction between the user and at least one device-implemented game configured to present the at least one advertiser-specified attribute.

For example, a user-health test function unit 140 and/or user-health test function assignment module 130 may specify at least one of a plurality of user-health test functions responsive to an interaction between the user and at least one device-implemented game configured to present the at least one advertiser-specified attribute 122. Such a game may generate, record, and/or elicit user-application interaction data 132 via a user interface 280, user input device 282, and/or a user monitoring device 284. Examples of a user input device 282 include a text entry device such as a keyboard, a pointing device such as a mouse, a touchscreen, a video game controller, or the like. Examples of a user monitoring device 284 include a microphone, a photography device, a video device, or the like.

Examples of a device-implemented game may include a computer game such as, for example, solitaire, puzzle games, role-playing games, first-person shooting games, strategy games, sports games, racing games, adventure games, or the like. Such games may be played offline or through a network (e.g., online games). A device-implemented game also may include virtual world programs such as Second Life and the Sims.

Operation 704 depicts specifying at least one of a plurality of user-health test functions responsive to an interaction between the user and at least one device-implemented security application configured to present the at least one advertiser-specified attribute. For example, a user-health test function unit 140 and/or user-health test function assignment module 130 may specify at least one of a plurality of user-health test functions responsive to an interaction between the user and at least one device-implemented security application configured to present the at least one advertiser-specified attribute 122. Such a security application may generate, record, and/or elicit user-application interaction data 132 via a user interface 280, user input device 282, and/or a user monitoring device 284. Examples of a user input device 282 include a text entry device such as a keyboard, a pointing device such as a mouse, a touchscreen, a video game controller, or the like. Examples of a user monitoring device 284 include a microphone, a photography device, a video device, or the like.

Examples of a security application may include a password entry program, a code entry system, a biometric identification application (e.g., fingerprint scanner, iris and/or retina scanner, voice or speech recognition system, face pattern recognition system, or the like), a video monitoring system, or the like.

Operation 706 depicts specifying at least one of a plurality of user-health test functions responsive to an interaction between the user and at least one device-implemented communication application configured to present at least one advertiser-specified attribute. For example, a user-health test function unit 140 and/or user-health test function assignment module 130 may specify at least one of a plurality of user-health test functions responsive to an interaction between the user and at least one device-implemented communication application configured to present the at least one advertiser-specified attribute 122. Such a communication application may generate, record, and/or elicit user-application interaction data 132 via a user interface 280, user input device 282, and/or a user monitoring device 284. Examples of a user input device 282 include a text entry device such as a keyboard, a pointing device such as a mouse, a touchscreen, a video game controller, or the like. In one embodiment, a pen or other writing implement having electronic signaling capacity may be the user input device 282. Such a pen may include an accelerometer function and/or other sensing functions that allow it to identify and/or signal writing or other motion, writing surface, location of writing activity, or the like. A pen including electronic sensing capability may include the capability to monitor a user's hand for temperature, blood flow, tremor, fingerprints, or other attributes. Other examples of a user monitoring device 284 include a microphone, a photography device, a video device, or the like.

Examples of a communication application may include various forms of one-way or two-way information transfer, typically to, from, between, or among devices. Some examples of communication applications include: an email program, a telephony application, a videocommunication function, an internet or other network messaging program, a cell phone communication application, or the like. Such a communication application may operate via text, voice, video, or other means of communication, combinations of these, or other means of communication.

Operation 708 depicts specifying at least one of a plurality of user-health test functions responsive to an interaction between the user and at least one device-implemented productivity application configured to present the at least one advertiser-specified attribute. For example, a user-health test function unit 140 and/or user-health test function assignment module 130 may specify at least one of a plurality of user-health test functions responsive to an interaction between the user and at least one device-implemented communication application configured to present the at least one advertiser-specified attribute 122. Such a productivity application may generate, record, and/or elicit user-application interaction data 132 via a user interface 280, user input device 282, and/or a user monitoring device 284. Examples of a user input device 282 include a text entry device such as a keyboard, a pointing device such as a mouse, a touchscreen, a video game controller, or the like. Examples of a user monitoring device 284 include a microphone, a photography device, a video device, or the like. Examples of a productivity application may include a word processing program, a spreadsheet program, business software, or the like.

FIG. 8 illustrates alternative embodiments of the example operational flow 300 of FIG. 3. FIG. 8 illustrates example embodiments where the specifying operation 310 may include at least one additional operation. Additional operations may include operation 800, 802, 804, 806, and/or operation 808.

Operation 800 depicts specifying at least one of a plurality of user-health test functions responsive to the interaction between the user and at least one advertiser-specified color. For example, a user-health test function unit 140 and/or user-health test function assignment module 130 may specify at least one of a plurality of user-health test functions responsive to an interaction between the user and at least one advertiser-specified color. Such an advertiser-specified color may be found in the context of a user's interaction with application 120 which may generate, record, and/or elicit user-application interaction data 132 via a user interface 280, user input device 282, and/or a user monitoring device 284. Examples of an advertiser-specified color may include a red color on a banner advertisement on a website, a gray color on a plaid suit worn by an avatar in a virtual world, a yellow color on a shield worn by a character in a computer game, a blue color on a product in a virtual world, or the like.

Operation 802 depicts specifying at least one of a plurality of user-health test functions responsive to the interaction between the user and at least one advertiser-specified textual display. For example, a user-health test function unit 140 and/or user-health test function assignment module 130 may specify at least one of a plurality of user-health test functions responsive to an interaction between the user and at least one advertiser-specified textual display. Such an advertiser-specified textual display may be found in the context of a user's interaction with application 220 which may generate, record, and/or elicit user-application interaction data 260 via a user interface 280, user input device 282, and/or a user monitoring device 284. Examples of an advertiser-specificed textual display may include a slogan on a banner advertisement on a website, a message on a t-shirt worn by an avatar in a virtual world, a sale advertisement on a product in a virtual world and/or website, or the like.

Operation 804 depicts specifying at least one of a plurality of user-health test functions responsive to the interaction between the user and at least one advertiser-specified design. For example, a user-health test function unit 140 and/or user-health test function assignment module 130 may specify at least one of a plurality of user-health test functions responsive to an interaction between the user and at least one advertiser-specified design. Such an advertiser-specified design may be found in the context of a user's interaction with application 220 which may generate, record, and/or elicit user-application interaction data 260 via a user interface 280, user input device 282, and/or a user monitoring device 284. Examples of an advertiser-specified design may include a trade dress of a product's packaging on a website, a product configuration presented by an avatar in a virtual world, an advertising design in a virtual world and/or website, or the like.

Operation 806 depicts specifying at least one of a plurality of user-health test functions responsive to the interaction between the user and at least one advertiser-specified sound. For example, a user-health test function unit 140 and/or user-health test function assignment module 130 may specify at least one of a plurality of user-health test functions responsive to an interaction between the user and at least one advertiser-specified sound. Such an advertiser-specified sound may be found in the context of a user's interaction with application 220 which may generate, record, and/or elicit user-application interaction data 260 via a user interface 280, user input device 282, and/or a user monitoring device 284. Examples of an advertiser-specified sound may include a musical jingle on a website, a product name spoken by an avatar and/or user 106 in a virtual world, a musical work for sale or exchange, or the like.

Operation 808 depicts specifying at least one user-health test function responsive to the interaction between the user and at least one device-implemented application configured to present at least one advertiser-specified brand. For example, a user-health test function unit 140 and/or user-health test function assignment module 130 may specify at least one of a plurality of user-health test functions responsive to an interaction between the user and at least one advertiser-specified brand. Such an advertiser-specified brand may be found in the context of a user's interaction with application 220 which may generate, record, and/or elicit user-application interaction data 260 via a user interface 280, user input device 282, and/or a user monitoring device 284. Examples of an advertiser-specified brand may include, for example, a can of Coke® on a website, a McDonald's® product presented by an avatar in a virtual world, a Metallica song in an online game, or the like.

FIG. 9 illustrates alternative embodiments of the example operational flow 300 of FIG. 3. FIG. 9 illustrates example embodiments where the transmitting operation 320 may include at least one additional operation. Additional operations may include operation 900, 902, 904, 906, and/or operation 908.

Operation 900 depicts sending to at least one entity at least one measure of the user's attention to the at least one advertiser-specified attribute as the at least one output of the at least one user-health test function related to the at least one advertiser-specified attribute. For example, a user-health test function unit 140, user-health test function assignment module 130, and/or user-health test function output routing module 292 may send to at least one of an advertiser, an advertising broker, or a merchant at least one measure of the user's attention to the at least one advertiser-specified attribute as the at least one output of the at least one user-health test function related to the at least one advertiser-specified attribute.

In one embodiment, a user-health test function unit 140, user-health test function assignment module 130, and/or user-health test function output routing module 292 may send to an advertiser a user's reaction time data obtained during an interaction between the user and an advertiser-specified game operable within a website. In another embodiment, a user-health test function unit 140, user-health test function assignment module 130, and/or user-health test function output routing module 292 may send to a merchant entity a user's visual field data obtained during an interaction between the user and an advertiser-specified display in a virtual world. In another embodiment, a user-health test function unit 140, user-health test function assignment module 130, and/or user-health test function output routing module 292 may send to an advertising broker a user's face pattern data obtained during an interaction between the user and an advertiser-specificed musical work played as an adjunct to an email program, word processing program, or the like.

Operation 902 depicts sending to at least one entity at least one measure of the user's pupil movements or eye movements relating to the at least one advertiser-specified attribute as the at least one output of the at least one user-health test function related to the at least one advertiser-specified attribute. For example, a user-health test function unit 140, user-health test function assignment module 130, and/or user-health test function output routing module 292 may send to at least one of an advertiser, an advertising broker, or a merchant at least one measure of a user's pupil movements or eye movements relating to the at least one advertiser-specified attribute as the at least one output of the at least one user-health test function related to the at least one advertiser-specified attribute.

In one embodiment, a user-health test function unit 140, user-health test function assignment module 130, and/or user-health test function output routing module 292 may send to a merchant a user's pupil movement data obtained during an interaction between the user and a product displayed on a website. In another embodiment, a user-health test function unit 140, user-health test function assignment module 130, and/or user-health test function output routing module 292 may send to an advertiser a user's eye movement data obtained during an interaction between the user and an advertisement displayed in a virtual world. In another embodiment, a user-health test function unit 140, user-health test function assignment module 130, and/or user-health test function output routing module 292 may send to an advertising broker a user's eye movement data obtained during an interaction between the user and an advertiser-specified message displayed on a virtual world avatar, or the like.

Operation 904 depicts sending to at least one entity at least one measure of the user's memory relating to the at least one advertiser-specified attribute as the at least one output of the at least one user-health test function related to the at least one advertiser-specified attribute. For example, a user-health test function unit 140, user-health test function assignment module 130, and/or user-health test function output routing module 292 may send to at least one of an advertiser, an advertising broker, or a merchant at least one measure of a user's memory relating to the at least one advertiser-specified attribute as the at least one output of the at least one user-health test function related to the at least one advertiser-specified attribute.

In one embodiment, a user-health test function unit 140, user-health test function assignment module 130, and/or user-health test function output routing module 292 may send to a merchant a user's memory data obtained during an interaction between the user and an advertiser-specified quiz on a website. In another embodiment, a user-health test function unit 140, user-health test function assignment module 130, and/or user-health test function output routing module 292 may send to an advertiser a user's memory data obtained during an interaction between the user and an object associated with an brand within a computer game or virtual world (e.g., a Rolex® watch or a Tiffany's bracelet). In another embodiment, a user-health test function unit 140, user-health test function assignment module 130, and/or user-health test function output routing module 292 may send to an advertising broker a user's memory data obtained during an interaction between the user and an advertiser-specified message displayed on a website banner, or the like.

Operation 906 depicts sending to at least one entity at least one measure of the user's visual field relating to the at least one advertiser-specified attribute as the at least one output of the at least one user-health test function related to the at least one advertiser-specified attribute. For example, a user-health test function unit 140, user-health test function assignment module 130, and/or user-health test function output routing module 292 may send to at least one of an advertiser, an advertising broker, or a merchant at least one measure of a user's visual field relating to the at least one advertiser-specified attribute as the at least one output of the at least one user-health test function related to the at least one advertiser-specified attribute.

In one embodiment, a user-health test function unit 140, user-health test function assignment module 130, and/or user-health test function output routing module 292 may send to a merchant a user's visual field data obtained during an interaction between the user and an advertisement on a website. In another embodiment, a user-health test function unit 140, user-health test function assignment module 130, and/or user-health test function output routing module 292 may send to an advertiser a user's visual field data obtained during an interaction between the user and an object associated with an brand within a computer game or virtual world (e.g., a Tony Hawk brand t-shirt or a Body Glove brand surf board). In another embodiment, a user-health test function unit 140, user-health test function assignment module 130, and/or user-health test function output routing module 292 may send to an advertising broker a user's visual field data obtained during an interaction between the user and an advertiser-specified message displayed on a website banner, or the like.

Operation 908 depicts sending to at least one entity at least one measure of the user's face pattern relating to the at least one advertiser-specified attribute as the at least one output of the at least one user-health test function related to the at least one advertiser-specified attribute. For example, a user-health test function unit 140, user-health test function assignment module 130, and/or user-health test function output routing module 292 may send to at least one of an advertiser, an advertising broker, or a merchant at least one measure of a user's face pattern relating to the at least one advertiser-specified attribute as the at least one output of the at least one user-health test function related to the at least one advertiser-specified attribute.

In one embodiment, a user-health test function unit 140, user-health test function assignment module 130, and/or user-health test function output routing module 292 may send to a merchant a user's face pattern data obtained during an interaction between the user and an advertiser-specified image on a website. In another embodiment, a user-health test function unit 140, user-health test function assignment module 130, and/or user-health test function output routing module 292 may send to an advertiser a user's face pattern data obtained during an interaction between the user and an object associated with an brand within a computer game or virtual world (e.g., an Apple brand computer or a Chevrolet brand automobile). In another embodiment, a user-health test function unit 140, user-health test function assignment module 130, and/or user-health test function output routing module 292 may send to an advertising broker a user's face pattern data obtained during an interaction between the user and an advertiser-specified musical clip played on a website, or the like.

FIG. 10 illustrates alternative embodiments of the example operational flow 300 of FIG. 3. FIG. 10 illustrates example embodiments where the flow 300 may include at least one additional operation. Additional operations may include operation 1030, 1000, 1002, 1004, 1006, and/or operation 1008.

Operation 1030 depicts receiving an indication of interest from at least one entity in at least a portion of the at least one output of the at least one user-health test function. For example, a user 106, a server 212 and/or a user-health test function output routing module 292 may receive an indication of interest from at least one entity 278 in at least a portion of the at least one user-health test function ouput 290. The indication of interest may be received from, for example, advertiser 270, advertising broker 272, advertising agency 274, and/or merchant 276, or the like. In one embodiment, the indication of interest may be an offer to purchase a portion or all of the available user-health test function output 290. In another embodiment, the indication of interest may be a request from an entity 170 to server 112 and/or user-health test function unit 140 for a subscription to future user-health test function ouput 190. For example, user 106, server 112 and/or user-health test function assignment module 130 may receive a request for access to at least one user-health test function output 190 such as a number of data samples, a data over a period of time (e.g., 5 days, 3 months, a year), or the like.

Operation 1000 depicts receiving a request from the at least one entity for a subscription to at least a portion of the at least one output of the at least one user-health test function. For example, a user 106, a server 112 and/or a user-health test function assignment module 130 may receive an order for a subscription to at least a portion of the at least one user-health test function ouput 190 from at least one entity 170. The request for a subscription may be received from, for example, advertiser 270, advertising broker 272, advertising agency 274, and/or merchant 276, or the like. In one embodiment, the subscription may be an offer to purchase a portion or all of the available user-health test function output 190 for a period of weeks, months, or years. In another embodiment, the request for a subscription may be a request from an entity 170 to server 112 and/or user-health test function unit 140 for a subscription to all future user-health test function ouput 190 from one or more users. In another embodiment, an advertising host website including server 212 may receive a request from a merchant to obtain access to, for example, user-health test function output 290 from an eye movement or pupil movement test module 158 for a six week period of time, for example during a certain advertising campaign on the host website.

Operation 1002 depicts receiving an indication of interest from at least one of an advertiser, an advertising broker, an advertising seller, a marketer, a merchant, or a host of advertising as the at least one entity. For example, a user 106, a server 212 and/or a user-health test function output routing module 292 may receive an indication of interest from at least one of an advertiser 102, an advertising broker 272, an advertising agency 274, an advertising seller, a marketer, a merchant 276, a host of advertising, or the like as the at least one entity. In one embodiment, the indication of interest may be an offer to purchase a portion or all of the available user-health test function output 290 from an internet advertiser such as WPP Group, Publicis, and Interpublic Group. In another embodiment, the indication of interest may be a request to server 112 and/or user-health test function unit 140 for a subscription to future user-health test function ouput 190 from an advertising broker such as a company that can match an advertiser to a web page hosting service to obtain an indication of interest in the user-health test function output 290. In another embodiment, an indication of interest may be received from, for example, an advertising seller such as Google and Microsoft. In another embodiment, an indication of interest may be received from, for example, a marketer such as an advertising strategy services company, or the like. In another embodiment, an indication of interest in user-health test function ouput 190 may be received from, for example, a host of advertising such as a television network, a radio station, an internet portal or search engine, or the like.

Operation 1004 depicts receiving an indication of interest from a researcher as the at least one entity. For example, a user 106, a server 112 and/or a user-health test function assignment module 130 may receive an indication of interest in at least a portion of the at least one user-health test function ouput 190 from at least one researcher as the at least one entity 170. The indication of interest may be a request for a subscription received from, for example, a marketing researcher, a university researcher, a government researcher, or the like.

Operation 1006 depicts receiving an indication of interest from at least one of an online game company, an internet search company, a virtual world company, an online product vendor, or a website host as the at least one entity. For example, a user 106, a server 212 and/or a user-health test function output routing module 292 may receive an indication of interest from at least one of an online game company, an internet search company, a virtual world company, an online product vendor, a website host, or the like as the at least one entity. In one embodiment, the indication of interest may be an offer to purchase a portion or all of the available user-health test function output 290 from an online game company such as Blizzard Entertainment, Sony Online Entertainment, or the like. In another embodiment, the indication of interest may be a request to user 106, server 112 and/or user-health test function unit 140 for a subscription to future user-health test function ouput 190 from an internet search company such as Google, Microsoft, Yahoo, or the like to obtain an indication of interest in the user-health test function output 290. In another embodiment, an indication of interest may be received from, for example, a virtual world company such as Linden Lab, Maxis, Makena Technologies, or the like. In another embodiment, an indication of interest may be received from, for example, an online product vendor such as Apple's iTunes, Netflix, Alienware, Valve Corporation's Steam software delivery service, or the like. In another embodiment, an indication of interest in user-health test function ouput 190 may be received from, for example, a website host such as Web.com, HostMonster, BlueHost, or the like to obtain an indication of interest in at least a portion of the at least one output of the at least one user-health test function.

Operation 1008 depicts receiving an indication of interest from a law enforcement entity as the at least one entity. For example, a user 106, a server 112 and/or a user-health test function assignment module 130 may receive an indication of interest in at least a portion of the at least one user-health test function ouput 190 from at least one law enforcement entity as the at least one entity 170. The indication of interest may be, for example, a request for a subscription to user-health test function output 190 for a period of time, received from, for example, the Federal Bureau of Investigation, Central Intelligence Agency, Department of Homeland Security, Interpol, state or local police, or the like.

FIG. 11 illustrates alternative embodiments of the example operational flow 300 of FIG. 10. FIG. 11 illustrates example embodiments in which the receiving operation 1030 may include at least one additional operation. Additional operations may include operation 1100, 1102, 1104, 1106, and/or operation 1108.

Operation 1100 depicts receiving an indication of interest from a teammate as the at least one entity. For example, a user 106, a server 212 and/or a user-health test function routing module 292 may receive an indication of interest in at least a portion of the at least one user-health test function ouput 290 from at least one law enforcement entity as the at least one entity 278. The indication of interest may be, for example, a request for a specific user-health test function output 290 such as a measure of the alertness of user 106, received from, for example, a teammate in an online game such as Counterstrike, Halo3, World of Warcraft.

Operation 1102 depicts receiving an indication of interest in at least one statistical characteristic of the at least a portion of the at least one output of the at least one user-health test function. For example, a user 106, a server 212 and/or a user-health test function routing module 292 may receive an indication of interest in at least one statistical characteristic of the at least a portion of at least one user-health test function ouput 290. For example, a user 106 may receive a request for average user pointing device-manipulation data or average user eye movement data with respect to one or more elements of an entity's website such as MySpace.com or Facebook.com, one or more elements in a virtual world, and/or one more elements in an computerized game world.

Operation 1104 depicts receiving an indication of interest in anonymized output of the at least a portion of the at least one output of the at least one user-health test function. For example, a user 106, a server 212 and/or a user-health test function routing module 292 may receive an indication of interest in anonymized user-health test function ouput 290.

For example, an advertiser 102 such as Google or Nielsen Media Research may receive a request for anonymized data from an eye movement or pupil movement test module 158 operative with respect to a user's interaction with one or more elements of an entity's television program, one or more elements in a virtual world, and/or one or more elements in an computerized game world. In another embodiment, a user 106, device 108, user-health test function unit 140, user-health test function assignment module 130, and/or server 112 may receive an indication of interest in aggregated, anonymous user face pattern test function data (e.g., face pattern test module 160 output) or anonymized user alertness data (e.g., alertness or attention test module 148 output) with respect to a user's interaction with one or more elements of a virtual world segment or an online news website. Anonymization of user-health data and/or user-health test function output 190 may be accomplished through various methods known in the art, including data coding, k-anonymization, de-association, pseudonymization, or the like. User-health test function unit 140, server 112, device 108, and/or user-health test function output routing module 292 may perform the anonymization function.

Operation 1106 depicts receiving compensation for access to the at least one output of the at least one user-health test function. For example, a user 106, a server 212 and/or a user-health test function routing module 292 may receive a payment in exchange for access to user-health test function ouput 290. For example, an advertising server 212 operated by a company such as Google or Yahoo may receive payment in exchange for anonymized data from an eye movement or pupil movement test module 158 operative with respect to a user's interaction with one or more elements of an entity's website, one or more elements in a virtual world, and/or one more elements in an computerized game world. In one embodiment, payment may be based on a quantity of user-health test function output 290 accessed, or payment may be set at a rate per unit time during which user-health test function output 290 is accessed by entity 278. In another embodiment, a user 106, a server 212 and/or a user-health test function routing module 292 may receive a qualification for insurance coverage from an insurance company as the entity 170, for example based on a time period of access to user-health test function output 290. Other kinds of compensation may include subscription fees for online games or virtual world participation, virtual currency, or web hosting services.

Operation 1108 depicts receiving at least one of a payment or a micropayment for access to the at least one output of the at least one user-health test function. For example, a user 106, a server 212 and/or a user-health test function routing module 292 may receive a credit payment or a micropayment in exchange for access to user-health test function ouput 290. For example, an advertising server 212 operated by a company such as Google or Microsoft may receive a micropayment in exchange for user-health test function output 290 from an individual relating to a specific interaction, or for user-health test function output 290 derived from respective interactions between a plurality of users and a specific advertiser-specified attribute within an application 220, such as an in-game advertisement or the like. In another embodiment, a user 106, a server 212 and/or a user-health test function routing module 292 may receive a "per access" micropayment from an entity 278 based on an access schedule permitting the entity 278 to sample whatever quantity of user-health test function output 290 that is available at any given time.

FIG. 12 illustrates a partial view of an example computer program product 1200 that includes a computer program 1204 for executing a computer process on a computing device. An embodiment of the example computer program product 1200 is provided using a signal bearing medium 1202, and may include one or more instructions for specifying at least one of a plurality of user-health test functions responsive to an interaction between a user and at least one advertiser-specified attribute; and one or more instructions for transmitting at least one output of the at least one user-health test function related to the at least one advertiser-specified attribute. The one or more instructions may be, for example, computer executable and/or logic-implemented instructions. In one implementation, the signal-bearing medium 1202 may include a computer-readable medium 1206. In one implementation, the signal bearing medium 1202 may include a recordable medium 1208. In one implementation, the signal bearing medium 1202 may include a communications medium 1210.

FIG. 13 illustrates an example system 1300 in which embodiments may be implemented. The system 1300 includes a computing system environment. The system 1300 also illustrates a user 106 using a device 1304, which is optionally shown as being in communication with a computing device 1302 by way of an optional coupling 1306. The optional coupling 1306 may represent a local, wide-area, or peer-to-peer network, or may represent a bus that is internal to a computing device (e.g., in example embodiments in which the computing device 1302 is contained in whole or in part within the device 1304). A storage medium 1308 may be any computer storage media. In one embodiment, the computing device 1302 may include a virtual machine operating within another computing device. In an alternative embodiment, the computing device 1302 may include a virtual machine operating within a program running on a remote server.

The computing device 1302 includes computer-executable instructions 1310 that when executed on the computing device 1302 cause the computing device 1302 to (a) specify at least one of a plurality of user-health test functions responsive to an interaction between a user and at least one advertiser-specified attribute; and (b) transmit at least one output of the at least one user-health test function related to the at least one advertiser-specified attribute. As referenced above and as shown in FIG. 13, in some examples, the computing device 1302 may optionally be contained in whole or in part within the device 1304.

In FIG. 13, then, the system 1300 includes at least one computing device (e.g., 1302 and/or 1304). The computer-executable instructions 1310 may be executed on one or more of the at least one computing device. For example, the computing device 1302 may implement the computer-executable instructions 1310 and output a result to (and/or receive data from) the computing device 1304. Since the computing device 1302 may be wholly or partially contained within the computing device 1304, the device 1304 also may be said to execute some or all of the computer-executable instructions 1310, in order to be caused to perform or implement, for example, various ones of the techniques described herein, or other techniques.

The device 1304 may include, for example, a portable computing device, workstation, or desktop computing device. In another example embodiment, the computing device 1302 is operable to communicate with the device 1304 associated with the user 106 to receive information about the input from the user 106 for performing data access and data processing, and transmitting at least one output of the at least one user-health test function related to the at least one advertiser-specified attribute.

Although a user 106 is shown/described herein as a single illustrated figure, those skilled in the art will appreciate that a user 106 may be representative of a human user, a robotic user (e.g., computational entity), and/or substantially any combination thereof (e.g., a user may be assisted by one or more robotic agents). In addition, a user 106, as set forth herein, although shown as a single entity may in fact be composed of two or more entities. Those skilled in the art will appreciate that, in general, the same may be said of "sender" and/or other entity-oriented terms as such terms are used herein.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

All of the above U.S. patents, U.S. patent application publications, U.S. patent applications, foreign patents, foreign patent applications and non-patent publications referred to in this specification and/or listed in any Application Data Sheet are incorporated herein by reference, to the extent not inconsistent herewith.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

What is claimed is:

1. A system comprising:
   means for specifying at least one of a plurality of user-health test functions responsive to an interaction between a user and at least one advertiser-specified attribute; and
   means for transmitting at least one output of the at least one user-health test function related to the at least one advertiser-specified attribute.

2. The system of claim 1 wherein the means for specifying at least one of a plurality of user-health test functions responsive to an interaction between a user and at least one advertiser-specified attribute comprises:
   means for specifying at least one of a plurality of user-health test functions responsive to an interaction between a user and at least one device-implemented application configured to present the at least one advertiser-specified attribute.

3. The system of claim 1 wherein the means for specifying at least one of a plurality of user-health test functions responsive to an interaction between a user and at least one advertiser-specified attribute comprises:
   means for specifying at least one alertness or attention test function responsive to the interaction between the user and the at least one advertiser-specified attribute.

4. The system of claim 1 wherein the means for specifying at least one of a plurality of user-health test functions responsive to an interaction between a user and at least one advertiser-specified attribute comprises:
   means for specifying at least one memory test function responsive to the interaction between the user and the at least one advertiser-specified attribute.

5. The system of claim 1 wherein the means for specifying at least one of a plurality of user-health test functions responsive to an interaction between a user and at least one advertiser-specified attribute comprises:
   means for specifying at least one speech or voice test function responsive to the interaction between the user and the at least one advertiser-specified attribute.

6. The system of claim 1 wherein the means for specifying at least one of a plurality of user-health test functions responsive to an interaction between a user and at least one advertiser-specified attribute comprises:
   means for specifying at least one calculation test function responsive to the interaction between the user and the at least one advertiser-specified attribute.

7. The system of claim 1 wherein the means for specifying at least one of a plurality of user-health test functions responsive to an interaction between a user and at least one advertiser-specified attribute comprises:
   means for specifying at least one neglect or construction test function responsive to the interaction between the user and the at least one advertiser-specified attribute.

8. The system of claim 1 wherein the means for specifying at least one of a plurality of user-health test functions responsive to an interaction between a user and at least one advertiser-specified attribute comprises:
   means for specifying at least one task sequencing test function responsive to the interaction between the user and the at least one advertiser-specified attribute.

9. The system of claim 1 wherein the means for specifying at least one of a plurality of user-health test functions responsive to an interaction between a user and at least one advertiser-specified attribute comprises:
   means for specifying at least one visual field test function responsive to the interaction between the user and the at least one advertiser-specified attribute.

10. The system of claim 1 wherein the means for specifying at least one of a plurality of user-health test functions responsive to an interaction between a user and at least one advertiser-specified attribute comprises:
    means for specifying at least one pupil movement or eye movement test function responsive to the interaction between the user and the at least one advertiser-specified attribute.

11. The system of claim 1 wherein the means for specifying at least one of a plurality of user-health test functions responsive to an interaction between a user and at least one advertiser-specified attribute comprises:
    means for specifying at least one face pattern test function responsive to the interaction between the user and the at least one advertiser-specified attribute.

12. The system of claim 1 wherein the means for specifying at least one of a plurality of user-health test functions responsive to an interaction between a user and at least one advertiser-specified attribute comprises:
    means for specifying at least one hearing test function responsive to the interaction between the user and the at least one advertiser-specified attribute.

13. The system of claim 1 wherein the means for specifying at least one of a plurality of user-health test functions responsive to an interaction between a user and at least one advertiser-specified attribute comprises:
   means for specifying at least one motor skill or body movement test function responsive to the interaction between the user and the at least one advertiser-specified attribute.

14. The system of claim 1 wherein the means for specifying at least one of a plurality of user-health test functions responsive to an interaction between a user and at least one advertiser-specified attribute comprises:
   means for specifying at least one of a plurality of user-health test functions responsive to at least a keyboard-mediated interaction between the user and the at least one advertiser-specified attribute.

15. The system of claim 1 wherein the means for specifying at least one of a plurality of user-health test functions responsive to an interaction between a user and at least one advertiser-specified attribute comprises:
   means for specifying at least one of a plurality of user-health test functions responsive to at least a pointing device-mediated interaction between the user and the at least one advertiser-specified attribute.

16. The system of claim 1 wherein the means for specifying at least one of a plurality of user-health test functions responsive to an interaction between a user and at least one advertiser-specified attribute comprises:
   means for specifying at least one of a plurality of user-health test functions responsive to at least an imaging device-mediated interaction between the user and the at least one advertiser-specified attribute.

17. The system of claim 1 wherein the means for specifying at least one of a plurality of user-health test functions responsive to an interaction between a user and at least one advertiser-specified attribute comprises:
   means for specifying at least one of a plurality of user-health test functions responsive to at least an audio device-mediated interaction between the user and the at least one advertiser-specified attribute.

18. The system of claim 1 wherein the means for specifying at least one of a plurality of user-health test functions responsive to an interaction between a user and at least one advertiser-specified attribute comprises:
   means for specifying at least one of a plurality of user-health test functions responsive to an interaction between the user and at least one device-implemented game configured to present the at least one advertiser-specified attribute.

19. The system of claim 1 wherein the means for specifying at least one of a plurality of user-health test functions responsive to an interaction between a user and at least one advertiser-specified attribute comprises:
   means for specifying at least one of a plurality of user-health test functions responsive to an interaction between the user and at least one device-implemented security application configured to present the at least one advertiser-specified attribute.

20. The system of claim 1 wherein the means for specifying at least one of a plurality of user-health test functions responsive to an interaction between a user and at least one advertiser-specified attribute comprises:
   means for specifying at least one of a plurality of user-health test functions responsive to an interaction between the user and at least one device-implemented communication application configured to present at least one advertiser-specified attribute.

21. The system of claim 1 wherein the means for specifying at least one of a plurality of user-health test functions responsive to an interaction between a user and at least one advertiser-specified attribute comprises:
   means for specifying at least one of a plurality of user-health test functions responsive to an interaction between the user and at least one device-implemented productivity application configured to present the at least one advertiser-specified attribute.

22. The system of claim 1 wherein the means for specifying at least one of a plurality of user-health test functions responsive to an interaction between a user and at least one advertiser-specified attribute comprises:
   means for specifying at least one of a plurality of user-health test functions responsive to the interaction between the user and at least one advertiser-specified color.

23. The system of claim 1 wherein the means for specifying at least one of a plurality of user-health test functions responsive to an interaction between a user and at least one advertiser-specified attribute comprises:
   means for specifying at least one of a plurality of user-health test functions responsive to the interaction between the user and at least one advertiser-specified textual display.

24. The system of claim 1 wherein the means for specifying at least one of a plurality of user-health test functions responsive to an interaction between a user and at least one advertiser-specified attribute comprises:
   means for specifying at least one of a plurality of user-health test functions responsive to the interaction between the user and at least one advertiser-specified design.

25. The system of claim 1 wherein the means for specifying at least one of a plurality of user-health test functions responsive to an interaction between a user and at least one advertiser-specified attribute comprises:
   means for specifying at least one of a plurality of user-health test functions responsive to the interaction between the user and at least one advertiser-specified sound.

26. The system of claim 1 wherein the means for specifying at least one of a plurality of user-health test functions responsive to an interaction between a user and at least one advertiser-specified attribute comprises:
   means for specifying at least one user-health test function responsive to the interaction between the user and at least one device-implemented application configured to present at least one advertiser-specified brand.

27. The system of claim 1 wherein the means for transmitting at least one output of the at least one user-health test function related to the at least one advertiser-specified attribute comprises:
   means for sending to at least one entity at least one measure of the user's attention to the at least one advertiser-specified attribute as the at least one output of the at least one user-health test function related to the at least one advertiser-specified attribute.

28. The system of claim 1 wherein the means for transmitting at least one output of the at least one user-health test function related to the at least one advertiser-specified attribute comprises:
   means for sending to at least one entity at least one measure of the user's pupil movements or eye movements relating to the at least one advertiser-specified attribute as the at least one output of the at least one user-health test function related to the at least one advertiser-specified attribute.

29. The system of claim 1 wherein the means for transmitting at least one output of the at least one user-health test function related to the at least one advertiser-specified attribute comprises:
means for sending to at least one entity at least one measure of the user's memory relating to the at least one advertiser-specified attribute as the at least one output of the at least one user-health test function related to the at least one advertiser-specified attribute.

30. The system of claim 1 wherein the means for transmitting at least one output of the at least one user-health test function related to the at least one advertiser-specified attribute comprises:
means for sending to at least one entity at least one measure of the user's visual field relating to the at least one advertiser-specified attribute as the at least one output of the at least one user-health test function related to the at least one advertiser-specified attribute.

31. The system of claim 1 wherein the means for transmitting at least one output of the at least one user-health test function related to the at least one advertiser-specified attribute comprises:
means for sending to at least one entity at least one measure of the user's face pattern relating to the at least one advertiser-specified attribute as the at least one output of the at least one user-health test function related to the at least one advertiser-specified attribute.

32. The system of claim 1 further comprising:
means for receiving an indication of interest from at least one entity in at least a portion of the at least one output of the at least one user-health test function.

33. The system of claim 32 wherein the means for receiving an indication of interest from at least one entity in at least a portion of the at least one output of the at least one user-health test function comprises:
means for receiving a request from the at least one entity for a subscription to at least a portion of the at least one output of the at least one user-health test function.

34. The system of claim 32 wherein the means for receiving an indication of interest from at least one entity in at least a portion of the at least one output of the at least one user-health test function comprises:
means for receiving an indication of interest from at least one of an advertiser, an advertising broker, an advertising seller, a marketer, a merchant, or a host of advertising as the at least one entity.

35. The system of claim 32 wherein the means for receiving an indication of interest from at least one entity in at least a portion of the at least one output of the at least one user-health test function comprises:
means for receiving an indication of interest from a researcher as the at least one entity.

36. The system of claim 32 wherein the means for receiving an indication of interest from at least one entity in at least a portion of the at least one output of the at least one user-health test function comprises:
means for receiving an indication of interest from at least one of an online game company, an internet search company, a virtual world company, an online product vendor, or a website host as the at least one entity.

37. The system of claim 32 wherein the means for receiving an indication of interest from at least one entity in at least a portion of the at least one output of the at least one user-health test function comprises:
means for receiving an indication of interest from a law enforcement entity as the at least one entity.

38. The system of claim 32 wherein the means for receiving an indication of interest from at least one entity in at least a portion of the at least one output of the at least one user-health test function comprises:
means for receiving an indication of interest from a teammate as the at least one entity.

39. The system of claim 32 wherein the means for receiving an indication of interest from at least one entity in at least a portion of the at least one output of the at least one user-health test function comprises:
means for receiving an indication of interest in at least one statistical characteristic of the at least a portion of the at least one output of the at least one user-health test function.

40. The system of claim 32 wherein the means for receiving an indication of interest from at least one entity in at least a portion of the at least one output of the at least one user-health test function comprises:
means for receiving an indication of interest in anonymized output of the at least a portion of the at least one output of the at least one user-health test function.

41. The system of claim 1 wherein the means for receiving an indication of interest from at least one entity in at least a portion of the at least one output of the at least one user-health test function comprises:
means for receiving compensation for access to the at least one output of the at least one user-health test function.

42. The system of claim 1 wherein the means for receiving an indication of interest from at least one entity in at least a portion of the at least one output of the at least one user-health test function comprises:
means for receiving at least one of a payment or a micropayment for access to the at least one output of the at least one user-health test function.

43. A computer program product comprising:
a signal-bearing medium bearing
(a) one or more instructions for specifying at least one of a plurality of user-health test functions responsive to an interaction between a user and at least one advertiser-specified attribute; and
(b) one or more instructions for transmitting at least one output of the at least one user-health test function related to the at least one advertiser-specified attribute.

44. The computer program product of claim 43, wherein the signal-bearing medium includes a computer-readable medium.

45. The computer program product of claim 43, wherein the signal-bearing medium includes a recordable medium.

46. The computer program product of claim 43, wherein the signal-bearing medium includes a communications medium.

47. A system comprising:
a computing device; and
instructions that when executed on the computing device cause the computing device to (a) specify at least one of a plurality of user-health test functions responsive to an interaction between a user and at least one advertiser-specified attribute; and (b) transmit at least one output of the at least one user-health test function related to the at least one advertiser-specified attribute.

48. The system of claim 47 wherein the computing device comprises:

one or more of a personal digital assistant (PDA), a personal entertainment device, a mobile phone, a laptop computer, a tablet personal computer, a networked computer, a computing system comprised of a cluster of processors, a computing system comprised of a cluster of servers, a workstation computer, and/or a desktop computer.

49. The system of claim 47 wherein the computing device is operable to specify at least one of a plurality of user-health test functions responsive to an interaction between a user and at least one advertiser-specified attribute from at least one memory.

50. The system of claim 47 wherein the computing device is operable to transmit at least one output of the at least one user-health test function related to the at least one advertiser-specified attribute from at least one memory.

* * * * *